(12) United States Patent
Bachovchin

(10) Patent No.: US 6,875,737 B1
(45) Date of Patent: Apr. 5, 2005

(54) MULTIVALENT COMPOUNDS FOR CROSSLINKING RECEPTORS AND USES THEREOF

(75) Inventor: William W. Bachovchin, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/289,321

(22) Filed: Apr. 9, 1999

Related U.S. Application Data

(63) Continuation of application No. 08/837,305, filed on Apr. 11, 1997, now Pat. No. 5,965,532, which is a continuation-in-part of application No. 08/671,756, filed on Jun. 28, 1996, now abandoned.

(51) Int. Cl.[7] .................................................. C07K 2/00
(52) U.S. Cl. ........................ 514/2; 558/286; 558/290; 568/1; 548/535; 530/330; 530/331
(58) Field of Search ............................. 514/2; 558/286, 558/290; 568/1; 548/535; 530/330, 331

(56) References Cited

U.S. PATENT DOCUMENTS

| | | | |
|---|---|---|---|
| 4,318,904 A | 3/1982 | Shaw et al. ................ | 514/18 |
| 4,443,609 A | 4/1984 | Oude Alink et al. .......... | 548/11 |
| 4,499,082 A | 2/1985 | Shenvi et al. ................ | 514/2 |
| 4,582,821 A | 4/1986 | Kettner et al. ................ | 514/18 |
| 4,636,492 A | 1/1987 | Kettner et al. ................ | 514/18 |
| 4,644,055 A | 2/1987 | Kettner et al. ............... | 530/330 |
| 4,652,552 A | 3/1987 | Kettner et al. ................ | 514/18 |
| 4,935,493 A | 6/1990 | Bachovchin et al. ....... | 530/331 |
| 4,963,655 A | 10/1990 | Kinder et al. ............... | 530/331 |
| 5,093,477 A | 3/1992 | Mölling et al. ............. | 530/328 |
| 5,187,157 A | 2/1993 | Kettner et al. ................ | 514/18 |
| 5,215,926 A | 6/1993 | Etchells, III et al. ....... | 436/501 |
| 5,242,904 A | 9/1993 | Kettner et al. ................ | 514/18 |
| 5,250,720 A | 10/1993 | Kettner et al. ............. | 558/288 |
| 5,288,707 A | 2/1994 | Metternich ................. | 514/19 |
| 5,296,604 A | 3/1994 | Hanko et al. ............... | 546/169 |
| 5,329,028 A | 7/1994 | Ashkenazi et al. ......... | 548/548 |
| 5,378,624 A | 1/1995 | Berenson et al. ........... | 435/239 |
| 5,384,410 A | 1/1995 | Kettner et al. ............. | 548/405 |
| 5,444,049 A | 8/1995 | de Nanteuil et al. .......... | 514/18 |
| 5,462,928 A | 10/1995 | Bachovchin et al. ......... | 514/19 |
| 5,506,130 A | 4/1996 | Peterson et al. ......... | 435/240.1 |
| 5,527,923 A | 6/1996 | Klingler et al. ............. | 548/570 |
| 5,543,396 A | 8/1996 | Powers et al. ................. | 514/19 |
| 5,554,728 A | 9/1996 | Basava et al. ............... | 530/327 |
| 5,635,386 A | 6/1997 | Palsson et al. ............. | 435/372 |
| 5,635,387 A | 6/1997 | Fei et al. .................... | 435/378 |
| 5,646,043 A | 7/1997 | Emerson et al. ............ | 435/373 |

FOREIGN PATENT DOCUMENTS

| | | |
|---|---|---|
| DE | 158109 | 12/1982 |
| DE | 270382 A1 | 7/1989 |
| DE | 296075 A5 | 11/1991 |
| EP | 0356223 A2 | 2/1990 |
| EP | 0371467 A2 | 6/1990 |
| EP | 0471651 A2 | 2/1992 |
| EP | 0481311 A2 | 4/1992 |
| EP | 0615978 A1 | 9/1994 |
| EP | 0420913 B1 | 11/1995 |
| EP | 0688788 A1 | 12/1995 |
| WO | WO 89/03223 | 4/1989 |
| WO | WO 91/16339 | 10/1991 |
| WO | WO 91/17767 | 11/1991 |
| WO | WO 92/12140 | 7/1992 |
| WO | WO 92/17490 | 10/1992 |
| WO | WO 93/02057 | 2/1993 |
| WO | WO 93/05011 | 3/1993 |
| WO | WO 93/08259 | 4/1993 |
| WO | WO 93/10127 | 5/1993 |
| WO | WO 93/16102 | 8/1993 |
| WO | WO 94/03055 | 2/1994 |
| WO | WO 94/09132 | 4/1994 |
| WO | WO 94/20526 | 9/1994 |
| WO | WO 94/25873 | 11/1994 |
| WO | WO 94/28915 | 12/1994 |
| WO | WO 94/29335 | 12/1994 |
| WO | WO95/11689 | 5/1995 |
| WO | WO 95/12618 | 5/1995 |
| WO | WO95/15309 | 6/1995 |
| WO | WO 95/15309 | 6/1995 |
| WO | WO 95/29691 | 11/1995 |
| WO | WO 95/34538 | 12/1995 |
| WO | WO 96/40263 | 12/1996 |
| WO | WO 96/40858 | 12/1996 |
| WO | WO 98/00439 | 1/1998 |
| WO | WO 98/50046 | 11/1998 |
| WO | WO 98/50066 | 11/1998 |
| WO | WO 99/16864 | 4/1999 |
| WO | WO 95/29190 | 11/1999 |

OTHER PUBLICATIONS

Ansorge et al., "CD26/Dipeptidyl Peptidase IV in Lymphocyte Growth Regulation" *Advances in Experimental Medicine and Biology* 421: 127–140, 1997.

Wijdenes, J., "Monoclonal Antibodies (mAb) Against gp130 Imitating Cytokines Which use the gp130 for Signal Transduction", 9th International Congress of Immunology, San Francisco, California, USA, pp. 303, 1995, The 9th International Congress of Immunology. Publisher: 9th International Congress of Immunology, San Francisco, CA, USA.

Ansorge, et al., "CD26/Dipeptidyl Peptidase IV in Lymphocyte Growth Regulation", *Advances in Experimental Medicine and Biology*, 421: 127–140, 1997.

(Continued)

*Primary Examiner*—Jon P. Weber
*Assistant Examiner*—David Lukton
(74) *Attorney, Agent, or Firm*—Brenda Herschbach Jarrell; C. Hunter Baker; Choate, Hall & Stewart

(57) ABSTRACT

Synthetic crosslinking homobivalent and heterobivalent compounds have been designed and developed. These compounds are low in molecular weight, have antagonistic or agonistic activity, and induce the association between two identical or similar natural receptors (homobivalent compounds) or induce the association between two different natural receptors (heterobivalent compounds).

21 Claims, 20 Drawing Sheets

OTHER PUBLICATIONS

Cordes, et al., "Transition States for Hydrolysis of Acetals, Ketals, Glycosides, and Glycosylamines," Gandour, Richard D. and Schowen, Richard L. (Eds.), *Transition States of Biochemical Processes*, Plenum Press, New York, N.Y., pp. 429–465, 1978.

Wijdenes, J., "Monoclonal Antibodies (mAb) Against gp130 Imitating Cytokines Which use the gp130 for Signal Transduction", 9th International Congress of Immunology, San Francisco, California, USA, pp. 303, 1995.

Aguila, H.L., et al., "From Stem Cells To Lymphocytes: Biology and Transplantation", *Immun. Rev.*, 157:13–40, (1997).

* Austin, D.J., et al., "Proximity Versus Allostery; The Role of Regulated Protein Dimerization in Biology", *Chemistry & Biology*, 1:131–136, (1994).

* Bachovchin, W.W., et al., "Inhibition of IGA 1 Proteinases From Neisseria Gonorrhoeae And Hemophilus Influenzae By Peptide Prolyl Boronic Acids", *J. Biol. Chem.*, 265:3738–3743 (1990).

* Bailey, P.D., "An Introduction To Peptide Chemistry", *Wiley Publishers*, 1–81, (1990).

* Barton, R.W.J., et al., "Binding Of The T Cell Activation Monoclonal Antibody Ta1 To Dipeptidyl Peptidase IV", *J. Leukocyte Biology*, 48:291–296 (1990).

Baugh, R., et al., "Role and Potential Therapeutic Value of Proteinase Inhibitors in Tissue Destruction", *Proteinases And Tumor Invation*, 165:157–180 (1980).

* Blumenstein, et al., "Synthetic Non–Peptide Inhibitors of HIV Protease" *Biochemical and Biophysical Research Communications* 163(2): 980–87, 1989.

* Bodanszky, M., "Principles Of Peptide Synthesis", *Springer–Verlag*, 16: (1984).

*Bodanszky, M., "The Practice Of Peptide Synthesis", *Springer–Verlag*, 21: (1984).

* Bodanzky, M., "Peptide Chemistry, A Practical Textbook", *Springer–Verlag*, (1988) 1–9.

* Boros, L.G., et al., "Fluoroolefin Peptide Isosteres–Tools For Controlling Peptide Conformations", *Tetrahedron Letters*, 35:6033–6036., (1994).

* Brady, L., and Dodson, G., "Reflections On A Peptide", *Nature*, 368:692–693, (1994).

* Brander, et al., "Heterogeneous T Cell Responses to β–Lactam–Modified Self–Structures Are Observed in Penicillin–Allergic Individuals" *J. Immunol.* 155 (5):2670–2678 (1995).

* Brenchley, et al., "Towards Defining Antigens in Human Membranous Nephropathy" *Nephrology, Dialysis, Transplantation* 7 Supp. 1:21–24, (1992).

Bristol, L.A., et al., "Characterization of a Novel Rat Thymocyte Costimulating Antigen by the Monoclonal Antibody 1.3", *J. Immunol.*, 148:332–338 (1992).

* Bristol, L.A., et al., "Thymocyte Costimulating Antigen is CD26 (Dipeptidyl–Peptidase IV), Co–stimulation of Granulocyte, Macrophage, T Lineage Cell Proliferation Via CD26," *J. Immunol.*, 149:367–372 (1992).

Bristol, et al., "Inhibition of CD26 Enzyme Activity with Pro–boropro Stimulates Rat Granulocyte/Macrophage Colony Formation and Thymocyte Proliferation In Vitro", *Blood*, 85(12): 3602–3609, 1995.

* Bungy, et al., Mapping of T Cell Epitopes of the Major Fraction of Rye Grass Using Peripheral Blood Mononuclear Cells From Atopics and Non–Atopics. II. Isoallergen Clone 5A of Lolium Perenne Group I (Lol p I). *Eur. J. Immunol.* 24 (9):2098–2103 (1994).

* Chan, et al., *Archives of Ophthalmology* 113 (5):597–600 (1995).

* Chazenblak, et al., "Human Organ–Specific Autoimmune Disease", Molecular Cloning and Expression of an Autoantibody Gene Repertoire For a Major Autoantigen Reveals an Antigenic Immunodominant Region and Restricted Immunoglobulin Gene Usage in the Target Organ, *J. Clinical Investigation* 92 (1):62–74 (1993).

* Colowick, S., et al., "Methods In Enzymology", pp. 220–225, vol. 46, 1979.

* Coutts, et al., "Structure–Activity Relationships of Boronic Acid Inhibitors of Dipeptidyl Peptidase IV. 1. Variation of the $P_2$ Position of $X_{aa}$–boroPro Dipeptides", *J. Med. Chem.*, 39: 2087–94, 1996.

* Dang, N.H., et al., "Cell Surface Modulation of CD26 By Anti–IF7 Monocional Antibody: Analysis of Surface Expression and Human T Cell Activation", *J. Immunol.*, 145:3963–3971 (1990).

* Darcy, et al., "Protection of Mice and Nude Rats Against Toxolasmosis by A Multiple Antigenic Peptide Construction Derived From Toxoplasma Gondii P30 Antigen", *J. Immunol.* 149 (11):3636–3641 (1992).

* Darmoul, D., et al. "Dipeptidyl Peptidase IV (CD26) Gene Expression in Enterocyte–like Colon Cancer Cell Lines HT–29 and Caco–2; Cloning of The Complete Human Coding Sequence And Changes of Dipeptidyl Peptidase IV mRNA Levels During Cell Differentiation," *J. Biological Chemistry*, 267:220–2208 (1992).

* Daw, et al., "Glutamic Acid Decarboxylase Autoantibodies in Stiff–Man Syndrome and Insulin–Dependent Diabetes Mellitus Exhibit Similarities and Differences in Epitope Recognition", *J. Immunol.* 156(2): 818–825 (1996).

* De Caestecker, M.P., et al., "The Detection of Intercytoplasmic Interleukin 1 (Alpha) Expression In Human Monocytes Using Two Colour Immunofluorescence Flow Cytometry", *J. Immunol. Methods* 154:11–20 (1992).

* Demuth, H.U., et al. "Design Of (Omega–N–(O–Acyl)– Hydroxy Amid) Aminodicarboxylic Acid Pyrrolidides As Potent of Proline–Specific Peptidases", *FEBS Lett.*, 320:23–27, (1993).

* Dudler, et al., "Carbohydrate–Dependent, HLA Class II–Restricted, Human T Cell Response to the Bee Venom Allergen Phospholipase A2 in Allergen Patients", *Eur. J. Immunol.* 25 (2):538–542 (1995).

Duke–Cohan, J.S., et al., "Targeting of An Activated T–Cell Subset Using A Bispecific Antibody–Toxin Conjugated Directed Against CD4 and CD26", *Blood*, 82:2224–2234., (1993).

Dupont, B., "Immunology Of Hematopoietic Stem Cell Transplantation: A Brief Review Of Its History", *Immun. Rev.*, 157:5–12. (1997).

* Ebenbichler, C., et al., "Structure–function Relationships Of The HIV–1 Envelope V3 Loop Tropism Determinant: Evidence For Two Distinct Conformations", *Aids* 7:639–46 (1993).

* El Far, et al., "Antigens Associated with N– and L–Type Calcium Channels in Lambert–Eaton Myasthenic Syndrome", *J. Neurochemistry*, 64 (4):1696–1702 (1995).

* Fauci, A.S., "The Human Immunodeficiency Virus: Infectivity And Mechanisms Of Pathogenesis", *Science*, 239:617–722 (1988).
* Fleisher, B., et al., "Triggering of Cytotoxic T Lymphocytes and NK Cells Via The Tp 103 Pathway is Dependent On the Expression Of The The T Cell Receptor/CD3 Complex", *J. Immuno,,.* 141:1103–1107.
* Flentke, G.R., et al., "Inhibition Of Dipeptidyl Aminopeptidase IV (DP–IV) By XAA–Boropro Dipetides And Use Of These Inhibitors To Examine The Role Of DP–IV IN T–Cell Function", *Proc. Natl. Acad. Sci. USA*, 88:1556–1559, (1991).
* Freeman, et al., "T and B Cell Reactivity to Adrenal Antigens in Autoimmune Addison's Disease" *Clinical & Experimental Immunology* 88 (2): 275–279 (1992).
Goodman, et al., "Cellular Immunity to Cartilage Aggrecan Core Protein in Patients with Rheumatoid Arthritis and Non–Arthritic Controls", *Annals of the Rheumatic Diseases*, 55: 40–46, 1996.
* Goodman, M., and Chorev, M., "On The Concept Of Linear Modified Retro–Peptide Structures", *Accounts of Chemical Research*, 12:1–7 (1979).
Goodstone, et al., "Cellular Immunity to Cartilage Aggrecan Core Protein in Patients with Rheumatoid Arthritis and Non–Arthritic Controls" *Annals Of The Rheumatic Diseases* 55(1):40–46 (1996).
* Guichard, G., et al. Partially Modified Retro–Inverso Pseudopeptides As Non–Natural Ligands For The Human Class I Histocompatibility Molecule HLA–A2, *J. Med. Chem.*, 39:2030–2039, (1996).
* Günther, U.L., et al., "Solution Strutures Of The DP IV (CD26) Inhibitor Val–BoroPro Determined By NMR Spectroscopy", *Magnetic Resonance in Chem.*, 33:959–970, (1995).
Gutheil, W.G., et al., "Seperation Of L–PRO–DL–Boropro Into Its Component Diastereomers And Kinetic Analysis Of Their Inhibition Of Dipeptidyl Peptidase IV. A New Method For The Analysis Of Slow, Tight–Binding Inhibition", *Biochemistry*, 32:8723–8731, (1993).
* Hall, et al., "Immunogenetics of Dermatitis Herpetiformis", *Seminars in Dermatology*, 10(3):240–245 (1991).
* Hart, et al., "Design of Experimental Synthetic Peptide Immunogens for Prevention of HIV–1 and HTLV–1 Retroviral Infections", *Pharmaceutical Biotechnology* 6:821–845 (1995).
* Hegen, M., et al. "Enzymatic Activity Of CD26 (Dipeptidylpeptidase IV) Is Not Required For Its Signalling Function In T Cells", *Immunobiology*, 189:483–493, (1993).
* Hegen, M., et al. "Function Of Dipeptidylpeptidase IV (CD26, TP103) In Transfected Human T Cells", *Cell Immunol.*, 146:249–260, (1993).
* Hegen, M., et al., The T Cell Triggering Molecule Tp 103, *J. Immunol.*, 144:2980–2914 (1990).
* Heins, J., et al., "Mechanism of Proline–Specific Proteinases: (I) Substrate Specificity of Dipeptidyl Peptidase Peptidase IV From Pig Kidney and Proline–Specific Endopeptidase From Flavobacterium Meningosepticum", *Biochemica Biophysica Acta*, 954:161–169 (1988).
* Ikagawa, et al., "Single Amino and Acid Substitutions on a Japanese Cedar Pollen Allergen Cry J–1) Derived Peptide Induced Alterations in Human T Cell Responses and T Cell Receptor Antagonism" *J. Allergy & Clinical Immunol.* 97 (1 Pt 1): 53–64 (1996).

* James, et al., "Peptide Autoantigenicty of the Small Nuclear Ribonucleoprotein C" *Clinical & Experimental Rheumatology*, 13 (3):299–305 (1995).
* Jameson, B.A., et al., "A Rationally Designed CD4 Analogue Inhibits Experimental Allergic Encephalomyelitis", *Nature*, 368:744–746, (1994).
* Janeway, C., et al., "Immunobiolgy—The Immune System In Health And Disease", *Current Biology LTD*, Chapter 12, pp. 1–35, (1994).
* Jardetzky, T.S., et al., Three–Dimensional Structure Of A HumanClass II Histocompatibility Molecule Complexed With Superantigen, *Nature*, 368:711–718 (1994).
* Jiang, et al., "Inhibition of Human Immunodeficiency Virus Type I Infection in a T–Cell Line (CEM) by New Dipeptidyl–Peptidase IV (CD26) Inhibitors", *Res Viral*, 148: 255–266, 1997.
* Jorgensen, J.L., et al., "Molecular Components Of T–Cell Recognition," *Annu. Rev. Immunol.* 10:835–873 (1992).
* Kalluri, et al., "Identification of the Alpha 3 Chain of Type IV Collagen as the Common Autoantigen in Antibasement Membrane Disease and Goodpasture Syndrone", *J. The American Society of Nephrology* 6 (4):1178–1185 (1995).
* Kameoka, J., et al., "Direct Association of Adenosine Deaminase with A T Cell Activation Antigen, CD26", *Science*, 261:466–469, (1993).
* Kameoka, Jr., et al., "Differential CD26–Mediated Activation of The CD3 and CD2 Pathways After CD6–Depleted Allogenic Bone Marrow Transplantation", *Blood* 85:1132–1137, (1995).
* Karges, et al., "Self and Non–Self Antigen in Diabetic Autoimmunity: Molecules and Mechanisms", *Molecular Aspects of Medicine* 16(2):29–213 (1995).
* Kelly, T.A., et al., "Immunosuppresive Boronic Acid Dipeptides: Correlation Between Conformation and Activity", *J. Am. Chem. Soc.*, 115:12637–12638, (1993).
* Kelly, T.A., et al., "The Efficient Synthesis and Simple Resolution of A Proline Boronate Ester Suitable For Enzyme Inhibition Studies", *Tetrahedron* 49:1009–1016 (1993).
* Kettner, C.A. and Shenvi, A.B., "Peptide Boronic Acid Inhibitors of Trypsin–Like Proteases Their Preparation and Use as Anticoagulants And Inflammation Inhibitors", *Chemical Abstracts*, (1990), 112:80 (91790c).
* Kettner, C.A., et al., "Kinetic Properties of The Binding of Alpha–Lytic Protease To Peptide Boronic Acids", *Biochemistry*, 27:7682–7688, (1988).
* Kinder, D., et al., "Analogues of Carbamyl Aspartate as Inhibitors . . . " *J. Med. Chem.*, 33:819–823 (1990).
* Kokowa, et al., "Detection of Platelet Antigen for Antiplatelet Antibodies in Idiopathic Thrombocytopenic Purpura by Flow Cytometry, Antigen–Capture ELISA, and Immunoblotting: A Comparative Study", *Eur. J. Hematology* 50 (2): 74–80 (1993).
* Kubota, T., et al., "Diipepidyl peptidase IV (DP IV) Activity In Serum and On Lymymphocytes of Mrl/Mp–*Ipr/ Ipr* Mice Correlates with Disease Onset", *Clin. Exp. Immunol*, 96:292–296. (1994).
* Kubota, T., et al., "Involvement Of Dipeptidyl Peptidase IV In An In Vivo Immune Response", *Clin. Exp. Immunol.*, 89:192–197, (1992).
* Kuchroo, V.K., et al., "Single TCR Antagonist Peptide Inhibits Experimental Allergic Encephalomyelitis Mediated By A Diverse T Cell Repertoire", *J. Immunol.* 153:3326–3336 (1994).

* Kuchroo, V.K., et al., "Cytokines and Adhesion Molecules Contribute To The Ability of Myelin Proteolipid Protein–Specific T Cell Clones To Mediate Experimental Allergic Encephalomyelitis", *J. Immunol.* 151:4371–4382 (1993).
* Kuchroo, V.K., et al., "Experimental Allergic Encephalomyelitis Medicated By Cloned T Cells Specific For A Synthetic Peptide of Myelin Proteolipid Protein. Fine Specificity And T Cell Receptor V Beta Usage", *J. Immunol.* 148:3776–3782 (1992).
* Kuchroo, V.K., et al., "Induction of Experimental Allergic Encephalomyelitis By Myelin Proteolipid–Protein–Specific T Cell Clones and Synthetic Peptides", *Pathobiology* 59:305–312 (1991).
* Kuchroo, V.K., et al., "T Cell Receptor (TCR) Usage Determines Disease Susceptibility In Experimental Autoimmune Encephalomyelitis: Studies with TCR V Beta *.2 Transgenic Mice", *J. Experimental Medicine* 179:1659–1664 (1994).
* Kuchroo, V.K., et al., "T–cell Receptor Alpha Chain Plays a Critical Role in Antigen–Specific Suppressor Cell Function", *Proc. Natl. Acad. Sci. USA* 88:8700–8704 (1991).
* Linington, et al., "Cell Adhesion Molecules of the Immunoglobulin Supergene Family as Tissue–Specific Autoantigens: Induction of Experimental Allergic Meuritis (EAN) by PO Protein–Specific T Cell Lines", *Eur. J. Immunol.* 22(7): 1813–1817 (1992).
* Linsley, P.S., et al., "Effects of Anti–gp 120 Monoclonal Antibodies On CD4 Receptor Binding By The Env Protein of Human Immunodeficiency Virus Type 1", *J. Virology* 62:3695–3702 (1988).
* Liu, et al., "Molecular Mapping of a Pathogenically Relevant BP180 Epitope Associated with Experimentally Induced Murine Bullous Pemphigoid" *J. Immunol.* 155 (11): 5449–5454 (1995).
* Lopez, et al., "Characterization of SPf(66)n: A Chimeric Molecule Used as a Malaria Vaccine" *Vaccine*, 12 (7):585–591 (1994).
Luftig, et al., "Update on Viral Pathogenesis", Recent Work on Three Human Pathogens Illustrates the Paths Being Taken in Viral Pathogenesis Research *ASM News*, 56(7): 366–368, 1990.
* Marguett et al., "cDNA Cloning for Mouse Thymocyte–Activating Molecule", A Multifunctional Ecto–Dipeptidyl Peptidase IV (CD26) Included in a Subgroup of Serine Proteases, *The Journal of Biological Chemistry*, 267(4): 2200–2208, 1992.
* Matteson, D., et al., "Synthesis and Properties of Pinanediol a–Amido Boronic Esters" *Organometallics*, 3:1284–1288, (1984).
* Mittrucker, H.W., et al. "The Cytoplasmic Tail of The T Cell Receptor Zeta Chain is Required For Signalling Via CD26", *Eur. J. Immunol.*, 25:295–297, (1995).
* Morimoto, C., et al., 1F7 "A Novel Cell Surface Molecule, Involved in Helper Function of CD4 cells". *J. Immunol.*, 143:34030–3439 (1989) and published erraturm appears in *J. Immunology* 144 (5):2027 (1990).
* Mosmann, T.R., "Cytokine Patterns During The Progression To Aids", *Science*, 265:193–194, (1994).
* Mullins, et al., "Transgenesis in the Rat and Larger Mammals" *J. Clinical Investigation* 96 (1): 30–37 (1996).
* Nardelli, et al., "A Chemically Defined Synthetic Vaccine Model for HIV–1", *J. Immunol.* 148 (3): 914–920 (1992).

* Nicola, N, et al., "Guidebook To Cytokines and Their Receptors", *Sambrook and Tooze Publication*, pp. 1–257, (1994).
* O'Brien, et al., "An Immunogenetic Analysis of the T–Cell Recognition of the Major House Dust Mite Allergen Der p2: Identification of High– and Low–Responder HLA–DQ Alleles and Localization of T–Cell Epitopes" *Immunology* 86 (2):176–182 (1995).
* Panina–Bordignon, P., et al., "Universally Immunogenic T Cell Epitopes: Promiscuous Binding To Human MHC MHC Class II and Promiscuous Recognition By T Cells", *Eur. J. Immunol.* 19:2237–2242 (1989).
* Ostresh, et al., "Generation and Use of Nonsupport–Bound Peptide and Peptidomimetric Combinatorial Libraries", *Methods in Enzymology*, 267: 220–234, 1996.
* Perry, et al., "Autoreactive T Cell Specificity in Autoimmune Hemolytic Anemia of the NZB Mouse", *Eur. J. Immunol.* 26(1): 136–141 (1996).
* Perstorp Biotec Company, "Molecular Biology Catalog", (1994).
* Powers, C., et al., "Elastase Inhibitors For Treatment of Emphysema—NHLBI Workshop Summary" *US Dept. of Health and Human Services*, 1097–1100, (1985).
* Protti, et al., "Myasthenia Gravis: Recognition of a Human Autoantigen at the MolecularLevel" *Immunol. Today* 14 (7):363–368 (1993).
Reinhold, D., et al., "Inhibitors of dipeptidyl peptidase IV (DP IV, CD26) induces secretion of transforming growth factor–1 (TGF–*1*) in simulated mouse splenocytes and thymocytes" *Immunology Letters*, 58:29–35, (1997).
* Reynolds, et al., "T and B Epitope Determination and Analysis of Multiple Antigenic Peptides for the Schistosoma Mansoni Experimental Vaccine Triose–Phosphate Isomerase", *J. Immunol*, 152 (1):193–200 (1994).
Rini, J.M., et al., "Crystal Structure of A Human Immunodeficiency Virus Type I Neutralizing Antibody, 50.1, In Complex With Its V3 Loop Peptide Antigen", *Proc. Natl. Acad. Sci. USA* 90:6325–9 (1993).
* Ritu, et al., "Construction of Synthetic Immunogens: Use of T– and B–Cell Epitopes of CS and RESA Proteins of Plasmodium Falciparum" *Vaccine* 10 (11): 761–765 (1992).
* Scharpe, S., et al., "Purified and Cell–Bound CD26: Enzymatic Inhibition, Antibody Binding Profile, And Expression On T Cells In Relation To Other Surface Markers", *Verh. K. Acad. Geneeskd. Belg.*, 56:537–559. (1994).
Schmitz T., et al., "Potentiation of The Immune Response In Hiv–1 + Individuals", *J. Clin. Invest.*, 97:1545–1549, (1996).
* Schon, E., et al., "Dipeptidyl Peptidase IV in human T Lymphocytes. An Approach To The Role Of A Membrane Peptidase In The Immune System", *Biomedica Biochimica Acta*, 45:1523–1528 (1986).
* Schon, E., et al., "Dipeptidyl Peptidase IV In The Immune System", *Biol. Chem. Hoppe–Seyler*, 372:305–311, (1991).
* Schön, E., et al., "Dipeptidyl Peptidase IV In The Immune System. Effects Of Specific Enzyme Inhibitors On The Activity of Dipeptidyl Peptidase IV and Proliferation Of Human Lymphocytes", *Biological Chemistry Hoppe Seyler* 372:305–311 (1991).
* Schon, E., et al., "Dipeptidyl Peptidase IV, A Membrane Enzyme Involved In The Proliferation Lymphocytes", *Biomedica Biochimica Acta*, 44 (1985).

* Schön, E., et al., "The Role of Dipeptidyl Peptidase IV In Human T Lymphocyte Activation. Inhibitors And Antibodies Against Dipeptidyl Peptidase IV Supress Lymphocyte Proliferation and Immunoglobulin Synthesis In Vitro", *Eur. J. Immunol.* 17:1821–1826 (1987).

* Seed, B., "Making Agonist of Antagonist", *Chemistry& Biology*, 1:125–129 (1994).

* Shimojo, et al., "Identification of the Disease–Related T Cell Epitope of Ovalbumin and Epitope–Targeted T Cell Inactivation in Egg Allergy" *Int'l. Archives of Allergy& Immunol.* 105 (2):155–161 (1994).

* Snow, R.J., et al., "Studies On Proline Boronic Acid Dipeptide Inhibitors Of Dipeptidyl Peptidase IV: Identification Of A Cyclic Species Containing A B–N Bond", *J. Am. Chem. Soc.*, 116:10860–10869, (1994).

* Songyang, Z., et al., "SH2 Domains Recognize Specific Phosphopeptide Sequences", *Cell*, 72:767–778, (1993).

* Subramanyam, M., et al., "CD26, AT–Cell Accessory Molecule Induction of Antigen–Specific Immune–Suppression By Inactivation of CD26: A Clue To The Aids Paraxox?", in *Dipeptidyl Peptidase IV(CD26)in Metabolism and Immune Response*, Ed. B. Fleischer: 155–162, (1995).

* Subramanyam, M., et al., "Mechanism of HiV–1 Tat Induced Inhibition of Antigen–Specific T Cell Responsiveness", *J. Immunol.*, 150:2544–2553, (1993).

Subramanyam, W.G., et al., "Mechanism of HIV–1 Tat Induced Inhibition Of Antigen–Specific T Cell Responsiveness", *J. Immunol.* 150:2544–2553 (1993).

* Studmeier, J.L., et al., "Solution Structures of Active and Inactive Forms of The DP IV (CD26) Inhibitor Pro–Boropro Determined By Nmr Spectroscopy", *Biochemistry*, 33:12427–12438, (1994).

* Tam, J.P., "Synthetic Peptide Vaccine Design: Synthesis And PropertiesOf A High–Density Multiple Antigenic Peptide System", *Proc. Natl. Acad. Sci. USA*, 85:5409–5413, (1988).

* Tanaka, T., et al. "Cloning And Functional Expression Of The T Cell Activation Antigen CD26", *J. Immunol.*, 149:481–486. (1992).

* Tanaka, T., et al., "Cloning And Functional Expression Of The T Cell Activation Antigen CD26", *J. Immunol.* 149: 481–486 (1992); published erratum appears in *J. Immunol.* 50(5):2090 (1993).

* Tanaka, T., et al., "The Costimulatory Activity of The CD26 Antigen Requires Dipeptidyl Peptidase IV Enzaymatic Activity", *Proc. Natl. Acad. Sci. USA*, 90:4586–4590. (1993).

* Thompson, R., "Use Of Peptide Aldehydes To Generate Transition–State Analogs of Elastase", *Biochemistry*, 12:1:47–51 (1973).

Thompson, R. "Peptide Aldehydes: Potent Inhibitors of Serine and Cysteine Proteases", 19:220–225, 1973.

* Uibo, et al., Characterization of Adrenal Autoantigens Recognized by Sera From Patients with Autoimmune Polyglandular Syndrome (APS) Type I. (*J. Autoimmunity* 7(3): 399–411 (1994).

* Van Noort, et al., "The Small Heat–Shock Protein Alpha B–Crystallin as Candidate Autoantigen in Multiple Sclerosis" *Nature* 375 (6534):798–801 1995.

* Watson, J.D., "Continuous Proliferation of Murine Antigen Specific Helper T Lymphocytes in Culture", *J. Experimental Medicine* 150:1510 (1979).

* Welch, J. T., and Lin J., Fluoroolefin Containing Dipetide Isoteres As Inhibitors of Dipeptidyl Peptidase IV (CD26), *Tetrahedron*, 52:291–304, (1995).

* Wyss–Coray, T., et al., "Use of Antibody/Peptides Constructs of Direct Antigenic Peptides To T Cells: Evidence For T Cells Processing And Presentation", *Cellular Immunol.*, 139 (1):268–73 (1992).

* Yoshimoto, T., et al., "Comparison Of Inhibitory Effects of Prolinal–Containing peptide Derivatives On Prolyl . . . ", (1985) J. Biochem., 98:975–979, (1985).

* Zhu, X., et al., "T Cell Epitope Mapping of Ragweed Pollen Allergen Ambrosia Artemisiifolia (Amb a 5) and Ambrosia Trifida (Amb t 5) and the Role of Free Sulfhydryl Groups in T Cell Recognition" *J. Immunol.* 155 (10):5064–5073 (1995).

* Zimmerman, D.H., et al. "A New Approach To T–Cell Activation: Natural and Synthetic Conjugates Capable of Activating T Cells", *Vaccine Res.*, 5:91–102, (1996).

Zimmerman, D.H., et al., "Immunication with Peptide Heteroconjugates Primes A T Helper Cell . . . " *Vaccine Res.* 5:103–118, (1996).

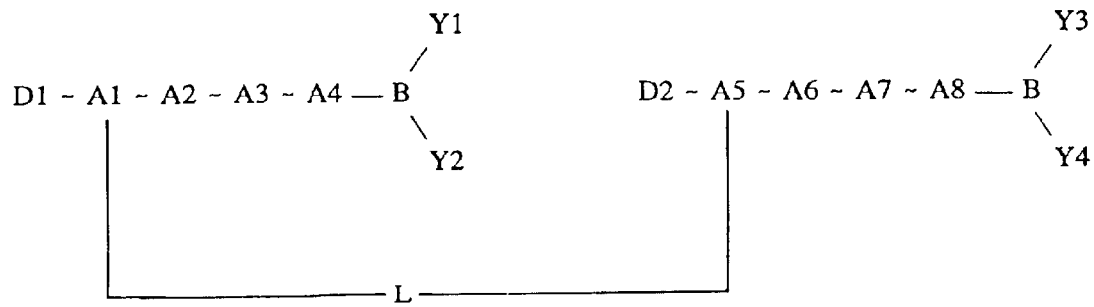
FIG. IA
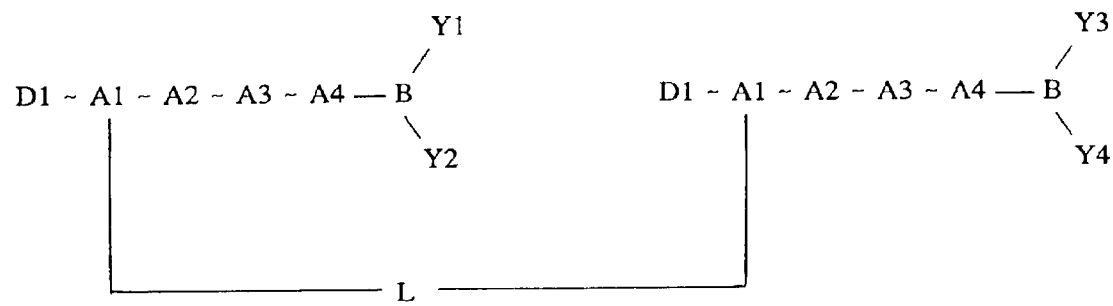
FIG. IB
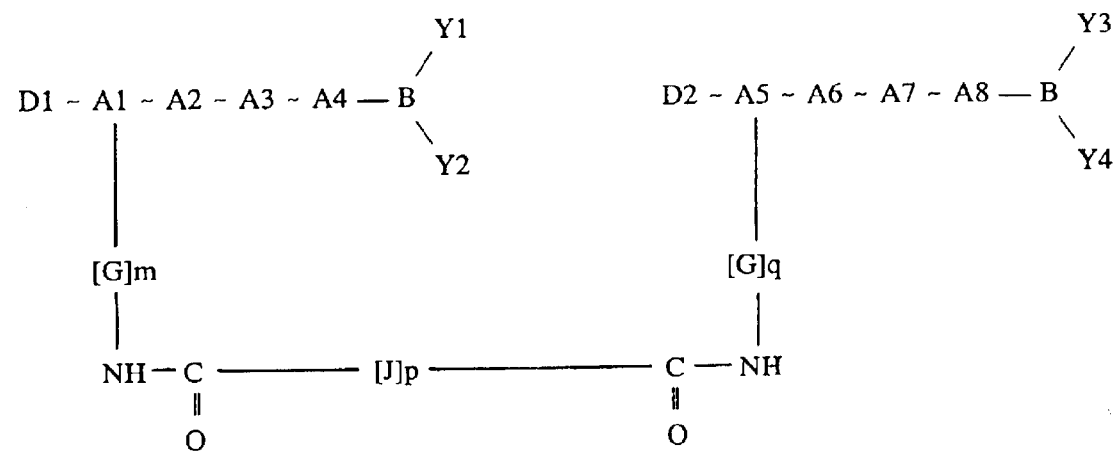
FIG. IC

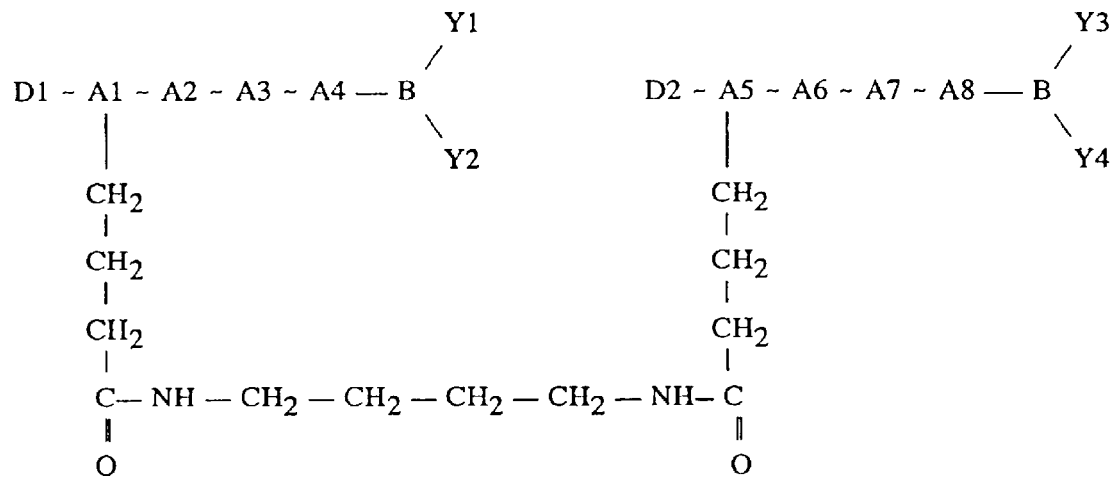
FIG. IJ
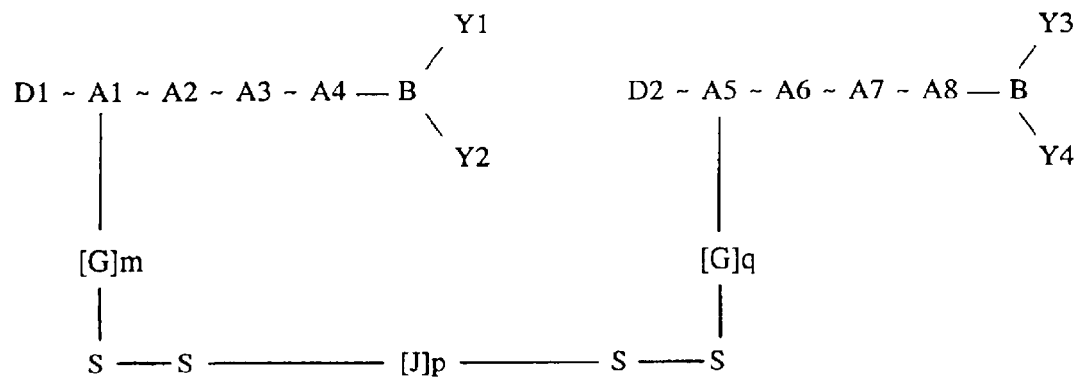
$m, p, q = 1\text{-}50$
FIG. IK

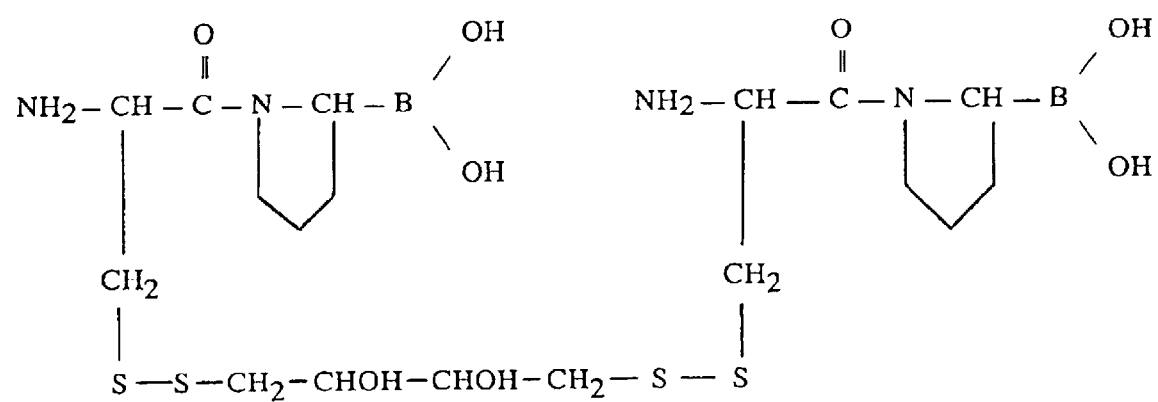
FIG. IN

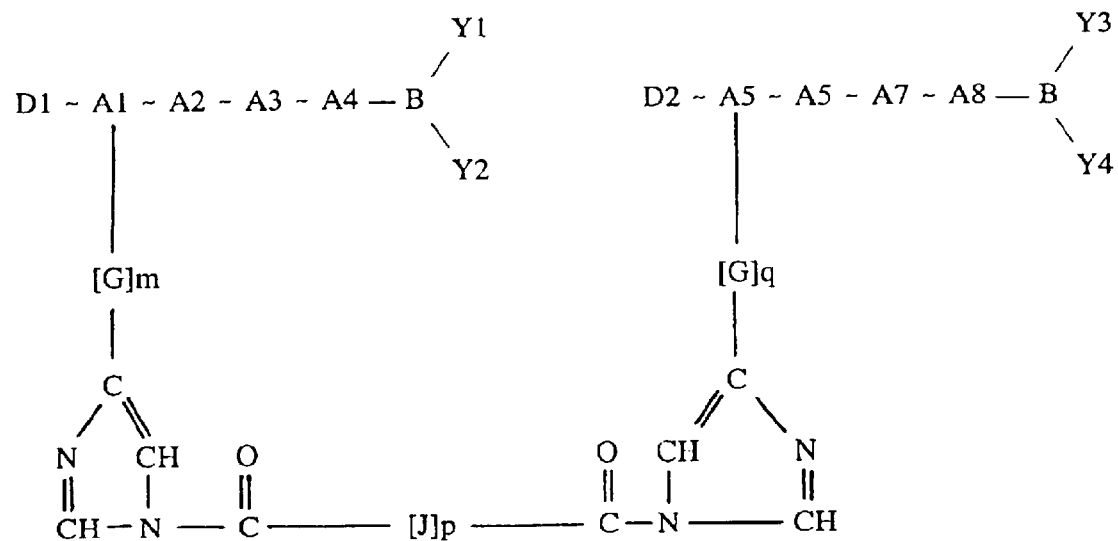
FIG. IP
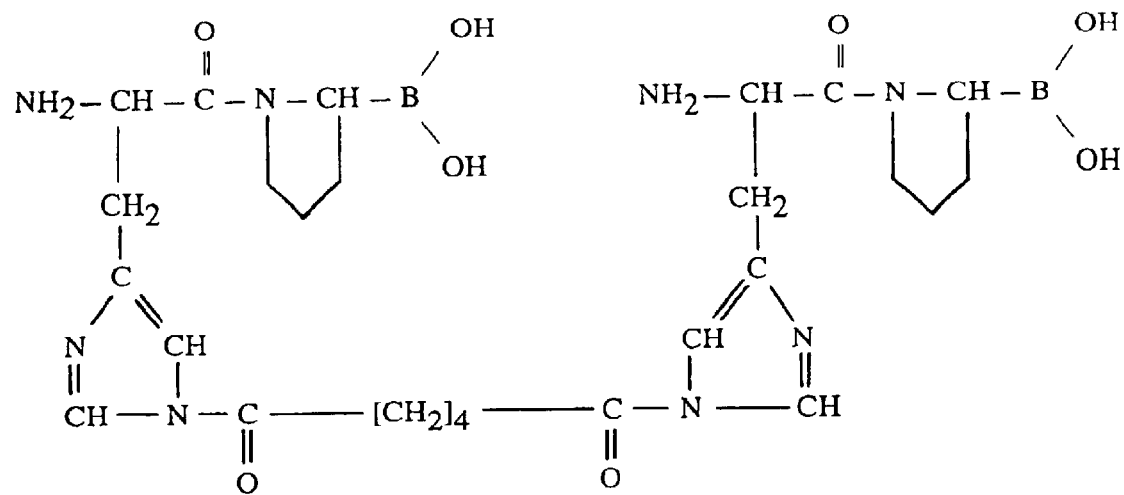
FIG. IQ

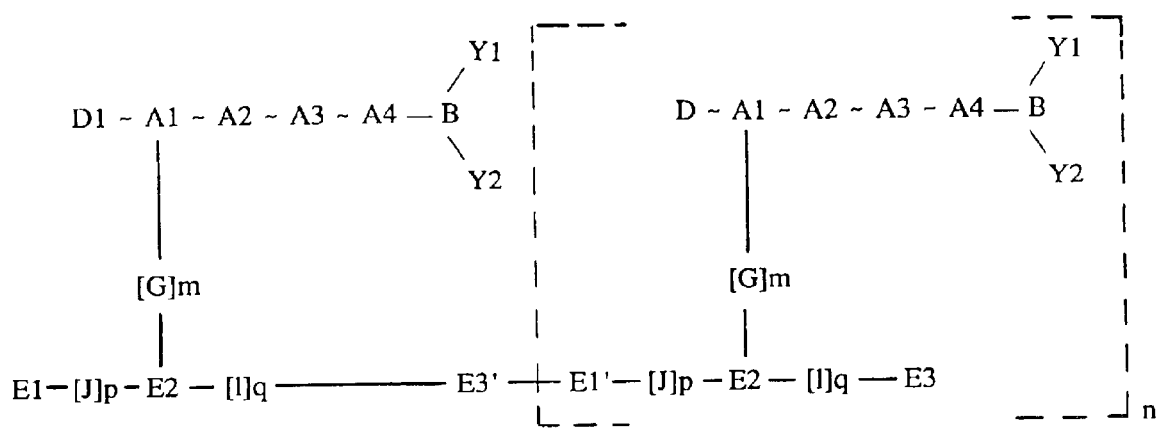
R - E3 + E1 - R' → R - E3' - E1' - R' + F
F ≡ 2H$^+$ + 2e$^-$, H$_2$O, or other byproduct
R & R' ≡ remainder of molecules not relevant to the reaction
FIG. IR

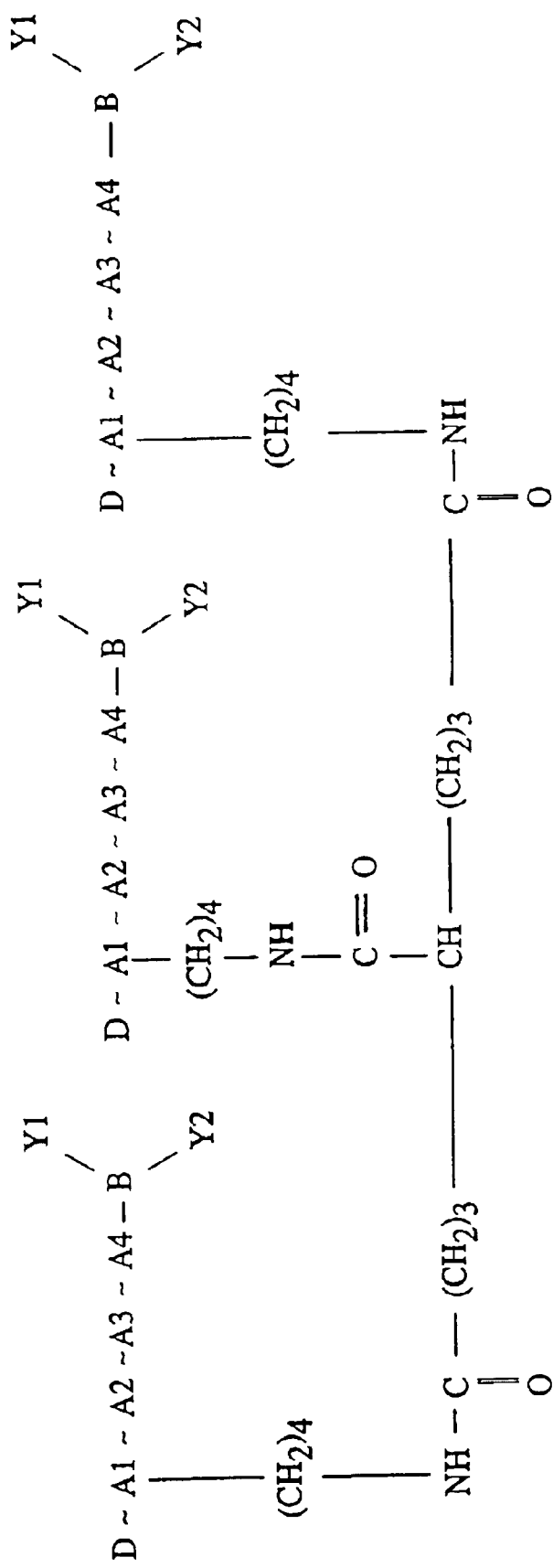
FIG. IS (KbP)$_2$ EGS

EGS: Ethylene glycolbis ( succinimidylsuccinate )

SEQUENCE LISTING

```
<160> NUMBER OF SEQ ID NOS: 9

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:Synthetic

<400> SEQUENCE: 1

Ala Ala Ala Ala Ala Ala
  1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:Synthetic

<400> SEQUENCE: 2

His Ser Leu Gly Lys Trp Leu Gly His Pro Asp Lys Phe
  1               5                  10

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:Synthetic

<400> SEQUENCE: 3

His Ser Leu Gly Lys Trp Leu Gly His Pro Asp Lys Phe Ala Ala Ala
  1               5                  10                  15

Ala Ala Ala

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence:Synthetic

<400> SEQUENCE: 4

Ala Ala Ala Ala Ala Phe Lys Asp Pro His Gly Leu Trp Lys Gly Leu
  1               5                  10                  15

Ser His

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence:Synthetic
```

```
<400> SEQUENCE: 5

His Ser Leu Gly Lys Trp Leu Gly His Pro Asp Lys Phe Ala Ala Ala
  1               5                  10                  15

Ala Ala

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (5)
<223> OTHER INFORMATION: x = any amino acid.

<400> SEQUENCE: 6

Ser Thr Pro Pro Xaa
  1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 7

Ser Thr Pro Pro
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: UNSURE
<222> LOCATION: (4)
<223> OTHER INFORMATION: x = any amino acid.

<400> SEQUENCE: 8

Pro Thr Pro Xaa
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Synthetic

<400> SEQUENCE: 9

Pro Thr Pro Arg
  1
```

MULTIVALENT COMPOUNDS FOR CROSSLINKING RECEPTORS AND USES THEREOF

CROSS REFERENCE TO RELATED APPLICATIONS

This application is a continuation of U.S. Ser. No. 08/837,305 filed Apr. 11, 1997 now U.S. Pat. No. 5,965,532, which is a continuation-in-part of application Ser. No. 08/671,756, filed Jun. 28, 1996 now abandoned.

STATEMENT AS TO FEDERALLY SPONSORED RESEARCH

This invention was made, in part, with U.S. Government support under Grant No. 5-RO1-AI31866 awarded by the National Institute of Allergy and Infectious Diseases.

THE FIELD OF THE INVENTION

This invention relates to low molecular weight bivalent and multivalent crosslinking compounds capable of inducing association between naturally occurring receptors, and particularly to inducing association between T cell surface receptors, e.g., homobivalent induced CD26—CD26 association or heterobivalent induced CD26 association with another T cell surface receptor.

BACKGROUND OF THE INVENTION

Cell surface receptors transmit signals received on the outside of a cell to the inside through two basic mechanisms: (1) ligand-induced allosteric conformational change and (2) ligand-induced association.

The ligands for the ligand-induced, allosteric conformational change mechanism are typically small molecules, such as the catecholamines or the neuropeptide hormones.

The ligand-induced association mechanism involves an association of specific proteins on the cell surface and has only recently been discovered (relatively speaking), but already has been shown to be as widely used and as important as the first mechanism.

Receptors activated by a ligand-induced dimerization include, for example, those for cell growth and differentiation factors. Factors which serve as ligands for these receptors are typically large polypeptide hormone and cytokines such as erythropoietin, granulocyte colony stimulating factor (G-CSF), or granulocyte macrophage colony stimulating factor (GM-CSF), and human growth hormone (hGH). Many of the dimerization-activated receptors have cytoplasmic tails that contain protein kinase domains or docking sites. Ligand-induced dimerization of the extracellular domains of these receptors results in the juxtaposition of their cytoplasmic tails. They then presumably phosphorylate each other in trans and thereby initiate the cytosolic signaling pathway. In some cases the cytoplasmic domains of dimerization-activated receptors do not have kinase domains themselves, but function the same as if they did because they associate with protein kinases via docking sites.

Receptors activated by oligomerization or aggregation are found most frequently in the immune system.

They include, for example, the T cell surface receptors such as CD4, CD8, CD28, CD26, CD45, CD10, and CD3/TCR (T cell antigen receptor). The ligands for these T cell receptors are most often cell surface proteins themselves, and can be found on antigen presenting cells. Aggregation-activated receptors frequently have short cytoplasmic domains which act to bind and thereby recruit other cell surface and/or cytosolic factors following the aggregation of their extracellular domains.

The allosterically activated receptor class has been the primary focus of drug discovery, design, and development efforts for decades. These efforts have yielded many pharmacologically agents. In principle, two distinct types of agents are possible: antagonists and agonists. Antagonists block the binding of the natural ligand without inducing the conformational change in the receptor thereby blocking a signal transduction pathway. Agonists bind to the receptor in a manner which mimics the natural ligand closely enough to induce the same conformational change as natural ligand thereby initiating a signal transduction pathway. See Seed, et al. for a theoretical discussion on how to make an agonist from an antagonist (Seed, B., Making Agonists of Antagonists, *Chemistry & Biology* 1:125 (1994). See Austin, et al. for a discussion of the role of regulated protein dimerization in biology (Austin, et al. *Chemistry & Biology* 1:131 (1994)).

Several association-activation receptors have recently become the targets of drug discovery efforts, owing to the important roles they play in various cellular signaling. Low-molecular weight synthetic molecules, that block the interaction of receptors and their ligands and interfere with signal transduction (i.e., antagonists), have been identified using the methods employed with the allosterically activated class. These low-molecular weight synthetic molecules are potential drugs.

Monomeric inhibitors block recall antigen-induced T cell activation and proliferation (G. R. Flentke, E. Munoz, B. T. Huber, A. G. Plaut, C. A. Kettner, and W. W. Bachovchin. Inhibition of dipeptidyl aminopeptidase IV (DP-IV) by Xaa-boroPro dipeptides and use of these inhibitors to examine the role of DP-IV in T-cell function, *Proceedings of the National Academy of Sciences of the United States of America* 88, 1556–1559 (1991)). A number of anti-CD26 mAbs have the same inhibitory activity when used under non-crosslinking conditions (C. Morimoto, Y. Torimoto, G. Levinson, C. E. Rudd, M. Schrieber, N. H. Dang, N. L. Letvin, and S. F. Schlossman. 1F7, a novel cell surface molecule, involved in helper function of CD4 cells, *Journal of Immunology* 143, 3430–3439 (1989) and published erratum appears in *J. Immunology.* 144(5):2027 (March 1990)). Most anti-CD26 mAbs are stimulatory, rather than inhibitory when used under crosslinking conditions (R. W. Barton, J.; Prendergast, and C. A. Kennedy. Binding of the T cell activation monoclonal antibody Ta1 to dipeptidyl peptidase IV, *Journal of Leukocyte Biology* 48, 291–296 (1990); L. A. Bristol, K, Sakaguchi, E. Appella, D. Doyle, L. Takacs. Thymocyte costimulating antigen is CD26 (dipeptidyl-peptidase IV). Co-stimulation of granulocyte, macrophage, and T lineage cell proliferation via CD26, *Journal of Immunology* 149, 367–372. (1992)., ; L. A. Bristol, L. Finch, E. V. Romm, and L. Takacs. Characterization of a novel rat thymocyte costimulating antigen by the monoclonal antibody 1.3, *Journal of Immunology* 148, 332–338 (1992); B. Fleischer, E. Sturm, V. J. De, and H. Spits. Triggering of cytotoxic T lymphocytes and NK cells via the Tp103 pathway is dependent on the expression of the T cell receptor/CD3 complex, *Journal of Immunology* 141, 1103–11077 (1988); M. Hegen, G. Niedobitek, C. E. Klein, H. Stein; and B. Fleischer. The T cell triggering molecule Tp103 is associated with dipeptidyl aminopeptidase IV activity, *J. Immunol.* 144, 2980–2914 (1990)).

A class of low molecular weight synthetic monomeric molecules with high affinity for CD26 have previously been developed and characterized (G. R. Flentke, E. Munoz, B. T. Huber, A. G. Plaut, C. A. Kettner, and W. W. Bachovchin. Inhibition of dipeptidyl aminopeptidase IV (DP-IV) by Xaa-boroPro dipeptides and use of these inhibitors to examine the role of DP-IV in T-cell function, *Proceedings of the National Academy of Sciences of the United States of America* 88, 1556–1559 (1991); W. G. Gutheil and W. W. Bachovchin. Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993)). These molecules have been shown to be potent and specific synthetic inhibitors for CD26's associated DP IV proteinase activity. DP-IV is a postproline cleaving enzyme with a specificity for removing Xaa-Pro (where Xaa represents any amino acid) dipeptides from the amino terminus of polypeptides.

Representative monomeric structures of these transition-state-analog-based inhibitors, Xaa-boroPro, are e.g., Pro-boroPro and Ala-boroPro. BoroPro refers to the analog of proline in which the carboxylate group (COOH) is replaced with a boronyl group [$B(OH)_2$]. Pro-boroPro, the most thoroughly characterized of these inhibitors has a Ki of 16 picomolar (pM) (W. G. Gutheil and W. W. Bachovchin. Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, *Biochemistry* 32, 8723–8731 (1993)). Val-boroPro has even a higher affinity, with a Ki of 1.6 pM (W. G. Gutheil and W. W. Bachovchin. Supra; R. J. Snow, W. W. Bachovchin, R. B. Barton, S. J. Campbell, S. J. Coutts, D. M. Freeman, and G. W. Gutheil. Studies on Proline boronic Acid Dipeptide Inhibitors of Dipeptidyl Peptidase IV: Identification of a Cyclic Species Containing a B—N Bond, *J. Am. Chem. Soc.* 116, 10860–10869 (1994)). Thus, these Xaa-boroPro inhibitors are about $10^{+4}$ fold more potent than the next best known inhibitors. In comparison, antibodies usually have affinities for their targets between $10^{-8}$ and $10^{-9}$ M.

U.S. Pat. Nos. 4,935,493 (the '493 patent) and 5,462,928 (the '928 patent), both of which are incorporated herein by reference, disclose protease inhibitors and transition state analogs (the '493 patent) and methods for treating transplant rejection in a patient, arthritis, or systemic lupus erythematosis (SLE) by administering a potent inhibitor of the catalytic activity of soluble amino peptidase activity of dipeptidyl peptidase type IV (DP-IV; (G. R. Flentke, E. Munoz, B. T. Huber, A. G. Plaut, C. A. Kettner, and W. W. Bachovchin. Inhibition of dipeptidyl aminopeptidase IV (DP-IV) by Xaa-boroPro dipeptides and use of these inhibitors to examine the role of DP-IV in T-cell function, *Proceedings of the National Academy of Sciences of the United States of America* 88, 1556–1559 (1991)).

Until now, most drug discovery and development efforts have been directed at the allosteric conformational change-activated class of receptors. Also, the efforts directed at the association-activated class have focused on monomeric agents capable of blocking binding of a natural ligand, and therefore blocking signal transduction mediated by these receptors.

Cytotoxic drugs have untoward effects since they indiscriminately kill all proliferating cells. With the advent of monoclonal antibodies, it is possible to increase the specificity of these therapeutic tools. Monoclonal antibodies against the T cell receptors, e.g., T-cell receptor, CD4 and CD8 co-receptors, and to MHC class II molecules, have all been-evaluated for their respective benefit in experimental models for the treatment of autoimmune disease. The major impediment to using monoclonal antibodies as a therapeutic tool in humans, is that most monoclonal antibodies are made in mice, and humans rapidly develop an antibody response to mouse antibodies, which limits their potency because of neutralization and, worse, produces allergic reactions such as immune complex disease. Once this has occurred, all mouse monoclonal antibodies become useless in that patient. To avoid this problem, antibodies which are not recognized as foreign by the human immune system are currently being made via three different ways. One approach is to clone human V regions into a phage display library and select for binding to human cells. Using this method, monoclonal antibodies that are entirely human in origin can be obtained. Second, mice that lack endogenous immunoglobulin genes can be made transgenic for human heavy and light chain loci using yeast artificial chromosomes. Third, one may graft the antigen-binding loops of a mouse monoclonal antibody onto the framework of a human immunoglobulin molecule (a process known as humanization).

Each of these three methods produce monoclonal antibodies which are far less immunogenic in humans than the parent mouse monoclonal antibodies, but with each methods comes a host of additional problems or road-blocks. For example, antiidiotype neutralizing antibodies are often produced in patients receiving monoclonal antibody therapy.

SUMMARY OF THE INVENTION

In general, low molecular weight, bivalent or multivalent, synthetic crosslinking compounds are designed and developed. These synthetic crosslinking compounds may act either as agonists or antagonists and induce association between naturally occurring receptors, e.g., induce the association of one particular T cell surface receptor, such as CD26, with (a) itself or, (b) with another T cell surface receptor (e.g., CD4, CD8, CD28, CD26, CD45, CD10, and CD3/TCR (or TCR/CD3)).

The low molecular weight, bivalent or multivalent, synthetic crosslinking compounds of this invention are small enough (less than about 30 amino acids, and more preferably about 20 amino acids) to obviate the toxicity associated with monoclonal antibodies.

The bivalent or multivalent, synthetic crosslinking compounds of this invention can be administered to a patient without being co-administered with an adjuvant. In contrast, most other peptides, proteins and carbohydrate antigens are usually poorly immunogenic, or not immunogenic at all, when administered without adjuvant.

An aspect of this invention is a bivalent compound, having the structure as shown in FIG. 1A, wherein D1 and D2, independently, are selected from the group consisting of NH and $NH_2$, wherein N represents any isotope of nitrogen, wherein H represents any isotope of hydrogen; "~", independently, is selected from the group consisting of a single bond and a double bond; B represents, independently, any isotope of boron; A1 and A5 are, independently, selected from a group consisting of a C, a CX moiety and an N, wherein C represents any isotope of carbon, wherein X represents any atom capable of forming a single bond with C; each A2, A3, A4, A6, A7, and A8 are, independently, selected from a group consisting of a CX moiety, a CXZ moiety, a CZ moiety, an NX moiety, and an 0, wherein X and Z, are, independently, selected from the group consisting of any atom capable of forming a single bond and any atom capable of forming a double bond with C or N and wherein O represents any isotope of oxygen; wherein each Y1, Y2, Y3, and Y4 are, independently, selected from the group consisting of a hydroxyl moiety and any reactive moiety that converts to a hydroxyl moiety under physiologic conditions; and L represents a linker molecule (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous.

An embodiment of this compound is wherein the structures shown in FIG. 1U and FIG. 1V represent, independently, a binding moiety, wherein R represents the remainder of the molecule.

By definition, the linker molecule must be capable of linking atom A1 of the binding moiety on the left of FIG. 1A to atom A5 of the binding moiety on the right of FIG. 1A.

Other embodiments of this compound include: there are 4 atoms positioned between the group consisting of D1 and D2 and B of the binding moiety; the binding moiety is in an L-configuration; Y1, Y2, Y3, and Y4 are hydroxyl groups; the A4 bonded to the B is in the L-configuration and the A5 bonded to the B is in the L-configuration; the binding moiety is an L-amino acid residue conjugated to B, a boron molecule; the binding moiety is selected from the group consisting of L-Lys-L-boroPro and a derivative of L-Lys-L-boroPro.

Another embodiment of this compound is wherein the linker molecule contains a functional group selected from the group consisting of a carboxylate group, an amino group, a sulfhydryl group, an imidazole group, an alkene group (a carbon atom double bonded to another carbon atom), an acyl halogen group, e.g., an acylchloride, and $CH_2X$, wherein X represents a halogen (e.g., the two binding moieties are linked when a nucleophilic group displaces the halogen from the functional group of the $CH_2X$ linker molecule); wherein the linker molecule is further defined as having the structure as shown in FIG. 1T and wherein [G] is selected from the group consisting of a carbon, nitrogen, oxygen, hydrogen and a sulfur atom; [J] is selected from the group consisting of a $CH_2$ molecule, a chain of carbon atoms, a chain of nitrogen atoms, and a chain of oxygen atoms; and m, p, and q represent an integer from 1 to 50, inclusive; wherein [G] is an R group selected from the group consisting of L-amino acid residues selected from the group consisting of lysine, cysteine, glutamic acid, aspartic acid, histidine, arginine, glutamine, and asparagine and D-amino acid residues selected from the group consisting of lysine, cysteine, glutamic acid, aspartic acid, histidine, arginine, glutamine, and asparagine; wherein the linker molecule is selected from the group consisting of hexanedioic acid (adipic acid), EGS, 1,4-diaminobutane, 1,4-dithiobutane, dithiothreitol, lysine, cysteine, glutamic acid, aspartic acid, histidine, arginine, glutamine, and asparagine; wherein the linker molecule contains at least two amino groups when the binding moieties contain glutamic acid residues; wherein the linker molecule contains at least two amino groups when the binding moieties contain aspartic acid residues; wherein the linker molecule contains at least two sulfhydryl groups when the binding moieties contain cysteine residues; and wherein the linker molecule span ranges from about 30 Å to about 100 Å.

Another aspect of this invention is a compound having the structure as shown in FIG. 1B. In this compound, the binding moieties are identical, e.g., having A1, A2, A3, and A4 in both binding moieties, and wherein D1, is independently selected from the group consisting of NH and $NH_2$, wherein N represents any isotope of nitrogen, wherein H represents any isotope of hydrogen; "~", independently, is selected from the group consisting of a single bond and a double bond; B represents, independently, any isotope of boron; A1 is, independently, selected from a group consisting of a C, a CX moiety and an N, wherein C represents any isotope of carbon, wherein X represents any atom capable of forming a single bond with C; each A2, A3, and A4 are, independently, selected from a group consisting of a CX moiety, a CXZ moiety, a CZ moiety, an NX moiety, and an O, wherein X and Z, are, independently, selected from the group consisting of any atom capable of forming a single bond and any atom capable of forming a double bond with C or N and wherein O represents any isotope of oxygen; wherein each Y1, Y2, Y3, and Y4 are, independently, selected from the group consisting of a hydroxyl moiety and any reactive moiety that converts to a hydroxyl moiety under physiologic conditions; and L represents a linker molecule (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous.

An embodiment of the compound where only A1, A2, A3, and A4 appear in both binding moieties, is the structures shown in FIG. 1U and FIG. 1V which represent, independently, a binding moiety, wherein R represents the remainder of the molecule.

Another aspect of this invention is a compound, having the structure as shown in FIG. 2A, wherein D is independently selected from the group consisting of NH and $NH_2$, wherein N represents any isotope of nitrogen, wherein H represents any isotope of hydrogen; "~", independently, is selected from the group consisting of a single bond and a double bond; B represents, independently, any isotope of boron; A1 is, independently, selected from the group consisting of a C, a CX moiety and an N, wherein C represents any isotope of carbon, wherein X represents any atom capable of forming a single bond with C; each A2, A3, and A4 are, independently, selected from the group consisting of a CX moiety, a CXZ moiety, a CZ moiety, an NX moiety, and an O, wherein X and Z, independently, are selected from the group consisting of any atom capable of forming a single bond and any atom capable of forming a double bond with C or N and wherein O represents any isotope of oxygen; wherein each Y1 and Y2 are, independently, selected from the group consisting of a hydroxyl moiety and any reactive moiety that converts to a hydroxyl moiety under physiologic conditions; L represents a linker molecule (i) having a molecular weight ranging between about 100 daltons about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous; and P represents a peptide ranging from 3 to 30 amino acids having sufficient sequence homology to bind to a naturally occurring receptor.

An embodiment of this compound includes the structures shown in FIGS. 1U and 1V which represent, independently, a binding moiety, wherein R represents the remainder of the molecule.

Other embodiments of this compound include: there are 4 atoms positioned between D and B of the binding moiety; the binding moiety is in an L-configuration; Y1 and Y2 are hydroxyl groups; the A4 bonded to the B is in the L-configuration; the binding moiety is an L-amino acid residue conjugated to B, a boron molecule; and the binding moiety is selected from the group consisting of L-Lys-L-boroPro and a derivative of L-Lys-L-boroPro.

Additional embodiments of this compound is the linker molecule which includes: a functional group selected from the group consisting of a carboxylate group, an amino group, a sulfhydryl group, an imidazole group, an alkene group, an acyl halogen group, and $CH_2X$, wherein X represents a halogen; the linker molecule which is further defined as having the structure shown in FIG. 1T, wherein [G] is selected from the group consisting of a carbon, nitrogen, oxygen, hydrogen and a sulfur atom; [J] is selected from the group consisting of a $CH_2$ molecule, a chain of carbon atoms, a chain of nitrogen atoms, and a chain of oxygen atoms; and m, p, and q represent an integer from 1 to 50, inclusive; wherein [G] is an R group selected from the group consisting of L-amino acid residues selected from the group consisting of lysine, cysteine, glutamic acid, aspartic acid, histidine, arginine, glutamine, and asparagine and D-amino acid residues selected from the group consisting of lysine, cysteine, glutamic acid, aspartic acid, histidine, arginine, glutamine, and asparagine; wherein the linker molecule is selected from the group consisting of adipic acid, between 2 and 15 consecutive amino acid residues, 1,4-diaminobutane, 1,4-dithiobutane, and dithiothreitol; and wherein the linker molecule span ranges from about 30 Å to about 100 Å.

Yet another embodiment of this compound is a peptide ranging from about 7 to 25 amino acids; wherein the peptide is selected from the group consisting of: a) Myelin proteolipid protein peptide; b) Moth cytochrome C peptide; c) tetanus toxin; d) HIV-1 GP 120 peptide; e) myelin basic protein; and f) HIV-1 GP 120 peptide; wherein the Myelin proteolipid protein peptide is selected from the group consisting of PLP peptide 139–151 and PLP peptide 190–209, the Moth cytochrome C peptide is peptide MCC 94–103, the myelin basic protein peptide is MBP peptide 1–11, and the tetanus toxin peptide is selected from the group consisting of tetanus toxoid peptide and P2 tetanus toxoid peptide.

Another embodiment of this compound is where the naturally occurring receptor is a T cell surface receptor; and the T cell surface receptor is selected from the group consisting of TCR/C3, CD4, CD8, CD10, CD26, CD28, and CD45.

Another aspect of this invention is a compound, having the structure as shown in FIG. 1R, wherein D is, independently, selected From the group consisting of NH and $NH_2$, wherein N represents any isotope of nitrogen, wherein H represents any isotope of hydrogen; "~" is, independently, selected from the group consisting of a single bond and a double bond; B represents, independently, any isotope of boron; A1 is, independently, selected from the group consisting of a C, a CX moiety and an N, wherein C represents any isotope of carbon, wherein X represents any atom capable of forming a single bond with C; each A2, A3, and A4 are, independently, selected from the group consisting of a CX moiety, a CXZ moiety, a CZ moiety, an NX moiety, and an O, wherein X and Z, independently, are selected from the group consisting of any atom capable of forming a single bond and any atom capable of forming a double bond with C or N and wherein O represents any isotope of oxygen; wherein each Y1 and Y2 are, independently, selected from the group consisting of a hydroxyl moiety and any reactive moiety that converts to a hydroxyl moiety under physiologic conditions; n represents an integer between 1 and 200, inclusive; wherein E1 and E3 are distinct reactive species in which: (a) R and R' are the remainder of the molecules not relevant to this reaction; (b) E1 is attached to R' by a covalent bond which are together designated as E1-R' or R'-E1; (c) E3 is attached to R by a covalent bond which are together designated as E3-R or R-E3; (d) R' represents the part of E1-R' not undergoing a chemical reaction; (e) R represents the part of R-E3 not undergoing a chemical reaction; (f) E1 undergoes a chemical reaction with E3 to form the product E1'-E3' and a byproduct F, wherein F is selected from the group consisting of $2H^+$ and $2e^-$, $H_2O$, and any other byproduct; (g) where $H^+$ is the cation of any isotope of hydrogen and $e^-$ is an electron; (h) here H represents any isotope of hydrogen and O represents any isotope of oxygen; (i) where E1' and E3' are covalently bonded; (j) E1 does not undergo a chemical reaction with another E1; (k) E3 does not undergo a chemical reaction with another E3; and (l) E1 and E3 are selected from the group consisting of a carboxylate, amino, imidazole, sulfhydryl, aldehyde, ester, and any other reactive species; wherein $[J]_p$, E2, $[I]_q$ and $[G]_m$ together are a linker moiety, and wherein $[G]_m$, $[J]_p$, and $[I]_q$ represent, independently, linker molecules (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous; and wherein m, p, and q represent, independently, an integer from 1 to 50, inclusive; and wherein E2 is selected from the group consisting of CX, CH, N, PhYZ, PhU, and any other moiety capable of forming covalent bonds with $[J]_p$, $[G]_m$, and $[I]_q$ and wherein: (a) C is any isotope of carbon; (b) X is any isotope of any atom capable of forming a single bond with carbon; (c) H is any isotope of hydrogen; (d) N is any isotope of nitrogen; (e) Ph is any isotope of phosphorous; (f) Y is any isotope of any atom capable of forming a single bond with phosphorous; (g) Z is any isotope of any atom capable of forming a single bond with phosphorous; and (h) U is any isotope of any atom capable of forming a double bond with phosphorous;

An embodiment of this compound includes the structures as shown in FIG. 1U and FIG. 1V which represent, independently, a binding moiety, wherein R represents the remainder of the molecule.

Another embodiment of the compound shown in FIG. 1R is wherein (a) $[G]_m$ is the side chain of a D- or L-isomer of lysine, cysteine, glutamic acid, aspartic acid, histidine, arginine, glutamine, and asparagine; (b) E2 is D- or L-isomer of lysine, cysteine, glutamic acid, aspartic acid, histidine, arginine, glutamine, and asparagine; (c) E1 and E3 are selected from the group consisting of an amino moiety and a carboxylic acid moiety; and (d) E1 and E3 are distinct from each other.

Yet another embodiment of the compound shown in FIG. 1R is wherein (a) $[G]_m$ is the side chain of a D- or L-isomer of lysine, cysteine, glutamic acid, aspartic acid, histidine, arginine, glutamine, and asparagine; (b) E2 is selected from the group consisting of 2-carboxybutyl, 2-carboxypropyl, 2-aminobutyl, 2-aminopropyl, and a hydrocarbon chain with an amino or carboxy side chain; (c) $[J]_p$ and $[I]_q$ represent, independently, hydrocarbon chains; (d) E1 and E3 are selected from the group consisting of an amino moiety and a carboxylic acid moiety; and (e) E1 and E3 are distinct from each other.

The compounds of the invention, in particular the comodimetric complexes, can be used to stimulate activation or proliferation of human CD26-bearing lymphocytes, by contacting the lymphocytes with a proliferation or activation-inducing concentration of the compound.

The method preferably involves in vivo administration of the compound, admixed with a pharmaceutically acceptable carrier such as pharmaceutical, sterile saline. The patient can be any patient who suffers from a disease state characterized by inadequate lymphocyte activation or concentration. Examples of such diseases are HIV infection, kidney failure, cancer (in particular, cancer accompanied by lymphocyte-depleting chemotherapy), and bone marrow disorders which result in depleted lymphocyte populations in the patient. The compound is preferably administered to the patient orally. The compounds can also be used to stimulate proliferation or activation of lymphocytes in vitro, e.g., where a patient's atologous lymphocytes are removed, stimulated to increase activation and/or number, and reinfused into the patient. This method can be used, for example, to increase the number of cytolytic T cells specific for a patient's tumor.

The above-described compounds are useful for crosslinking molecules on the same or different cells that are involved in immune system modulation. Compounds of the invention fall within the following genus:

(I)

wherein $P^1$ represents a first targeting moiety, preferably a peptide that can mimic the substrate binding site of a protease (preferably a serine protease or cysteine protease) that is expressed on the surface of the cell involved in immune system modulation (e.g., a T cell, a B cell, a stem cell, a bone marrow cell, including an antigen presenting cell);

$R^1$ represents a reactive group that reacts with a functional group in a reactive center of the protease;

$P^2$ represents a second targeting moiety, preferably a peptide, that may be the same or different from the first targeting moiety;

$R^2$ represents a second reactive group that may be the same or different from the first reactive group;

m=0 or 1 and n is a whole number from 1 to 10.

Thus, $P^1$ can be D1~A1~A2~A3~A4 or D2~A5~A6~A7~A8 as described above. In important embodiments of the invention, $P^1$ is a peptide or a peptidomimetic.

In certain embodiments of the invention, if $P^2=P^1$, then $R^2$ can be absent, the same, or different from $R^1$. In general, n is 1 and the compounds of the invention are referred to as homodimers (i.e., $P^2=P^1$) or heterodimers (i.e., $P^2 \neq P^1$).

Cells which are involved in immune system modulation are blood cells including T cells, B cells, stem cells, bone marrow cells, dendritic cells, and antigen presenting cells. The $P^1$ targeting moiety can have a carboxyl terminal portion containing 1, 2, 3, or 4 amino acids which mimic the substrate binding site of the protease. Exemplary proteases which are believed to be expressed on the surface of such cells and which are bound by the $P^1$ targeting moieties include post-prolyl cleaving enzymes, trypsin, chymotrypsin and elastase. The particular amino acids in the naturally occurring substrates of these enzymes are well known in the art and are identified below.

In general, the compounds of the invention contain from 1 to 30 amino acid residues (preferably the L isomers) and, more preferably, contain from 1 to 20 amino acid residues. In the most preferred embodiments, the $P^1$ targeting moieties contain from 1 to 10 amino acids, most preferably, from 1 to 2 amino acids. The $P^1$ targeting moiety can contain L or D amino acids; however, it is preferred that at least the amino acids which mimic the substrate binding site be in the L configuration. In contrast, the amino acids which are in a retroinverso configuration (see the Examples) preferably are in the D configuration.

The composition of the $P^1$ targeting moiety is not limited to amino acids but may include, in whole or in part, non-amino acid components, provided that such components do not interfere significantly (i.e., do not lower the Ki of the compound to less than about $10^{-7}$ M with the site-specific recognition of the compound by the protease and provided that the non-amino acid components do not interfere with the formation of a complex between the compound and the protease. In certain embodiments, the portion of the $P^1$ targeting moiety that is involved in binding to the substrate binding site is formed of amino acids and the remaining portion of the $P^1$ targeting moiety is formed of non-amino acid components. In general, any portion of the $P^1$ targeting moiety can be modified, for example, to be coupled to a detectable reagent, or immobilized to a surface via a linker, provided that such modifications satisfy the foregoing inhibition constant and complex formation criteria.

Peptides which reportedly have demonstrated utility for inhibiting post-prolyl cleaving enzymes and which, if coupled to a reactive group, form a covalent complex with a functional group in the reactive site of a post-prolyl cleaving enzyme are described in U.S. Pat. No. 4,935,493, "Protease Inhibitors", issued to Bachovchin et al. ("Bachovchin '493"); U.S. Pat. No. 5,462,928, "Inhibitors of Dipeptidyl-aminopeptidase Type IV", issued to Bachovchin et al. ("Bachovchin '928"); U.S. Pat. No. 5,543,396, "Proline Phosphonate Derivatives", issued to Powers et al., ("Powers '396"); U.S. Pat. No. 5,296,604, "Proline Derivatives and Compositions for Their Use as Inhibitors of HIV Protease", issued to Hanko et al., ("Hanko '604"); PCT/US92/09845, "Method for Making a Prolineboronate Ester", and its U.S. priority applications (U.S. Ser. Nos. 07/796,148 and 07/936,198), Applicant Boehringer Ingelheim Pharmaceuticals, Inc. ("Boehringer"); and PCT/GB94/02615, "DP-IV-Serine Protease Inhibitors", Applicant Ferring V. V. ("Ferring").

In important embodiments, the $P^1$ targeting moiety mimics the substrate binding site of the post-prolyl cleaving enzyme DP IV (also referred to herein as "CD 26"). DP IV is a post-prolyl cleaving enzyme with a specificity for removing Xaa-Pro (where Xaa represents any amino acid) dipeptides from the amino terminus of a polypeptide substrate. Representative structures of transition-state analog-based inhibitors Xaa-boroPro, include Lys-BoroPro, Pro-BoroPro and Ala-BoroPro in which "boroPro" refers to the analog of proline in which the carboxylate group (COOH) is replaced with a boronyl group (B)(OH$_2$). Alternative crosslinking compounds of the invention have an analogous structure in which the boronyl group is replaced by a phosphonate or a fluoroalkylketone (described below).

The invention also embraces compounds which mimic the substrate binding site of other post-prolyl cleaving enzymes. For Example, IgA 1 proteases recognize the cleavage site Ser-Thr-Pro-Pro-X (SEQ ID NO.6), (where X is any amino acid). Accordingly, Ser-Thr-Pro-Pro-R$^1$ (SEQ ID NO.7), is suitable for selectively binding to, and forming a complex with a functional group in the active site of an IgA 1 protease. The Ser-Thr in this targeting moiety may be readily substituted with any of the 20 naturally occurring amino acids, most preferably those having non-bulky side groups, such as Ala and Gly. It also is possible to substitute non-naturally occurring amino acids, such as 2-azetidinecarboxylic acid or pipecolic acid (which have 6-membered, and 4-membered ring structures respectively) for either of the Pro residues. Those skilled in the art will recognize that there are other such changes which can be made without significantly affecting the binding and complex forming character of these compounds.

In the case of IgA 2, protease, the cleavage site in the natural substrate is Pro-Thr-Pro-X (SEQ ID NO.8), with hydrolysis occurring between Pro and X. Thus, a preferred $P^1R^1$ binding moiety for binding to an IgA 2 protease has the formula Pro-Thr-Pro-$R^1$ (SEQ ID NO.9). Thr can be substituted by any of the naturally occurring amino acids, especially ones having non-bulky side groups, such as Ala, Gly or Ser. Other examples of post-prolyl cleaving enzymes which can be targeted by the targeting moieties of the invention include other IgA enzymes, encephalon degrading enzymes, vasopressin degrading enzymes, and oxytocin degrading enzymes.

The $P^1$ targeting moieties of the invention can be designed to mimic the substrate binding sites of other, non-post-prolyl cleaving enzymes that may be expressed on the surface of cells involved in immune system modulation. These enzymes include, for example, cysteine proteases and serine proteases such as trypsin, chymotrypsin and elastase. The substrate binding sites for these enzymes are well known and peptidomimetics for targeting binding to these sites have been reported. For example, a $P^1$ targeting moiety of the invention which mimics the substrate binding site of trypsin would include an arginine (Arg) or lysine (Lys) residue at its carboxyl-terminus with the carboxyl group of the Arg or Lys coupled to an appropriate reactive center, $R^1$, to form a covalent bond with a functional group in the active site of trypsin. Exemplary borolysine targeting moieties that can be used to form the compounds of the invention are described in U.S. Pat. Nos. 5,187,157 and 5,242,904, "Peptide Boronic Acid Inhibitors of Trypsin-like Proteases", issued to Kettner et al. ("Kettner '157" and Kettner U.S. Pat. No. '5,242,904) and in U.S. Pat. No. 5,288,707, "Borolysine Peptidomimetics", issued to Mettemich ("Mettemich"). Intermediates that are useful for preparing these inhibitors and related procedures are described in U.S. Pat. No. 5,250,720, "Intermediates for Preparing Peptide Boronic Acid Inhibitors of Trypsin-like Proteases" ("Kettner '720") and U.S. Pat. No. 5,384,410, "Removal of Boronic Acid Protecting Groups by Transesterification" ("Kettner '410").

$P^1$ targeting moieties also can be designed to mimic the substrate binding site of chymotrypsin. Such targeting moieties include a carboxyl terminal amino acid residue that is selected from the group consisting of phenylalanine (Phe), tryptophan (Trp), and tyrosine (Tyr). Preferably, the carboxyl groups of these amino acids are covalently coupled to an $R^1$ reactive group to form a binding moiety that selectively binds to, and forms a covalent complex with, a functional group in the active site of chymotrypsin. Yet other $P^1$ targeting moieties of the invention can be designed which mimic the substrate binding site of an elastase. For example, a $P^1$ targeting moiety which mimics the substrate binding site of an elastase would include a carboxyl terminal amino acid residue that is alanine (Ala) or glycine (Gly) with the carboxyl group of these amino acids covalently coupled to the reactive group $R^1$. In general, convention chemical reactions can be used to form the foregoing $P^1R^1$ binding moieties. Thus, $P^1R^1$ binding moieties of the invention can be designed and constructed to mimic the substrate binding site of virtually any protease for which the natural substrate is known or can be identified.

The development of phage display libraries and chemical combinatorial libraries from which synthetic compounds can be selected which mimic the substrate binding site of a protease permits the identification of further $P^1$ targeting moieties to which an $R^1$ reactive group can be covalently attached to form a binding moiety which mimics the substrate binding site of the protease and which forms a complex with a functional group in the protease reactive site. Such libraries can be screened to identify non-naturally occurring putative targeting moieties by assaying protease cleavage activity in the presence and absence of the putative phage display library molecule or combinatorial library molecule and determining whether the molecule inhibits cleavage by the protease of its natural substrate or of a substrate analog (e.g., a chromophoric substrate analog which is easily detectable in a spectrophotometric assay). Those phage library and/or combinatorial library molecules which exhibit inhibition of the protease then can be covalently coupled to the reactive groups $R^1$ disclosed herein and again tested to determine whether these novel molecules selectively bind to the protease (e.g., by repeating the above-noted screening assay). In this manner, a simple, high-through-put screening assay is provided for identifying non-naturally occurring targeting moieties of the invention.

In general, the first targeting moieties of the invention are covalently coupled via a carboxyl group at their carboxyl terminal amino acid to a first reactive group, $R^1$. As used herein, $R^1$ refers to a reactive group that is capable of reacting with a functional group in a reactive center of a protease expressed on the surface of a cell involved in immune system modulation. By reacting with a reactive center of the target protease, it is meant that the $R^1$ forms a covalent bond with a functional group that is located in the active site. $R^1$ reactive groups that are embraced within the invention include the reactive groups referred to as group "T" in U.S. Pat. No. 4,935,493, "Protease Inhibitors", issued to Bachovchin, et al. These include boronate groups, phosphonate groups, and fluoroalkylketone groups. The boronate groups are described in the detailed description of the invention and in the Examples. The phosphonate and fluoroalkylketone groups are described below. In general, it is preferred that the linkage between the carboxyl terminus of the targeting moiety and the reactive group be in an L configuration. It is preferred that the reactive group forms a covalent band with a functional group in the active site; however, there is no requirement for covalent bond formation in order to form a complex between the binding moiety and the active site.

The reactive groups of the invention that are phosphonate groups have the formula:

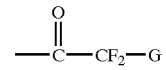

where G is either H, F or an alkyl group containing 1 to about 20 carbon atoms and optional heteroatoms which can be N, S, or O. Additional exemplary proline phosphonate derivatives which contain a perfluoroalkyl group, a phenyl group or a substituted phenyl group and which can be used in accordance with the methods of the invention are those described in U.S. Pat. No. 5,543,396 (Powers '396).

As used herein, the reactive groups of the invention that are fluoroalkylketone reactive groups have the formula:

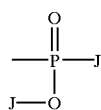

where each J, independently, is O-alkyl, N-alkyl, or alkyl (each containing about 1–20 carbon atoms) and, optionally, heteroatoms which can be n=N, S, or O. Other ketoamides, ketoacids and ketoesters that are useful reactive groups for reacting with the reactive center of a protease (e.g., a serine protease or a cysteine protease) are described in PCT/US91/09801, "Peptides, Ketoamides, Ketoacids, and Ketoesters", Applicant: Georgia Tech Research Corp. ("GA Tech") which claims priority to U.S. Pat. No. 635,287, filed Dec. 28, 1990.

In certain embodiments, the reactive groups are selected from the groups having the formulas

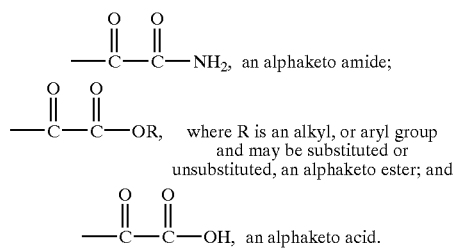

The second targeting moiety, $P^2$, binds to a molecule that is present on the surface of the same or different cell to which the first targeting moiety binds. Preferably, the second targeting moiety binds to a molecule (e.g., a receptor, a major histocompatibility complex (MHC) molecule) which is present on the surface of a T cell or on the surface of a B cell. In certain embodiments, the second targeting moiety has a structure which mimics the substrate binding site of a protease that is present on a cell that is involved in immune system modulation. Thus, the second targeting moiety may be the same as the first targeting moiety, and the compounds of the invention are useful for crosslinking proteases that have the same or a similar substrate specificity on the same or different cells. For example, the compounds of the invention can be used to crosslink a first protease (e.g., a post-prolyl cleaving enzyme) on a first cell and a different protease (e.g., a trypsin, chymotrypsin, elastase or other serine protease or cysteine protease) that is expressed on the surface of the same or on a different second cell. In certain preferred embodiments, the first and second targeting moieties are identical (i.e., $P^2=P^1$) and the second reactive group $R^2$ may be absent (i.e., m=0), the same or different from the first reactive group $R^1$ (i.e., $R^1 \neq R^2$). Such compounds are referred to as "homodimers". In yet other embodiments, the first and second targeting moieties are different and these compounds are referred to as "heterodimers".

In yet other embodiments, the second targeting moiety is an antigen that selectively binds to an MHC molecule on the surface of an antigen presenting cell. Such embodiments of the invention are useful as vaccines for inducing an immune system response to the antigen. In particular, such compounds are useful for inducing an immune system response to antigens that exhibit relatively low immunogenicity using conventional vaccine preparations. Accordingly, the invention also provides for an improved vaccine and related methods for inducing an immune response to an antigen. Examples of antigens are antigens characteristic of pathogens, cancer antigens, and allergans.

In alternative embodiments, the second targeting moiety is a ligand that selectively binds to a receptor that is expressed on the surface of the cell (preferably a T cell or a B cell). Exemplary receptors which have naturally occurring ligands that can be mimicked by the second targeting moieties of the invention include receptors selected from the following group: TCR/C3, CD4, CD8, CD 10, CD26, CD28 and CD45. According to yet other embodiments, the second targeting moiety is an antibody or antibody fragment that selectively binds to an epitope expressed on the cell surface. The epitope can be a portion of any of the foregoing receptors.

Regardless of the nature of the second targeting moiety target (e.g., protease, receptor, MHC complex, epitope), phage display and other types of combinatorial libraries can be screened in a manner analogous to that described above to identify non-naturally occurring targeting moieties that are useful in forming the compounds of the invention.

There is no requirement that the second targeting moiety be covalently attached to a second reactive group. For example, the second targeting moiety may have sufficient affinity for its binding partner (e.g., an MHC molecule) to permit cross linking between the same or different target molecules on the same or different cells without forming a covalent complex between the second targeting moiety and its targeted binding partner. There also is no requirement that the second reactive group be the same as the first reactive group. Thus, for example, the compounds of the invention embrace molecules that include a first binding moiety which contains a first reactive group $R^1$ that is a boronate and a second binding moiety which contains a second reactive group that is a boronate, a phosphonate or a trifluoroalkylketone group.

A linker is covalently coupled to the first and second targeting moieties, $P^1$ and $P^2$, in a manner that does not adversely affect the ability of these moieties to bind to their respective targeted binding partners. Exemplary linkers, including a description of linker composition, size, and procedures for coupling the linker to the targeting moieties are described in the detailed description of the invention and in the Examples. In general, such linkers are commercially available and are coupled to the targeting moieties using conventional coupling procedures which are well known to those of ordinary skill in the art.

Certain aspects and uses of the invention are based on the discovery that certain homodimers are capable of stimulating T cells and that this stimulatory ability is, at least in part, dependent upon the length of the linker. Applicant also has discovered that there exists a length between binding moieties (about 20 angstroms) below which this homodimer is no longer capable of stimulating T cells. The ability of any type of homodimer for crosslinking DP IV proteases to stimulate T cells is unexpected in view of published reports that such DP IV homodimers exhibit a T cell inhibitory activity. (See, e.g., PCT/GB94/02615, "DP-IV-Serine Protease Inhibitors", Applicant Ferring V. V. ("Ferring") and the U.S. patent application which claims priority to Ferring). Thus, the invention provides a new use for the homodimer DP-IV inhibitors disclosed in Ferring, namely, the use of the Ferring homodimers for stimulating T cells in a patient in need of such treatment. Ferring describes symmetric homodimers containing two active-site directed inhibitors of DP-IV linked via the side chains of their amino acid residues.

Certain concentrations of the homodimers of the invention have been found to stimulate blood cells. The compounds of the invention are particularly useful for treating HIV+ patients, for example, by contacting the T cells obtained from an HIV+ patient with a therapeutically effective amount of one or more compounds of the invention under conditions that permit blood cell activation. The stimulatory effect on blood cells of these compounds at stimulating concentrations is illustrated in the accompanying Examples. The cells can be contacted with the crosslinking compounds in vivo or ex vivo. This stimulatory property of the homodimer compounds of the invention is unexpected and could not have been predicted based upon the reported inhibitory effect on the immune system of certain monomers (e.g., the compounds disclosed in Bachovchin '493) and certain homodimers (e.g., PCT/GB94102615, "DP-IV-Serine Protease Inhibitors", Applicant Ferring V. V. ("Ferring").

The compounds of the invention can be used to inhibit the enzymatic activity of the proteases to which the targeting moieties selectively bind. Thus, the compounds of the invention are useful for inhibiting post-prolyl cleaving enzymes, as well as for inhibiting other serine and cysteine proteases (e.g., chymotrypsin, trypsin, and elastase).

According to another aspect of the invention, methods are provided for modulating immune system function. The compounds of the invention are administered to subjects in need of immune system modulation in amounts effective to modulate immune system function. Modulation of immune system function includes, but is not limited to, increasing immune function such as by stimulating proliferation and specific immune function of blood cells nonspecifically or by specifically stimulating T and/or B cells and/or bone marrow cells, stem cells, early lineage progenitor cells to produce a prophylactic or therapeutic result relating to infectious disease, cancer, and the like. Specifically included is the use of the compounds of the invention, and in particular, homodimers for the treatment of disorders characterized by reduced T cell levels in vivo, e.g., HIV and other disorders associated with a compromised immune system. Modulation of immune system function also includes, but is not limited to, decreasing immune function such as by suppressing generally the immune system in transplant recipients or suppressing specifically the immune system to treat autoimmune disease, allergy and the like. In one important embodiment the homodimers of the invention are used to stimulate blood cell proliferation, as described in detail below. Specific conditions that may be treated according to the invention are deemed specific independent aspects of the invention and are described in detail in the tables and examples below.

According to still another aspect of the invention, the above crosslinking compounds are used in the preparation of medicaments, for treating the conditions described herein.

According to yet another aspect of the invention, a method for stimulating T cells is provided. A crosslinking compound of the invention is contacted with the T cells of a subject in need of such treatment in an amount effective to stimulate T cells. The crosslinking compounds that are particularly useful for stimulating T cells are those compounds which crosslink DP IV molecules as described above, including the preferred crosslinking compounds. As noted above, the preferred crosslinking compounds include a linker, L which when positioned between binding moieties results in a minimum length of about 20 angstroms between these moieties. Preferably, the distance between binding moieties is from 20 to 60 angstroms, more preferably from 30 to 50 angstroms.

According to still another aspect of the invention, pharmaceutical preparations are provided. The pharmaceutical preparations contain a crosslinking compound as described above and, optionally, a pharmaceutically-acceptable carrier. Preferably, the pharmaceutical compositions are sterile. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. The pharmaceutical compositions also may contain, optionally, suitable preservatives, such as: benzalkonium chloride; chlorobutanol; parabens and thimerosal. Compositions suitable for parenteral administration conveniently comprise a sterile aqueous preparation of the crosslinking compound, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available for treating a subject. The particular mode of delivery selected will depend, of course, upon the particular crosslinking compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. Such modes of administration also include obtaining T cells or bone marrow cells, stem cells or early lineage progenitor cells from a patient and contacting the isolated cells with the crosslinking compounds of the invention ex vivo, followed by reintroducing the treated cells to the patient. The treated cells can be reintroduced to the patient in any manner known in the art for administering viable cells.

As used herein, the term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred for prophylactic and other treatment because of the convenience to the patient as well as the dosing schedule.

The pharmaceutical compositions may conveniently be presented in unit dosage form and may be prepared by any of the methods well-known in the art of pharmacy. The methods include the step of bringing the crosslinking compounds of the invention into association with a carrier which constitutes one or more accessory ingredients. In general, the compositions are prepared by uniformly and intimately bringing the crosslinking compounds into association with a liquid carrier, a finely divided solid carrier, or both, and then, if necessary, shaping the product.

Compositions suitable for oral administration may be presented as discrete units, such as capsules, tablets, lozenges, each containing a predetermined amount of the crosslinking compound of the invention. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the crosslinking compounds described above, increasing convenience to the subject and the physician. Many types of release delivery systems are available and known to those of ordinary skill in the art.

They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the crosslinking compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 10 days, and preferably 60 days. Long-term sustained release implants are well-known to those of ordinary skill in the art and include some of the release systems described above.

The crosslinking compounds described herein are administered in effective amounts. An effective amount is a dosage of the crosslinking compound sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, an effective amount for stimulating T cell activation would be an amount sufficient to increase to a statistically significant extent T cell activation as for example, measured by proliferation or by increased T cell activity. An effective amount for stimulating a desired immune response also can be measured, for example, by determining a change in the immune function in a subject (e.g., increased B cell response, increased cytotoxic T cell response, stimulation of bone marrow proliferation, or an ability to slow, halt, or prevent an infection or cancer). An effective amount for treating an autoimmune disorder or allergic disorder would be that amount sufficient to lessen or inhibit altogether the immune or allergic response associated with the disorder so as to slow or halt the development of or the progression of the disorder. Thus, it will be understood that the crosslinking compounds of the invention can be used to treat an autoimmune disorder (e.g., transplant rejection) prophylactically in subjects at risk of developing an immune response (e.g., recipients prior to transplant). As used in the claims, "inhibit" embraces all of the foregoing. Likewise, an effective amount for treating an immune system disorder is that amount which can slow or halt altogether the symptoms associated with the immune system disorder so as to prevent the disorder, slow its progression, or halt the progression of the immune system disorder. It is preferred generally that a maximum dose be used, that is, the highest safe dose according to sound medical judgment.

Generally, doses of active compounds will be from about 0.001 mg/kg per day to 1000 mg/kg per day. It is expected that doses range of 0.01 to 100 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

As used herein, crosslinking compound means the compounds described above as well as salts thereof.

These and other aspects of the invention will be described in greater detail below.

All patents, patent applications, references and other documents that are identified in this patent application are incorporated in their entirety herein by reference.

Definitions

By "amino acid" is meant to include amino acid.

By "boroPro" is meant an alpha-amino boronic acid analog of proline bonded to an amino acid to form a dipeptide with boroPro as the C-terminal residue. "BoroPro" is used to designate such an analog having the carboxyl group of proline replaced with a $B(OH)_2$ group, where $(OH)_2$ represents two hydroxyl groups and B represents boron.

By Xaa is meant any amino acid residue, e.g., a lysine residue.

Also, for this invention, "[Lysine-boroProline]$_2$" and "KbP-S-KbP, where S represents a linker spacer" are used interchangeably. "Dimeric KbP with adipic acid as the spacer linker," "(di(L-Lysine-L-boroProline)adipate," and "KbP$_2$-Adipate" are used interchangeably. Dimeric and bivalent are used interchangeably.

Linker-spacer molecule, cross-linker, cross-linker molecule, linker molecule and linker group are used interchangeably.

By "agonist" is meant a molecule or compound which activates the signaling pathway in question.

By "antagonist" is meant a molecule or compound which inhibits the signaling pathway in question.

"CD26 ligand" is any protein, glycoprotein, lipoprotein or polypeptide that binds to the T cell receptor CD26 and may provide a stimulatory or inhibitory signal.

CD26, Dipeptidyl Peptidase IV (DP IV) and dipeptidyl aminopeptidase IV are used interchangeably. CD26 is a postproline cleaving enzyme with a specificity for removing Xaa-Pro (where Xaa represents any amino acid) dipeptides from the amino terminus of polypeptides.

"CD26-specific binding species" means a CD26-specific antibody, fragment or small molecular weight compound that binds to CD26.

"Tethered or coupled α-amino acid" is an α-amino acid with a carbon atom of its side chain tethered, linked or coupled to the N atom of the α-amino group.

By alpha-carbon of an amino acid is the one to which the carboxylic acid group is attached.

By alpha-amino acids is where the amino group is attached to the alpha-carbon. All naturally occurring amino acids are alpha-amino acids or alpha-imino, which means that the amino and carboxylic acid groups are both attached to the same carbon atom. Each amino acid can be thought of as a single carbon atom (the alpha carbon, C) to which there is attached one carboxyl group, one amino group, a side chain denoted R as shown below and a hydrogen.

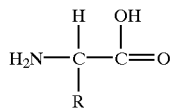

Wherein: "R" is a side chain; "NH$_2$" is the alpha amino group; the first carbon (C) attached to the NH$_2$ group having a hydrogen (H) and an R group attached is the alpha carbon; and the carbon double bonded to an oxygen and a hydroxyl group (OH) is the alpha carboxyl group.

The NH$_2$ and COOH groups are used to connect amino acids to one another. The hydroxyl group (OH) of one amino acid on the carboxyl end and the hydrogen (H) on the N terminus are removed (H$_2$O) when two amino acids are linked together. To form a protein, the amino group of one amino acid reacts with the carboxyl group of another by the elimination of water; the resulting chemical bond is called a peptide bond.

By "peptides" is meant a small molecule, e.g., usually containing less than 50 amino acid residues, which do not generally possess a well-defined three-dimensional structure.

By Å or "Angstrom" is meant $10^{-10}$ M. The relative bond size used in different peptides is as follows: N—H: 1.0 Å; C—H: 1.1 Å; C double bonded to O: 1.2 Å; N—CO: 1.3 Å; C—O: 1.4 Å; C—C: 1.5 Å; Alanine: 6 Å; Benzene: 6 Å; Water: 4 Å; and Phenylalanine: 7 Å.

Other features and advantages of the invention will be apparent from the following detailed description, and from the claims.

BRIEF DESCRIPTION OF THE DRAWINGS

FIGS. 1A–1V are diagrams showing the general structures of several preferred homobivalent and homomultivalent compounds or are diagrams of components needed for these structures:

FIG. 1A is a diagram of a general bivalent template with non-identical binding moieties.

FIG. 1B is a diagram of a general homobivalent template.

FIG. 1C is a diagram of a general bivalent template with amino linkages using a dicarbonyl linker.

FIG. 1J is a diagram of another bivalent example with carboxyl linkages using a 1,4-Diaminobutane linker.

FIG. 1K is a diagram of a general bivalent template with disulfide linkages using a dithiol linker.

FIG. 1N is a diagram of another bivalent example with disulfide linkages using a dithiothreitol linker [(Cysteine-boroProline)$_2$dithiotheitol].

FIG. 1P is a diagram of a general bivalent template with imidazol linkages using a dicarbonyl linker.

FIG. 1Q is a diagram of a bivalent example with imidazed linkages using an adipoyl linker: (Histidine-boroProline)$_2$Adipate.

FIG. 1R is a diagram of a general homofunctional polymeric crosslinker template.

FIG. 1S is a diagram of a homotrimeric example using adipoyl linkers.

FIG. 1V is a diagram of binding moiety containing A5, A6, A7, and A8 atoms.

FIG. 2A is a diagram of a general heterobivalent template.

FIG. 2B is a diagram of a heterobivalent example coupling a binding moiety to an MCC peptide (94–103).

FIG. 2C is a diagram of a heterobivalent example coupling a binding moiety to a PLP peptide (139–151).

FIG. 11D is a fluoroolefin isostere of Xaa-boroProline.

DETAILED DESCRIPTION

Figure 1D:
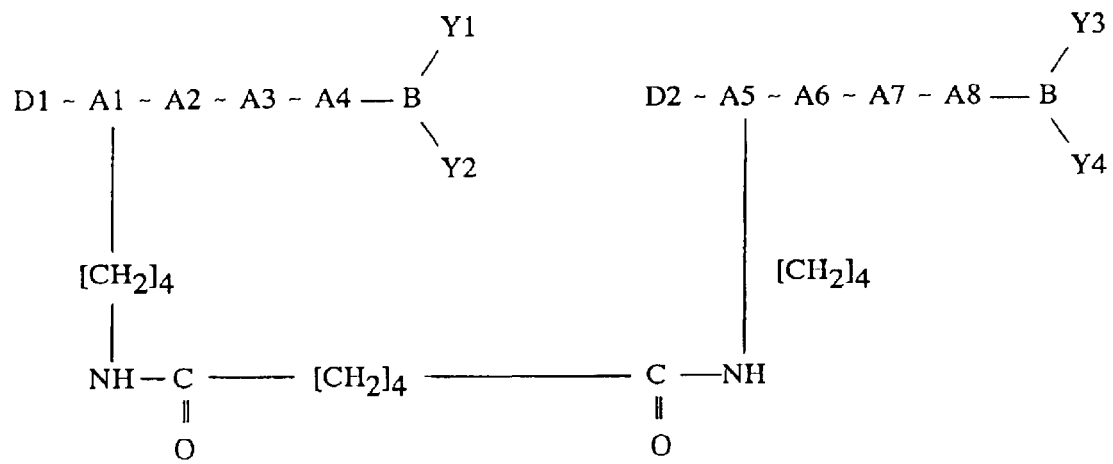
FIG. 1D is a diagram of a bivalent example with amino linkages using an adipoyl linker.

Synthetic, low molecular weight, bivalent and multivalent crosslinking compounds with agonistic activity are designed and developed. To have agonist activity, the molecule needs to be able to induce the association of receptors of a specific class in a manner similar to that induced by its natural ligand. These agonistic molecules therefore need to be at least bidentate. Additionally, the individual binding units must be properly spaced for the desired association to occur.

The homobivalent (homodimeric), homomultivalent and heterobivalent (heterodimeric) compounds of this invention represent a new class of biological modulators which can be used as therapeutic or diagnostic agents or both.

T Cell Surface Receptors

T cell surface receptors and their naturally occurring ligands are used herein as examples to demonstrate how different homobivalent, homomultivalent, and heterobivalent synthetic crosslinking compounds function; these examples are therefore not intended to limit the invention. The molecule, Xaa-boroPro, which has been shown to have high affinity for the CD26 T cell surface receptor (See above-discussion), can be a component molecule of the homobivalent, homomultivalent, or heterobivalent compounds outlined herein.

Biochemistry of CD26 T Cell Surface Receptor

CD26 is a highly glycosylated type two transmembrane protein. It exists as a dimer with a subunit molecular weight of about 110 kDa. The cDNAs encoding the human, mouse and rat proteins have been cloned and sequenced (D. Darmoul, M. Lacasa, L. Baricault, D. Marguet, C. Sapin, P. Trotot, A. Barbat, and G. Trugnan. "Dipeptidyl peptidase IV (CD26) gene expression in enterocyte-like colon cancer cell lines HT-29 and Caco-2: Cloning of the complete human coding sequence and changes of dipeptidyl peptidase IV mRNA levels during cell differentiation," *J. Biol. Chem.* 267, 4824–4833 (1992); D. Marguet, A. M. Bernard, I. Vivier, D. Darmoul, P. Naquet, and M. Pierres. "cDNA cloning for mouse thymocyte-activating molecule: A multifunctional ecto-dipeptidyl peptidase IV (CD26) included in a subgroup of serine protease," *Journal of Biological Chemistry* 267, 2200–2208 (1992); T. Tanaka, D. Camerini, B. Seed, Y. Torimoto, N. H. Fang, J. Kameoka, H. N. Dahlberg, S. F. Schlossman, and C. Morimoto. "Cloning and functional expression of the T cell activation antigen CD26," *Journal of Immunology* 149, 481–486 (1992); published erratum appears in *J. Immunol* 50(5):2090 (March 1993)). Human CD26 cDNA encodes a 766 amino acid polypeptide (having a molecular weight of 88,300) and the mouse cDNA encodes a 760 amino acid polypeptide (87,500 molecular weight). The sequences of the mouse, rat and human CD26 share up to 98% homology. Most of the CD26 molecule resides outside of the cell by being anchored to the cell plasma membrane through a 22 amino acid hydrophobic domain on the N terminus and only a small, six amino acid N terminal tail projects into the cytoplasm.

Among lymphoid cells, CD26 is found mainly on the surface of CD4+T cells where it is believed to have important roles in T cell activation pathways (see section on CD26 and T cell function below). CD26 is also found on a small fraction of CD8+cells. CD26 has been shown to be identical with an enzyme known as dipeptidyl peptidase amino peptidase Type IV (DP IV, sometimes also abbreviated DPP IV or DAP IV).

Enzymology of CD26: Active Site Structure and Inhibitor Design

The catalytic activity thus far identified for CD26 associated DP IV protease activity involves the cleaving of a dipeptide unit from the free amino terminus of polypeptides and proteins. DP IV shows a strong preference for cleaving after a proline residue, i.e., a proline in the penultimate position from the amino terminus. A free amino terminus appears to be a requirement but the enzyme displays little preference for any particular amino acid in this position (J. Heins, P. Welker, C. Schonlein, I. Born, B. Hartrodt, K. Neubert, D. Tsuru, and A. Barth, "Mechanism of proline-specific proteinases: (I) Substrate specificity of dipeptidyl peptidase IV from pig kidney and proline-specific endopeptidase from *Flavobacterium meningosepticum*," *Biochimica Et Biophysica Acta* 954, 161–169 (1988)). DP IV can regarded as a postproline cleaving aminopeptidase with a specificity for removing N-terminal Xaa-Pro dipeptides where Xaa can be any amino acid. However, DP IV will also remove amino terminal Xaa-Ala dipeptides, although much less effectively. The enzyme does, however, require that some amino acid be N terminal to proline because boroPro itself is not an effective inhibitor. The P2 residue is probably required only for presenting a free amino group in the appropriate geometrical arrangement with respect to the proline bond to be cleaved because the addition of a group to the P2 N terminus, such as Ac, CBZ, or Fmoc, abolishes the inhibitory potency (G. R. Flentke, E. Munoz, B. T. Huber, A. G. Plaut, C. A. Kettner, and W. W. Bachovchin. "Inhibition of dipeptidyl aminopeptidase IV (DP-IV) by Xaa-boroPro dipeptides and use of these inhibitors to examine the role of DP-IV in T-cell function," *Proceedings of the National Academy of Sciences of the United States of America* 88, 1556–1559 (1991)). This indicates that the active site is constructed to recognize a proline residue at P1 and a free amino group at P2. The P2 amino acid side chain is probably directed away from the enzyme and free in solution. P1 refers to the residue on the N-terminal side of the sessile bond. P2 refers to the residue on the N-terminal side of P1.

CD26 and T Cell Function

The work of Shon et al. was among the first to implicate DP IV as important to T cell function (E. Schon, I. Born, H. U. Demuth, J. Faust, K. Neubert, T. Steinmetzer, A. Barth, and S. Ansorge, "Dipeptidyl peptidase IV in the immune system. Effects of specific enzyme inhibitors on activity of dipeptidyl peptidase IV and proliferation of human lymphocytes," *Biological Chemistry Hoppe Seyler* 372, 305–311 (1991); E. Schon, H. W. Mansfeld, H. U. Demuth, A. Barth, and S. Ansorge, "The dipeptidyl peptidase IV, a membrane enzyme involved in the proliferation of T lymphocytes," *Biomedica Biochimica Acta* 44, (1985); E. Schon, E. Eichmann, R. Grunow, S. Jahn, S. T. Kiessig, H. D. Volk, and S. Ansorge, "Dipeptidyl peptidase IV in human T lymphocytes. An approach to the role of a membrane peptidase in the immune system," *Biomedica Biochimica Acta* 45, 1523–1528 (1986); E. Schon, S. Jahn, S. T. Kiessig, H. U. Demuth, K. Neubert, A. Barth, B. R. Von, and S. Ansorge, "The role of dipeptidyl peptidase IV in human T lymphocyte activation. Inhibitors and antibodies against dipeptidyl peptidase IV suppress lymphocyte proliferation and immunoglobulin synthesis in vitro," *European Journal of Immunology* 17, 1821–1826 (1987); E. Schon et al., "Dipeptidyl peptidase IV in human T lymphocytes. Impaired induction of interleukin 2 and gamma interferon due to specific inhibition of dipeptidyl peptidase IV," *Scandinavian Journal of Immunology* 29, 127–132 (1989)). This work reported that DP IV inhibitors and anti-DP IV polyclonal antibodies suppressed T cell activation in culture. It has been demonstrated that Pro-boroPro and Ala-boroPro inhibited an immune response in vivo in mice such that antibody production in response to an antigen challenge was reduced; this was direct evidence for a role for DP IV/CD26 in immune function in vivo.

Also, most of the evidence implicating CD26/DP IV as important to proper T cell function and immune system regulation comes from studies of the effects of various anti-CD26 mAbs on T cell functions. Because Abs are naturally bivalent, they are often able to mimic the natural ligand in inducing association of the receptor, e.g., an agonistic effect, which may be a dimerization or an aggregation. If an antibody fails to correctly mimic the natural-ligand induced association, it will then often block the interaction with the natural ligand and therefore show an inhibitory or antagonistic activity.

The anti-CD26 mAbs thus far identified have either activating, inhibitory, or both effects on various T cell responses. These results show that CD26 is an association-activated co-stimulatory T cell receptor.

The role for CD26 as an association-activated, co-stimulatory molecule has been recently confirmed in experiments in which the gene for CD26 was transfected into Jurkat T cell lines (T. Tanaka, D. Camerini, B. Seed, Y. Torimoto, N. H. Fang, J. Kameoka, H. N. Dahlberg, S. F. Schlossman, and C. Morimoto, "Cloning and functional expression of the T cell activation antigen CD26," published erratum appears in *J. Immunol,* 150(5):2090 (March 1993); *Journal of Immunology* 149, 481–486 (1992)).

The results indicated that mAb-mediated cross linking of CD26 on CD26+Jurkat cell resulted in enhanced $Ca^{2+}$ mobilization and IL-2 production in response to anti-CD3 suboptimal stimulation in the presence of phorbol esters. Untransfected Jurkat cells do not express CD26 and do not produce IL-2 in significant amounts in response to anti-CD26 costimulation with suboptimal anti-CD3 treatment in the presence of phorbol esters.

Mechanisms of CD26 Mediated Signal Transduction

CD26 has only a short six amino acid cytoplasmic tail. This argues against signal transduction via the cytosolic domain as is often the case for other cell surface receptors. CD26 may participate in T cell signal transduction through two hypothetical mechanisms: (1) through its association with other molecules in the membrane, and (2) through its DP IV protease activity.

EXAMPLE 1

General Synthesis of Homobivalent, Homomultivalent and Multivalent Crosslinking Compounds The synthesis of bivalent or multivalent compounds or agents outlined herein involves essentially very similar chemistry. These bivalent and multivalent compounds are designed such that they induce associations between naturally occurring receptors, e.g., an association between a T cell surface CD26 receptor with itself (homobivalent) or an association between three T cell surface CD26 receptors (homomultivalent, e.g., homotrivalent) or an association between CD26 receptor with the T cell receptor (TCR/CD3) or with the CD4 receptor (heterobivalent).

For the most part, straightforward peptide coupling chemistry is employed. The standard peptide coupling chemistry methods and procedures used in this invention are readily available. Examples of books using these methods include, but not limited to, the following citations incorporated herein by reference: P. D. Bailey, *An Introduction to Peptide Chemistry*, Ed.: John Wiley & Sons, 1990; Miklos Bodansky, *Peptide Chemistry, A Practical Textbook*, Ed.: Springer-Verlag, 1988; Miklos Bodansky, *Principles of Peptide Synthesis*, "Reactivity and Structure Concepts in Organic Chemistry," Volume 16, Ed.: Springer-Verlag, 1984; and Miklos Bodansky, *Principles of Peptide Synthesis*, "Reactivity and Structure Concepts in Organic Chemistry," Volume 21, Ed.: Springer-Verlag, 1984.

1. Homomultivalent Compounds: General Structure

The bivalent, homobivalent and homomultivalent compounds taught herein can either start with the general diagram for a bivalent template with non-identical binding moieties as shown in FIG. 1A or with the general diagram for a homobivalent template as shown in FIG. 1B.

Figure 1E:
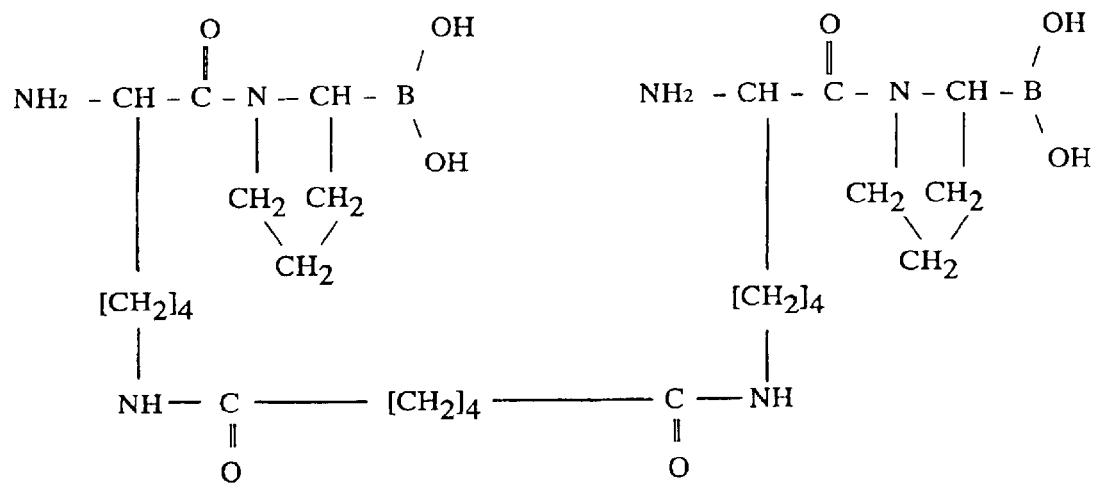
FIG. 1E is a diagram of a homobivalent example with amino linkages using an adipoyl linker [(Lysine-boroPro)$_2$Adipate].
Figure 1F:
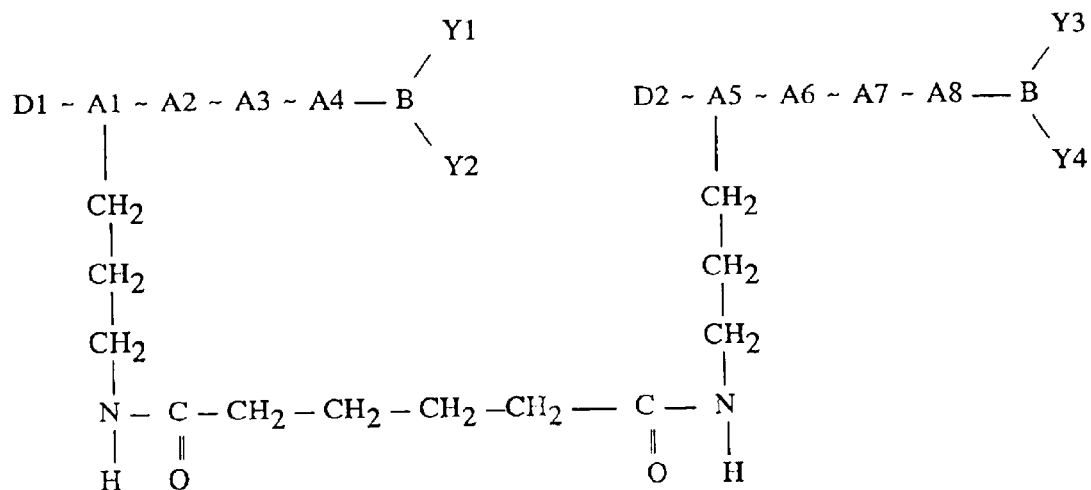
FIG. 1F is a diagram of another homobivalent example with amino linkages using an adipoyl linker.
Figure 1G:
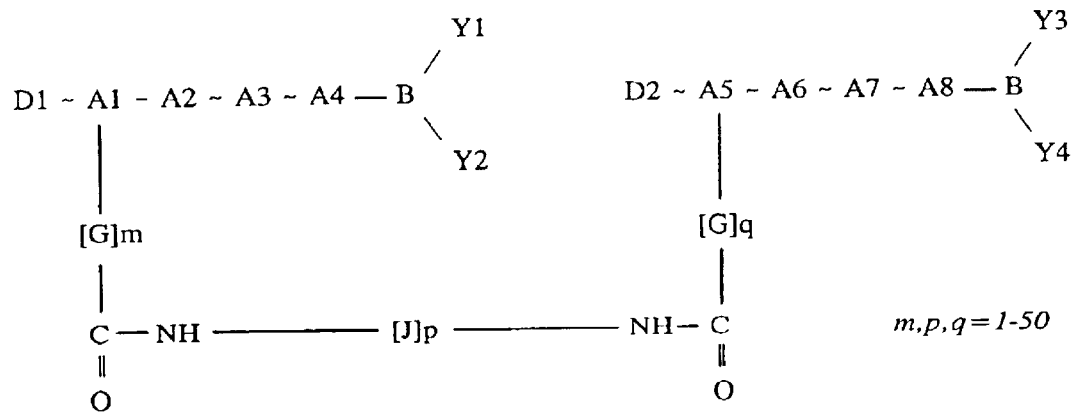
FIG. 1G is a diagram of a general bivalent template with a carboxyl linkage using a diamino linker.
Figure 1H:
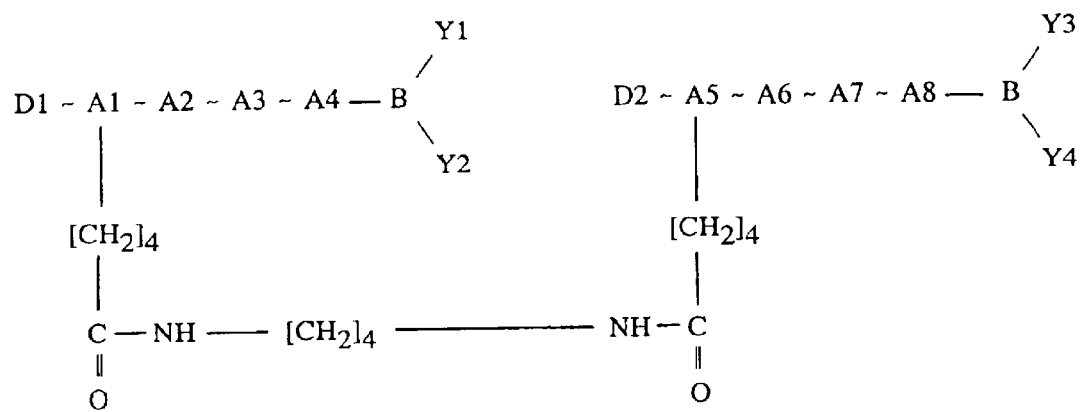
FIG. 1H is a diagram of a bivalent example with carboxyl linkages using a 1,4-Diaminobutane linker.
Figure 1I:
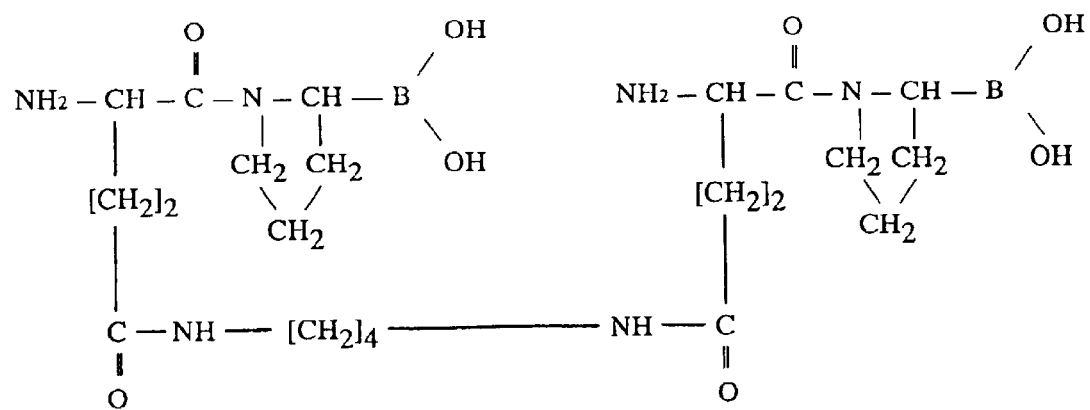
FIG. 1I is a diagram of a bivalent example with carboxyl linkages using a 1,4-Diaminobutane linker [(Aspartyl-boroProline)$_2$1,4-Diaminobutane].
Figure 1L:
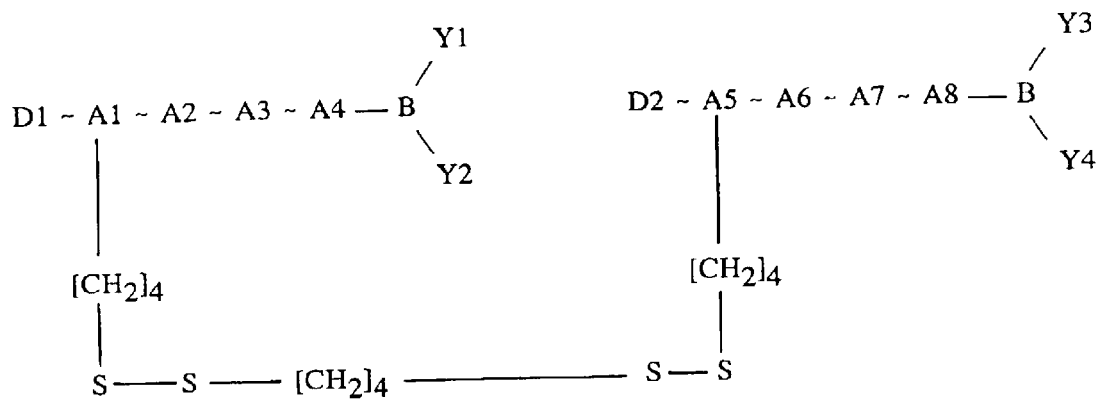
FIG. 1L is a diagram of a bivalent example with disulfide linkages using a 1,4-Dithiobutane linker.
Figure 1M:
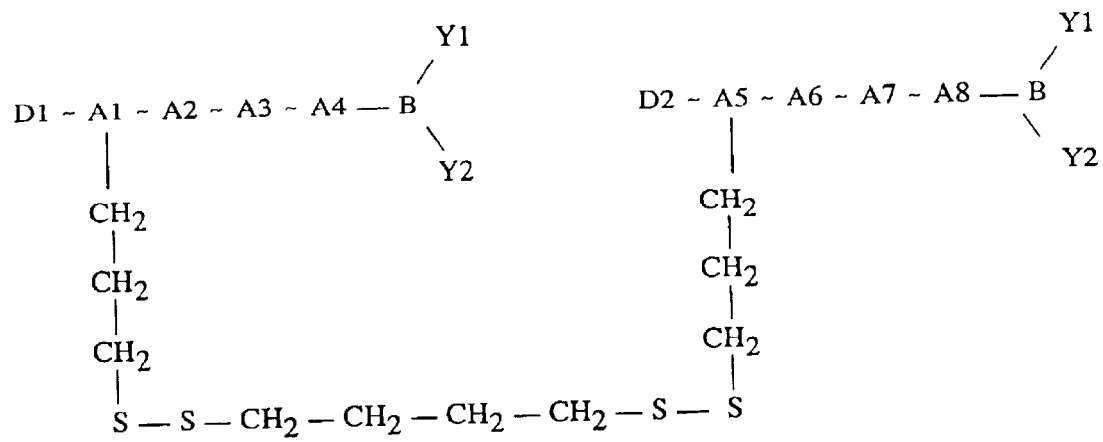
FIG. 1M is a diagram of another bivalent example with disulfide linkages using a 1,4-Dithiobutane linker.
Figure 1T:
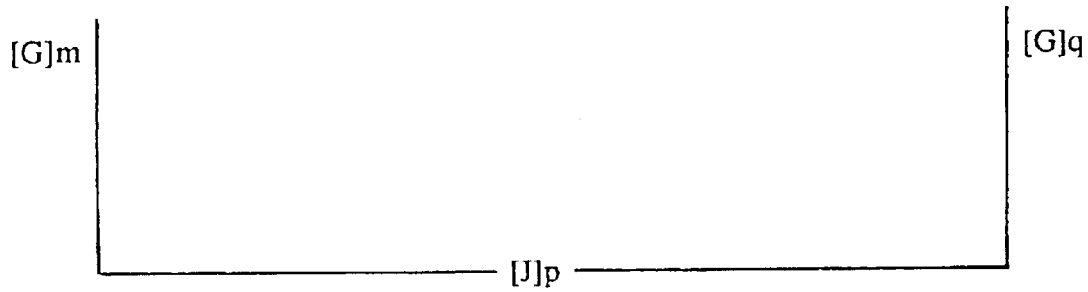
FIG. 1T is a diagram of a linker molecule template.

FIGS. 1C–1T are diagrams showing the structure of several preferred bivalent and multivalent compounds. FIG. 1C is a diagram of a general bivalent template with amino linkages using a dicarbonyl linker; FIG. 1D is a diagram of a bivalent example with amino linkages using an adipoyl linker; FIG. 1E is a diagram of a homobivalent example with amino linkages using an adipoyl linker [(Lysine-boroPro)$_2$Adipate]; FIG. 1F is a diagram of another homobivalent example with amino linkages using an adipoyl linker; FIG. 1G is a diagram of a general bivalent template with a carboxyl linkage using a diamino linker; FIG. 1H is a diagram of a bivalent example with carboxyl linkages using a 1,4-Diaminobutane linker; FIG. 1I is a diagram of a bivalent example with carboxyl linkages using a 1,4-Diaminobutane-linker [(Aspartyl-boroProline)$_2$1,4-Diaminobutane]; FIG. 1J is a diagram of another bivalent example with carboxyl linkages using a 1,4-Diaminobutane linker; FIG. 1K is a diagram of a general bivalent template with disulfide linkages using a dithiol linker; FIG. 1L is a diagram of a bivalent example with disulfide linkages using a 1,4-Dithiobutane linker; FIG. 1M is a diagram of another bivalent example with disulfide linkages using a 1,4-Dithiobutane linker; FIG. 1N is a diagram of another bivalent example with disulfide linkages using a dithiothreitol linker [(Cysteine-boroProline)$_2$dithiotheitol]; FIG. 1P is a diagram of a general bivalent template with imidazol linkages using a dicarbonyl linker; FIG. 1Q is a diagram of a bivalent example with imidazed linkages using an adipoyl linker: (Histidine-boroProline)$_2$Adipate; FIG. 1R is a diagram of a general homofunctional polymeric crosslinker template; FIG. 1S is a diagram of a homotrimeric example using adipoyl linkers; and FIG. 1T is a diagram of a linker molecule template.

Figure 1U:
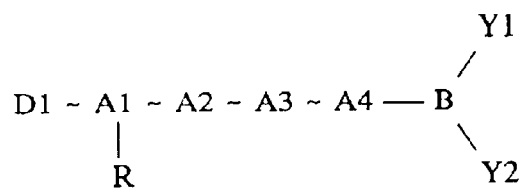
FIG. 1U is a diagram of binding moiety containing A1, A2, A3, and A4 atoms.
Figure 1V:
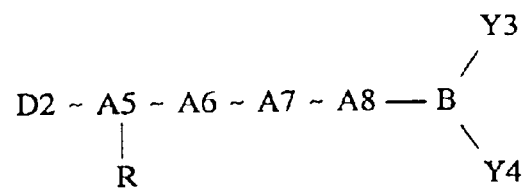

FIG. 1U is a diagram of binding moiety containing A1, A2, A3, and A4 atoms and FIG. 1V is a diagram of binding moiety containing A5, A6, A7, and A8 atoms. Thus, both sides of the chemical structure as shown in FIGS. 1A and 1B are binding moieties.

2. Heterobivalent Compounds: General Structure

Figure 2A:
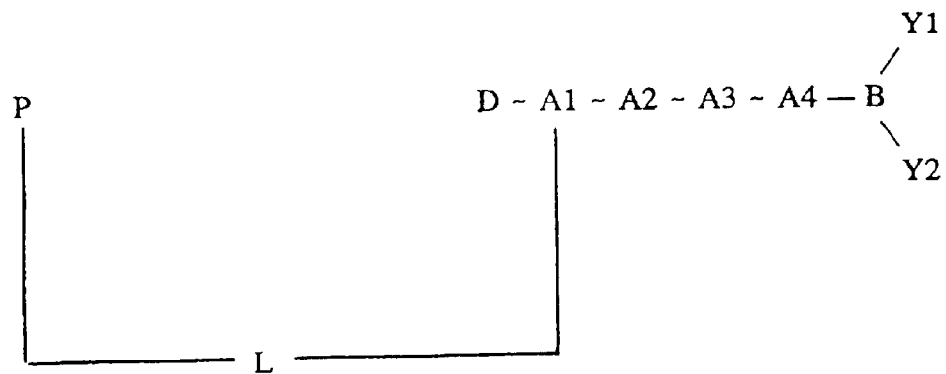
FIGS. 2A–2C are diagrams showing the general formula of several preferred heterobivalent compounds.
Figure 2B:
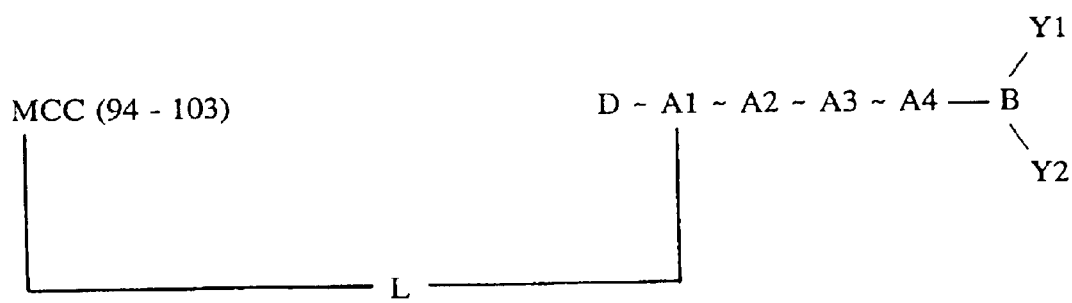
Figure 2C:
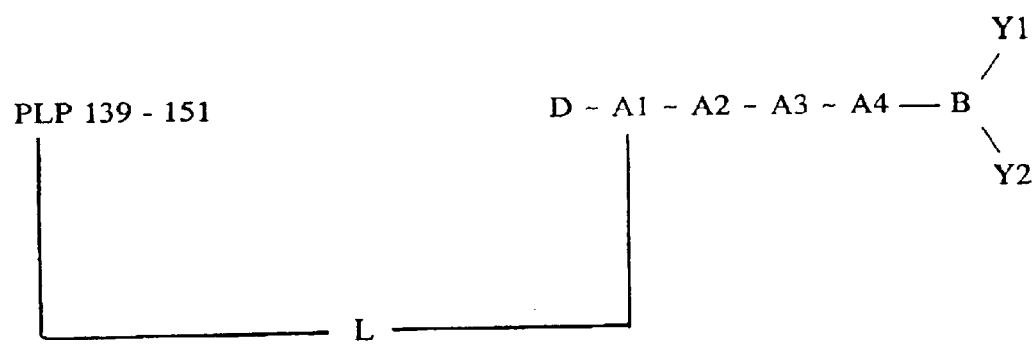

The heterobivalent compounds and agents taught herein may begin with the following general diagram as shown in FIG. 2A, the general formula for a heterobivalent compound. FIGS. 2A–2C are diagrams showing the general formula of several preferred heterobivalent compounds: FIG. 2A is a diagram of a general heterobivalent template; FIG. 2B is a diagram of a heterobivalent example coupling a binding moiety to an MCC peptide (94–103) using a compatible linker, e.g., an AAAAAA (SEQ ID NO.1), linker group where A is L-alanine or D-alanine; and FIG. 2C is a diagram of a heterobivalent example coupling a binding moiety to a PLP peptide (139–151) using a compatible linker, e.g., an AAAAAA (SEQ ID NO.1), linker group where A is L-alanine or D-alanine.

For this invention, peptide, polypeptide, or fragment thereof, are used interchangeably and is defined to include a chain of amino acids ranging from about 3 to 25 residues in length. Optimal size is in the order of about 10–18 amino acid residues in length.

Known antigenic peptides for any of the following autoimmune diseases, infectious diseases or allergic diseases listed below (without limitation) could be coupled to a bivalent template (see FIG. 2A), e.g., Xaa-boroPro, to form a heterobivalent compound (heterodimeric) molecule that could be used in this invention to treat that specific autoimmune disease. Thus, once coupled or linked to the bivalent or multivalent template (see FIG. 2A), these peptides form different heterobivalent compounds which can alter biological activity (increased or reduced) as a result of bivalent interaction inducing the association of two receptors.

AUTOIMMUNE DISEASES AND KNOWN ANTIGENIC PEPTIDES

| AUTOIMMUNE DISEASE | AUTOANTIGEN | REFERENCE |
|---|---|---|
| Addison's disease | adrenal specific antigen with a molecular weight of 18–24 kDa | Freeman, et al., Clinical & Experimental Immunology, 88(2):275–279 (May 1992) |
| hemolytic anemia | internal membrane protein and the integral red blood cell protein Band-3 | Perry, et al., European Journal of Immunology, 26(1):136–141 (January 1996) |
| antiphospholipid syndrome | epitopes on the fifth domain of beta 2-glycoprotein I | Wang, et al., Journal of Immunology, 155(3):1629–1636 (Aug. 1, 1995) |
| rheumatoid arthritis | deglycosylated aggrecan peptide spanning the chondroitin sulphate domain | Goodstone, et al., Annals of the Rheumatic Diseases, 55(1):40–46 (January 1996) |
| herpetiformis dermatitis | strong association with specific human histocompatibility leukocyte antigens DR3, Dqw2, and DPw1 | Hall, et al., Seminars in Dermatology, 10(3):240–245 (September 1991) |
| diabetes mellitus, insulin dependent | "The mapping of most of the genetic risk (or disease resistance) to specific alleles in the major histocompatibility locus (MHC class II) has direct functional implications for our understanding of autoimmunity in diabetes and directly implies that presentation of a likely narrow set of peptides is critical to the development of autoimmunity." | Karges, et al., Molecular Aspects of Medicine, 16(2):79–213 (1995) |
| allergic encephalomyelitis (major animal model for human multiple sclerosis) | proteolipid protein residues 139–151 | Kuchroo, et al., Journal of Immunology, 148(12):3776–3782 (Jun. 15, 1992) |
| glomerulonephritis, IgA | antibodies directed against endothelial cells | Wang, et al., Nephrology, Dialysis, Transplantation, 7(8):805–810 (1992) |
| glomerulonephritis, membranous | "Towards defining antigens in human membranous nephropathy" | Brenchley, et al., Nephrology, Dialysis, Transplantation, 7 Suppl. 1:21–24 (1992) |
| Goodpasture's syndrome | alpha 3 chain of type IV collagen | Kalluri, et al., Journal of the American Society of Nephrology, 6(4):1178–1185 (October 1995) |
| Grave's disease | thyroid stimulating hormone receptor | Mullins, et al., Journal of Clinical Investigation, 96(1):30–37 (July 1996) |
| Lambert-Eaton myasthenic syndrome | N- and L-type calcium channels | el Far, et al., Journal of Neurochemistry, 64(4):1696–1702 (April 1995) |
| lupus erythematosus, systematic | small nuclear ribonucleoprotein C, residues 117–126 | James, et al. Clinical & Experimental Rheumatology, 13(3):299–305 (May–June 1995) |
| multiple sclerosis | the small heat-shock protein alpha B-crystallin | van Noort, et al., Nature, 375(6534):798–801 (June 29, 1995) |
| myasthenia gravis | muscle nicotinic acetylcholine receptor | Protti, et al., Immunology Today, 14(7):363–368 (July 1993) |
| neuritis, experimental allergic | the homophilic cell adhesion molecule p0 glycoprotein, residues 56–71 and 180–199 | Linington, et al., European Journal of Immunology, 22(7):1813–1817 (July 1992) |
| sympathetic ophthalmia | autoantigen unknown but immunosuppressive therapy effective | Chan, et al., Archives of Ophthalmology, 113(5):597–600 (May 1995) |

-continued

AUTOIMMUNE DISEASES AND KNOWN ANTIGENIC PEPTIDES

| AUTOIMMUNE DISEASE | AUTOANTIGEN | REFERENCE |
|---|---|---|
| pemphigoid, bullos | an epidermal hemidesmosomal glycoprotein named BP180 (human) and mBP180 (mouse). In the mBP180 ectodomain, an antigenic site comprised of 9–12 residues designated mBP1 is recognized by pathogenic sera. | Liu, et al., Journal of Immunology, 155(11):5449–5454 (December 1995) |
| pemphigus | desmoglein 3 (DG) residues 190–204 | Wucherpfennig, et al., Proceedings of the National Academy of Sciences of the United States of America, 92(25):11935–11939 (December 1995) |
| polyendocrino-pathies, autoimmune | steroidogenic enzymes P450scc, P450c17, and P450c21 | Uibo, et al., Journal of Autoimmunity, 7(3):399–411 (June 1994) |
| purpura, thrombocytopenic, idiopathic | platelet surface glycoproteins Ib, IIb, IIIa with molecular weights 160, 135 88 kDa respectively. | Kokawa, et al., European Journal of Haematology, 50(2):74–80 (1993) |
| Reiter's disease | platelet unknown but antibiotic treatment is effective | Huges, et al., Seminars in Arthritis & Rheumatism, 24(3):190–210 (December 1994). |
| stiff-man syndrome | linear NH2-terminal epitope of glutamic acid decarboxylase 65 | Daw, et al., Journal of Immunology, 156(2):818–825 (Jan. 15, 1996) |
| thyroiditis, autoimmune | thyroid peroxidase | Chazenbalk, et al., Journal of Clinical Investigation, 92(1):62–74 (July 1993) |

INFECTIOUS DISEASES AND KNOWN ANTIGENIC PEPTIDES

| INFECTIOUS DISEASE | ANTIGENIC PEPTIDE (S) | REFERENCE |
|---|---|---|
| HIV-1 and HTLV-1 | Synthetic Peptide Immunogene | Hart, et al., Pharmaceutical Biotechnology, 6:821–845 (1995) |
| Malaria | SPF(66)n | Lopez, et al., Vaccine, 12(7):585–591 (1994) |
| Schistosomisis | Triose-Phosphate Isomerase | Reynolds, et al., Journal of Immunology, 152(1):193–200 (Jan. 1, 1994) |
| HIV-1 | Chemically Defined Synthetic Vaccine | Nardelli, et al., Journal of Immunology, 148(3):914–920 (Feb. 1, 1992) |
| Toxoplasmosis | Toxoplasmaa Gondii P30 Antigen | Darcy, et al., Journal of Immunology, 149(11):3636–3641 (Dec. 1, 1992) |
| Malaria | Epitopes of Cs and RESA Proteins | Ritu, et al., Vaccine, 10(11):761–765 (1992) |

ALLERGIC DISEASES AND KNOWN ANTIGENS

| ALLERGIC DISEASE | ANTIGEN(S) | REFERENCE |
|---|---|---|
| Cedar Allergy | (Cry j 1) - derived peptide | Ikagawa, et al., Journal of Allergy & Clinical Immunology, 97(1 Pt 1):53–64 (January 1996) |
| Penicillin Allergy | beta-lactam ring | Brander, et al., Journal of Immunology, 155(5):2670–2678 (Sep. 1, 1995) |
| House Dust Mite Allergy | Der p 2 allergen | O'Brien, et al., Immunology, 86(2):176–182 (October 1995) |
| Ragweed Allergy | Amb a 5 and Amb t 5 allergens | Greenstein, et al., Journal of Immunology, 155(10):5064–5073 (Nov. 15, 1995) |
| Soybean Allergy | Alpha-subunit of beta-conglycinin | Ogawa, et al., Bioscience, Biotechnology & Biochemistry, 59(5):831–833 (May 1995) |
| Bee Venom Allergy | Phospholipase A2 | Dudler, et al., European Journal of Immunology, 25(2):538–542 (February 1995) |
| Rye Grass Allergy | T cell epitores of the major fraction | Bungy, et al., European Journal of Immunology, 24(9):2096–2103 (September 1994) |
| Egg Allergy | Epitope of Ovalbumin | Shimojo, et al., International Archives of Allergy & Immunology, 105(2):155–161 (October 1994) |
| Dermatophagoides Pteronyssinus Allergy | Peptides of Der p 11 | Okana, et al., Allergy, 49(6):436–441 (July 1994) |

Listed below are examples of different known peptides with known specificity and high affinity for different T cell surface receptors. These peptides can be coupled to Xaa-boroPro or to FIG. 2A to form different heterobivalent compounds exhibiting altered biological activity (increased or reduced) as a result of the specific binding to the specific receptor.

HETEROBIVALENT PEPTIDES

| PEPTIDE | SPECIFIC FOR |
|---|---|
| Myelin Proteolipid Protein (PLP 139–151) | TCR*/CD3 |
| Moth Cytochrome C Peptide (MCC) | CD3 |
| Colony Stimulating Factor Peptide | TCR/CD3 |
| Stem Cell Factor Peptide | TCR/CD3 |
| HIV-1 GP 120 Peptide | CD4 |
| HIV-1 GP 120 | CD4 |
| P2 Peptide of Tetanus Toxoid | TCR/CD3 |
| Multiple Sclerosis Peptide | CD4 |
| Peptide Analog of Myelin Basic Protein | TCR |
| Myelin Proteolipid Protein | TCR |
| HIV-1 gp120 | TCR |
| Tetanus Toxoid | TCR |
| Stem Cell Factor (SCF) | SCF Receptor |
| Cytochrome c | TCR |
| Tetradecapeptide Epitope of Myelin Basic Protein | TCR |
| Colony-Stimulating Factor (CSF) | CSF-Receptor |

TCR: T cell Surface Receptor

3. Synthesis of H-boroPro and Xaa/Lys-boroPro

Homobivalent, homomultivalent, and heterobivalent compounds can begin with the synthesis of U-boroPro and Lys-boroPro as taught herein. Use of H-boroPro and Lys-boroPro are for example purposes only, and is not intended to limit the scope of this invention.

Standard peptide coupling chemistry methods and procedures used in this invention are taught in the following books, and incorporated herein by reference: P. D. Bailey, *An Introduction to Peptide Chemistry*, Ed.: John Wiley & Sons, 1990; Miklos Bodansky, *Peptide Chemistry, A Practical Textbook*, Ed.: Springer-Verlag, 1988; Miklos Bodansky, *Principles of Peptide Synthesis*, "Reactivity and Structure Concepts in organic Chemistry.," Volume 16, Ed.: Springer-Verlag, 1984; and Miklos Bodansky, *Principles of Peptide Synthesis*, "Reactivity and Structure Concepts in Organic Chemistry," Volume 21, Ed.: Springer-Verlag, 1984;

For this invention, Xaa/Lys-boroPro is an example of an molecule that can be used to form a binding moiety of a bivalent, homobivalent, homomultivalent, or heterobivalent compound as taught herein.

H-boroPro was prepared by the synthetic route previously developed and described (G. R. Flentke, E. Munoz, B. T. Huber, A. G. Plaut, C. A. Kettner, and W. W. Bachovchin. "Inhibition of dipeptidyl aminopeptidase IV (DP-IV) by Xaa-boroPro dipeptides and use of these inhibitors to examine the role of DP-IV in T-cell function," *Proc. of the Natl. Acad. of Sci. of the U.S. A.* 88, 1556–1559 (1991); also described in U.S. Pat. No. 5,462,928).

Alternatively, H-boroPro may be produced by a new procedure (Kelly, T. A., Fuchs, V. U., Perry, C. W., and Snow, R. J. "The efficient synthesis and simple resolution of a proline boronate ester suitable for enzyme inhibition studies," *Tetrahedron* 49, 1009–1016 (1993)). Both of these synthetic routes yield racemic H-boroPro pinanediol.

Stereochemically pure L,L and L,D diastereomers of Z-Lys-boroPro were prepared by first resolving racemic H-boroPro through crystallization with optically active blocking protecting groups ((1S,2S,3R,5S)-+-pinanediol isomer) followed by coupling the isotopically pure L-boroPro and D-boroPro to the stereochemically pure L isomer of lysine (See U.S. Pat. No. 5,462,928). Alternatively, the L,L and L,D diastereomers of Lys-boroPro were prepared in high optical purity by coupling racemic H-boroPro by L-Lys and separating the resulting diastereomeric Z-Lys-boroPro-diester into its component L,D and L,L diastereomers using reverse phase HPLC as previously described for diastereomeric Pro-boroPro (W. G. Gutheil and W. W. Bachovchin, "Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition," *Biochemistry* 32, 8723–8731 (1993)). Thus, there are several routes through which to obtain any of the four possible stereoisomers of Lys-boroPro. However, only the DP IV inhibitory L,L isomer and the DP IV non inhibitory L,D isomer were normally prepared for use as a control in the immunological experiments. All derivatives prepared herein use (or will use) optically pure diastereomers and therefore (or will) contain only either the L,L or the L,D isomer of Lys-boroPro.

Once prepared, these Xaa-boroPro compounds will be coupled to other Xaa-boroPro compounds, e.g., itself, to form a homobivalent (homodimeric) or multivalent compound or coupled to a peptide thereby forming a heterobivalent (heterodimeric) compound.

EXAMPLE 2

Synthesis of Homobivalent Compounds Designed to Induce Association Between T Cell CD26 Receptors Homobivalent, low molecular weight compounds capable of inducing an association between two CD26 receptors are taught in this Example. Homobivalent synthetic crosslinking compounds will have the properties normally associated with an antibody, i.e., high affinity, and specificity for CD26, and an ability to induce crosslinking. Thus, any experiment with an anti-CD26 monoclonal antibody will be possible with one or more of the homobivalent compounds, e.g., immunoprecipitations.

The synthetic ligands, however, will have some properties that make them complimentary to anti-CD26 mAbs. These include: (i) their binding epitope is the DP IV active site; (ii) they exhibit cross-species specificity; and (iii) they offer flexibility in adjusting the spacing between the binding sites and in the construction of chimeric or heterobidentate structure.

I. Synthesis of Homobivalent Xaa-boroPro Derivatives

Figure 3:
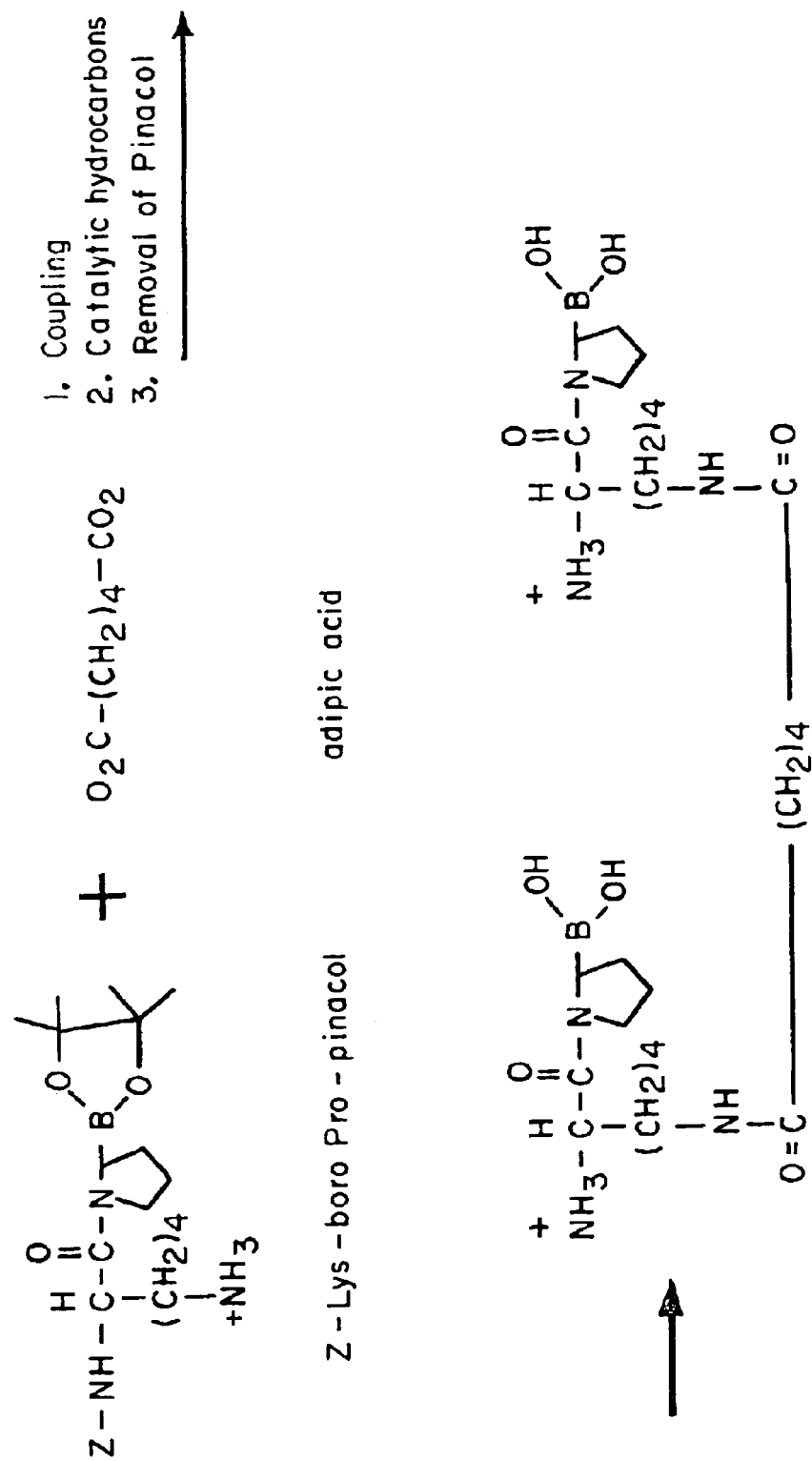
FIG. 3 is a diagram showing the synthesis of adipoyl (Lys-boroPro)$_2$, a homobivalent derivative of Lys-boroPro.

To produce molecules which induce the association between one cell surface CD26 with another cell surface CD26 and also retain DP IV inhibitory activity, a series of different homobivalent derivatives of Lys-boroPro will be linked via its ε-amino groups by a linker-spacer molecule containing two carboxylic acid groups, e.g., a six carbon linker spacer or linker group, using conventional peptide coupling methods (see FIG. 3). FIG. 3 is a diagram showing the synthesis of adipoyl (Lys-boroPro)$_2$, a homobivalent derivative of Lys-boroPro. This linkage method included coupling benzyloxycarbonyl-lysine-boroPro-diester (Z-lys-boroPro-diester) to a linker molecule, e.g., adipic acid or hexanedioic acid (HOOC(CH$_2$)$_4$COOH). The diester protecting group on the boronyl moiety can either be pinacol or pinanediol.

The general structure for this homobivalent (homodimeric) compound as shown in FIG. 1B:

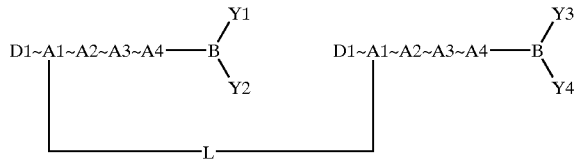

wherein D1, is independently selected from the group consisting of NH and NH$_2$, wherein N represents any isotope of nitrogen, wherein H represents any isotope of hydrogen; "~", independently, is selected from the group consisting of a single bond and a double bond; B represents, independently, any isotope of boron; A1 is, independently, selected from a group consisting of a C, a CX moiety and an N, wherein C represents any isotope of carbon, wherein X represents any atom capable of forming a single bond with C; each A2, A3, and A4 are, independently, selected from a group consisting of a CX moiety, a CXZ moiety, a CZ moiety, an NX moiety, and an O, wherein X and Z, are, independently, selected from the group consisting of any atom capable of forming a single bond and any atom capable of forming a double bond with C or N and wherein O represents any isotope of oxygen; wherein each Y1, Y2, Y3, and Y4 are, independently, selected from the group consisting of a hydroxyl moiety and any reactive moiety that converts to a hydroxyl moiety under physiologic conditions; and L represents a linker molecule (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous.

The structure as shown above need not be identical, in that it can have the general structure as shown in FIG. 1A:

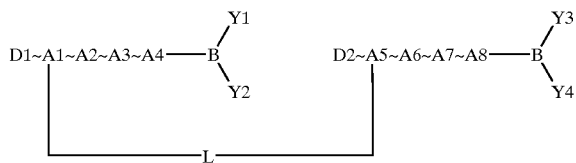

wherein D1 and D2, independently, are selected from the group consisting of NH and NH$_2$, wherein N represents any isotope of nitrogen, wherein H represents any isotope of hydrogen; "~", independently, is selected from the group consisting of a single bond and a double bond; B represents, independently, any isotope of boron; A1 and A5 are, independently, selected from a group consisting of a C, a CX moiety and an N, wherein C represents any isotope of carbon, wherein X represents any atom capable of forming a single bond with C; each A2, A3, A4, A6, A7, and A8 are, independently, selected from a group consisting of a CX moiety, a CXZ moiety, a CZ moiety, an NX moiety, and an O, wherein X and Z, are, independently, selected from the group consisting of any atom capable of forming a single bond and any atom capable of forming a double bond with C or N and wherein O represents any isotope of oxygen; wherein each Y1, Y2, Y3, and Y4 are, independently, selected from the group consisting of a hydroxyl moiety and any reactive moiety that converts to a hydroxyl moiety under physiologic conditions; and L represents a linker molecule (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous.

The coupling reaction can be achieved by any of several standard peptide coupling methodologies. For example, the Lys-boroPro homobivalent (homodimeric) derivative was prepared by reacting protected Lys-boroPro in anhydrous THF with the acid chloride form of adipic acid, i.e., adipoyl chloride, which is commercially available (Aldrich Co.). Following coupling, the N terminal Z protecting group was removed by catalytic hydrogenation. Deprotection of the boronyl group was achieved by transesterification with phenyl boronic acid and extracted using a two phase, low pH water solution/organic solvent.

II. Determination of Optimal Chemical Spacer Linkers

To determine the optimal spacer linker segment or linker molecule for inducing the association of one cell surface CD26 with another cell surface CD26 receptor, a series of bivalent, dimeric Lys-boroPro derivatives with varying length spacer segments will be prepared (See discussion below on linker molecules). A wide assortment of dicarboxylic spacer linker molecules are commercially available. This includes linker molecules which have various internal heteroatoms and other functional groups, in addition to the terminal carboxylic groups, e.g., ethylene glycobissuccinate ("EGS", shown in FIG. 13).

For example, using EGS in place of adipic acid provides a bivalent compound with a spacer of about twice the length of the adipoyl moiety. Also, the internal heteroatoms confer improved water solubility over a straight chain hydrocarbon of similar length.

Figure 13:
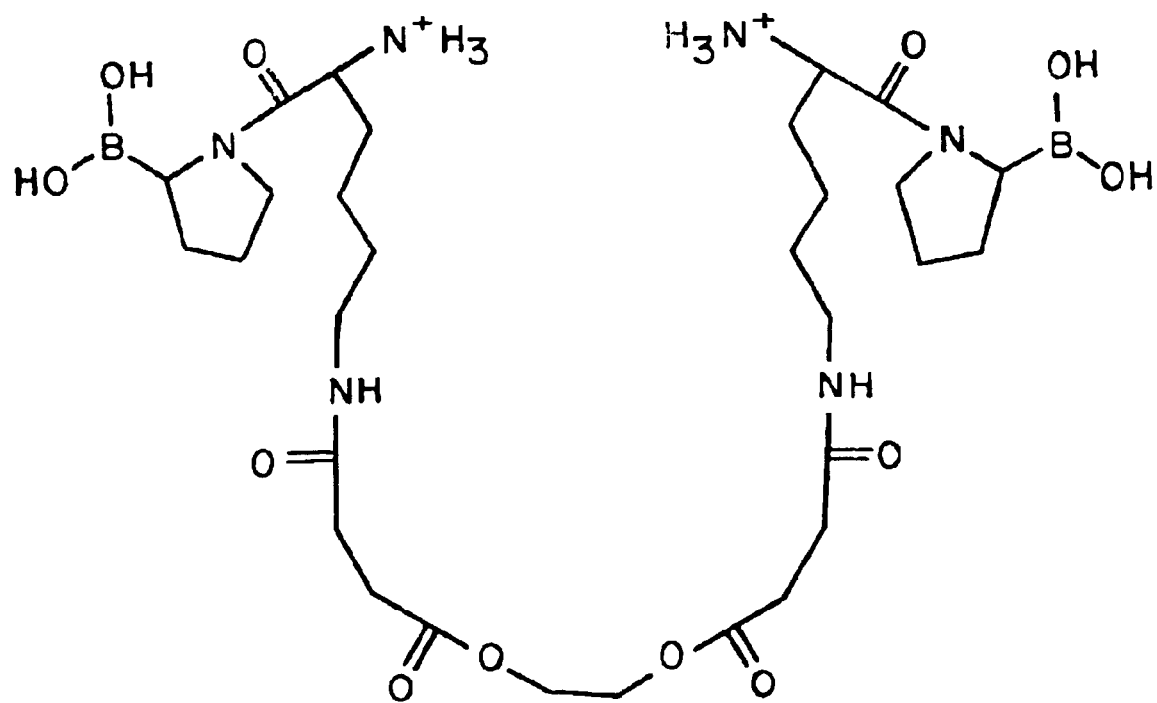
FIG. 13 is the structure of EGS, the spacer-linker molecule used in the homodimer (KbP)$_2$-EGS used in the experiments of FIG. 12.

FIG. 13 gives the structure of EGS, which was used as the linker molecule joining two KbP monomers, to form (KbP)$_2$ EGS. The synthesis of this homodimer was carried out in a manner analogous to that described herein for KbP$_2$ adipate, using appropriate modifications. EGS is commercially available from a variety of chemical supply companies.

Figure 5:
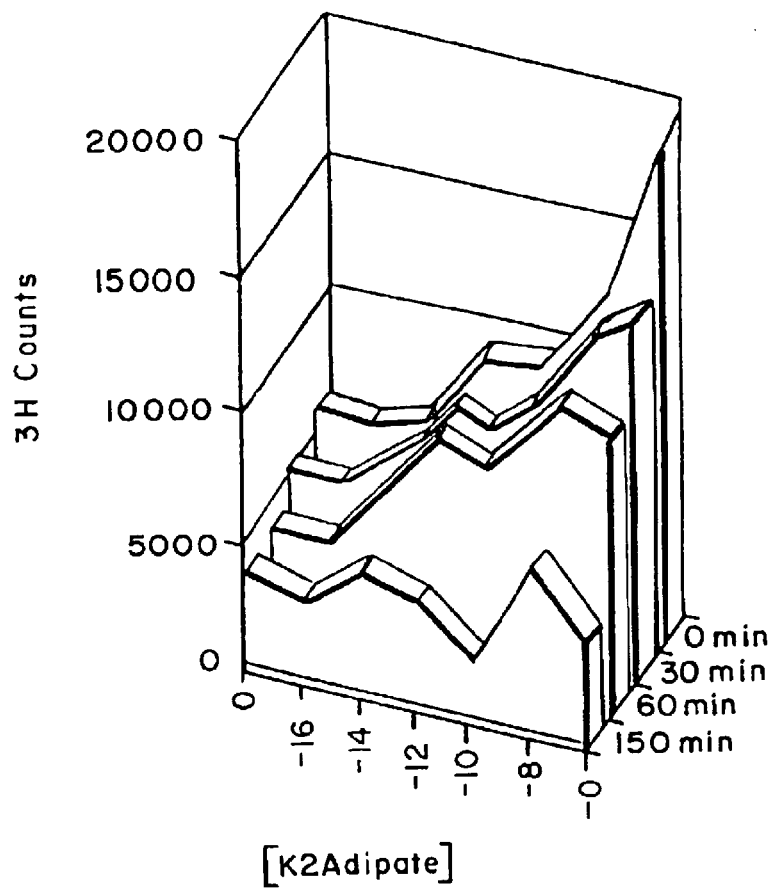
FIG. 5 is a graph showing a dose response curve observed with higher concentrations of KbP$_2$-Adipate on anti-CD3 mAb stimulation of H9 cells. Drug concentration is read as lox M.
Figure 12:
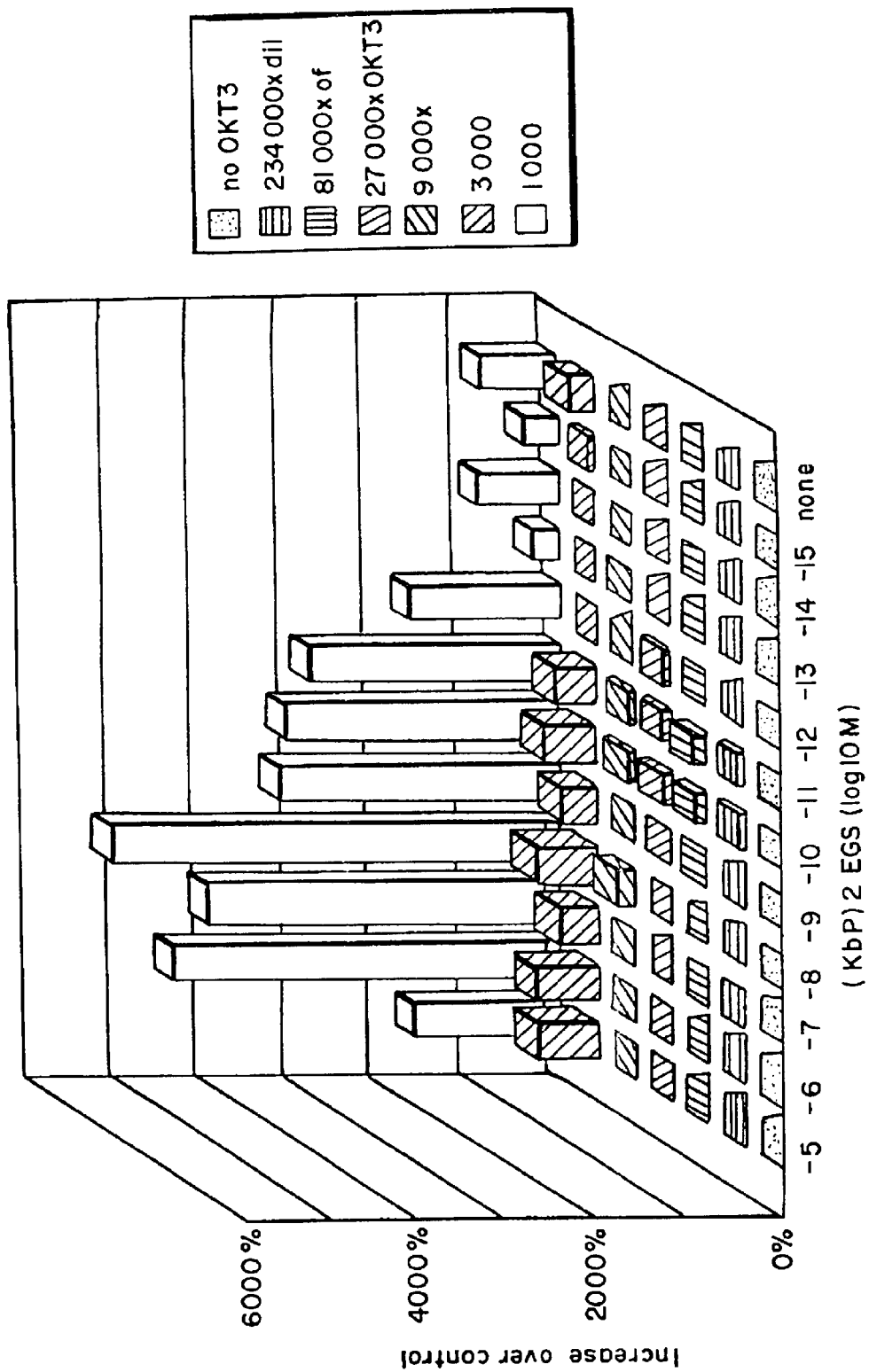
FIG. 12 is a graph illustrating the effect of (KbP)$_2$-EGS at varying concentrations on IL-2 production by H9 cells.

Both (KbP)$_2$ adipate and (KbP)$_2$ EGS were used in experiments with the T cell line H9 to determine their effects on activation (as measured by Il-2 production) and/or proliferation. Some of these experiments employ the homodimeric molecules as co-stimulatory factors with other, known T cell stimulatory factors such as the monoclonal antibody OKT3. The results of these experiments are shown in FIGS. 5 and 12.

III. Experimental Methods

To determine the effect KbP$_2$-Adipate had on anti-CD3 mAb stimulation of H9 cells, e.g., stimulation of suppressing IL-2 production, the following protocol was used.

In quadruplicate wells, H9 cells were preincubated with KbP$_2$-Adipate for 0, 30, 60, or 150 min. After the preincubation, the cells were seeded into a 96 well flatbottom plate pre-coated with anti-CD3 monoclonal antibody OKT3 at 1,000, 5,000, 10,000, 20,000, 50,000, or 100,000 times dilution of stock. After 24 hr, the cells were lysed by freezing at 4° C. IL-2 concentration in the H9 cells lysates was bioassayed using the IL-2 dependent cell line HT2, Watson, J. D. "Continuous proliferation of murine antigen specific helper T lymphocytes in culture," 1979, *Journal of Experimental Medicine*, 150:1510. HT2 proliferation was measured by counting 3H-thymidine incorporation.

Similar experiments were carried out with (KbP)$_2$-EGS and the co-stimulatory antibody OKT3; the results of these experiments are shown in FIG. 12.

IV. Results

1. Low Concentrations of KbP$_2$-Adipate Inhibits IL-2 Production

Figure 4:
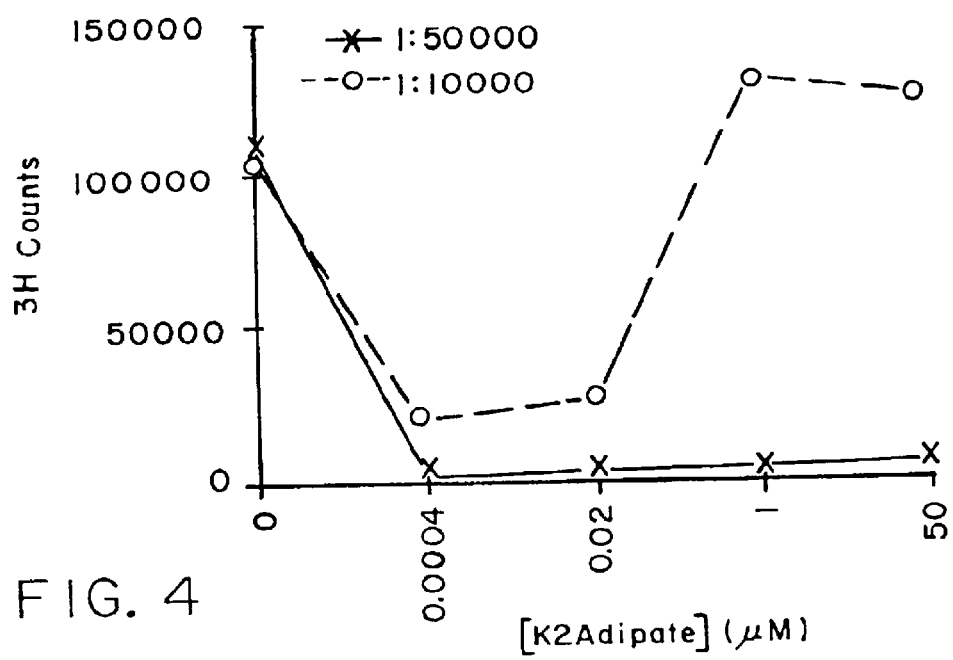
FIG. 4 is a graph showing a dose response curve observed with lower concentrations of KbP$_2$-Adipate on anti-CD3 mAb stimulation of H9 cells.

FIG. 4 is a graph showing a dose response curve observed with lower concentrations of KbP$_2$-Adipate on anti-CD3 mAb stimulation of H9 cells. The results show that KbP$_2$-Adipate is a potent immunosuppressant suppressing IL-2 production by 98% at $4.0 \times 10^{-10}$ M.

This dose response curve revealed important differences between bivalent, homodimeric KbP$_2$-Adipate effects on anti-CD3 mediated stimulation and those of previously reported monomeric Xaa-boroPro inhibitors. The first difference is that KbP$_2$-Adipate appears to be a far more potent immunosuppressant, suppressing IL-2 production by 98% at $4.0 \times 10^{-10}$ M. In contrast, Xaa-boroPro monomeric inhibitors exhibit measurable inhibition only at concentrations of $10^{-5}$ to $10^{-6}$ M, and moreover, the inhibition usually does not exceed 50%.

The increased potency of the bivalent, dimeric agent cannot be explained simply by a higher binding affinity for CD26 because the monomers, with picomolar dissociation constants, actually have the greater affinity for CD26.

The second difference is that this dose response curve is the reverse of that exhibited by the monomeric inhibitors and indeed of that normally expected for any agent with biological activity. FIG. 4 shows that inhibition by KbP$_2$-Adipate actually decreases with increasing KbP$_2$-Adipate concentrations. The monomeric inhibitors, in contrast, exhibit a normal dose response curve, with inhibition increasing as concentration of monomeric inhibitor increases; further in contrast to the dimers of the invention, the monomers have comparatively little effect on IL-2 production by H9 cells.

Finally, FIG. 4 suggests that high concentrations of KbP$_2$-Adipate does not inhibit IL-2 production but actually may stimulate it (See FIG. 5 below). The reversed dose response and the suggestion of stimulation at high concentrations suggest two competing biological effects at work: inhibition at low concentrations and stimulation at higher concentrations.

Possible explanations for the observed inhibitory activity shown in FIG. 3 were eliminated with proper negative controls. KbP$_2$-Adipate caused neither apoptotic nor non-apoptotic death since treatment did not affect cell viability assessed by hemocytometry counts using trypan blue and flow cytometry. Drug carryover from H9 lysates to HT2 readout cells did not explain the effect, since 50 mM KbP$_2$-Adipate did not increase or decrease HT2 responsiveness to IL-2. Finally, the fact that high concentrations of KbP$_2$-Adipate did not inhibit IL-2 production argues strongly that KbP$_2$-Adipate cannot be toxic to the cells (See below).

2. High Concentrations of KbP$_1$-Adipate Stimulates IL-2 Production

FIG. 5 is a graph showing a dose response curve observed with higher concentrations of KbP$_2$-Adipate on anti-CD3 mAb stimulation of H9 cells. Drug concentration is read as $10^x$ M. The same methods as taught above were employed.

These data demonstrate that KbP$_2$-Adipate has co-stimulatory activity, augmenting IL-2 production up to 4-fold. FIG. 5 also shows that this activity is dependent on both the concentration of KbP$_2$-Adipate and on the preincubation time. The stimulatory effect (i) is dose dependent, (ii) begins in the 1 pM range, and (iii) saturates in the 10 mM range. This effect is diminished by increasing preincubation times on a time frame consistent with internalization of CD26 receptor.

The fact that KbP$_2$-Adipate both inhibits and co-stimulates IL-2 production was surprising and puzzling. To further understand this, the experiments shown in FIGS. 4 and 5 were each repeated many times and essentially the same results were obtained each time.

Figure 6:
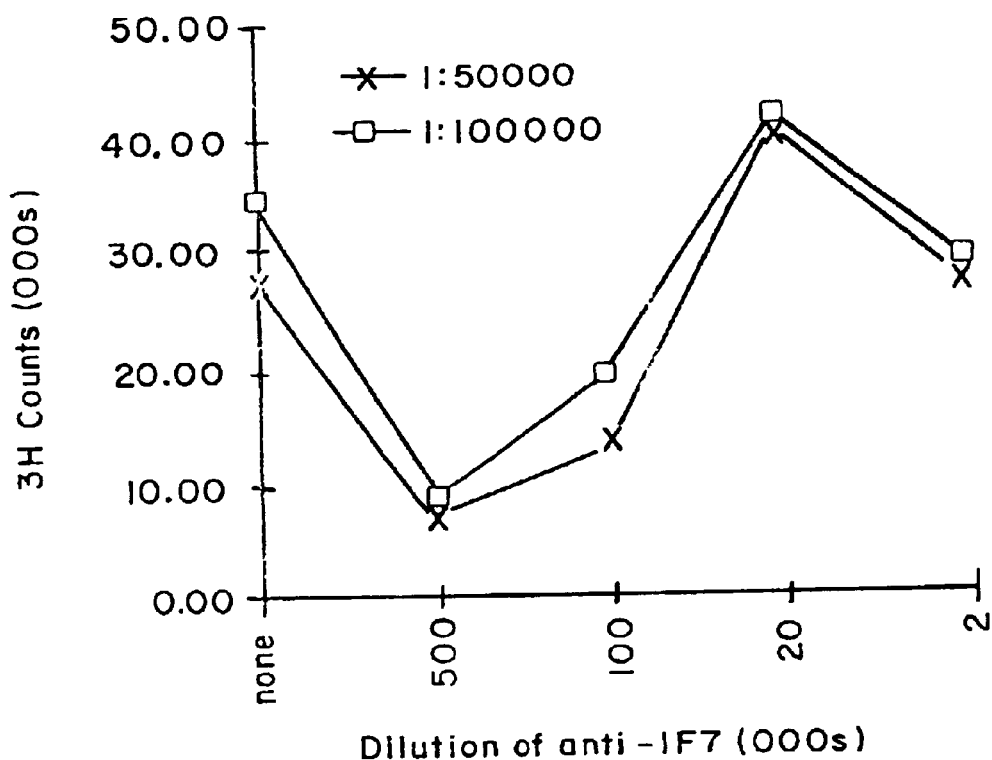
FIG. 6 is a graph showing a dose response curve for anti-1F7.

Furthermore, similar experiments were performed with the cross-linking anti-CD26 mAb anti-1F7, previously reported to co-stimulate CD4+CD26+ T cells REF. FIG. 6 is a graph showing a dose response curve for anti-1F7. The data showed that the cross-linking anti-CD26 mAb anti-1F7 can, in a manner similar to KbP$_2$-Adipate, both inhibit or co-stimulate, i.e. inhibition at low doses, co-stimulation at higher doses. Compare the dose response curve for anti-1F7 shown in FIG. 6 with that of KbP$_2$-Adipate (dashed line in FIG. 4.

Some shifting of the dose/response profiles for both KbP$_2$-Adipate and 1F-7, e.g., FIG. 4 for KbP$_2$-Adipate and FIG. 6 for 1F-7, was observed from one experiment to the next. This shifting might be due to variable levels of CD26 expression on the surface of T-cells from one preparation of cells to the next.

The fact that the bivalent, homodimeric molecule, KbP$_2$-Adipate, was a potent inhibitor at lower concentrations (FIG. 4), e.g., $10^{-10}$ M, yet a potent stimulator at higher concentrations, e.g., $10^{-6}$ M (FIG. 5), suggests that intermolecular reactions may be the cause of these opposite results.

Figure 7:
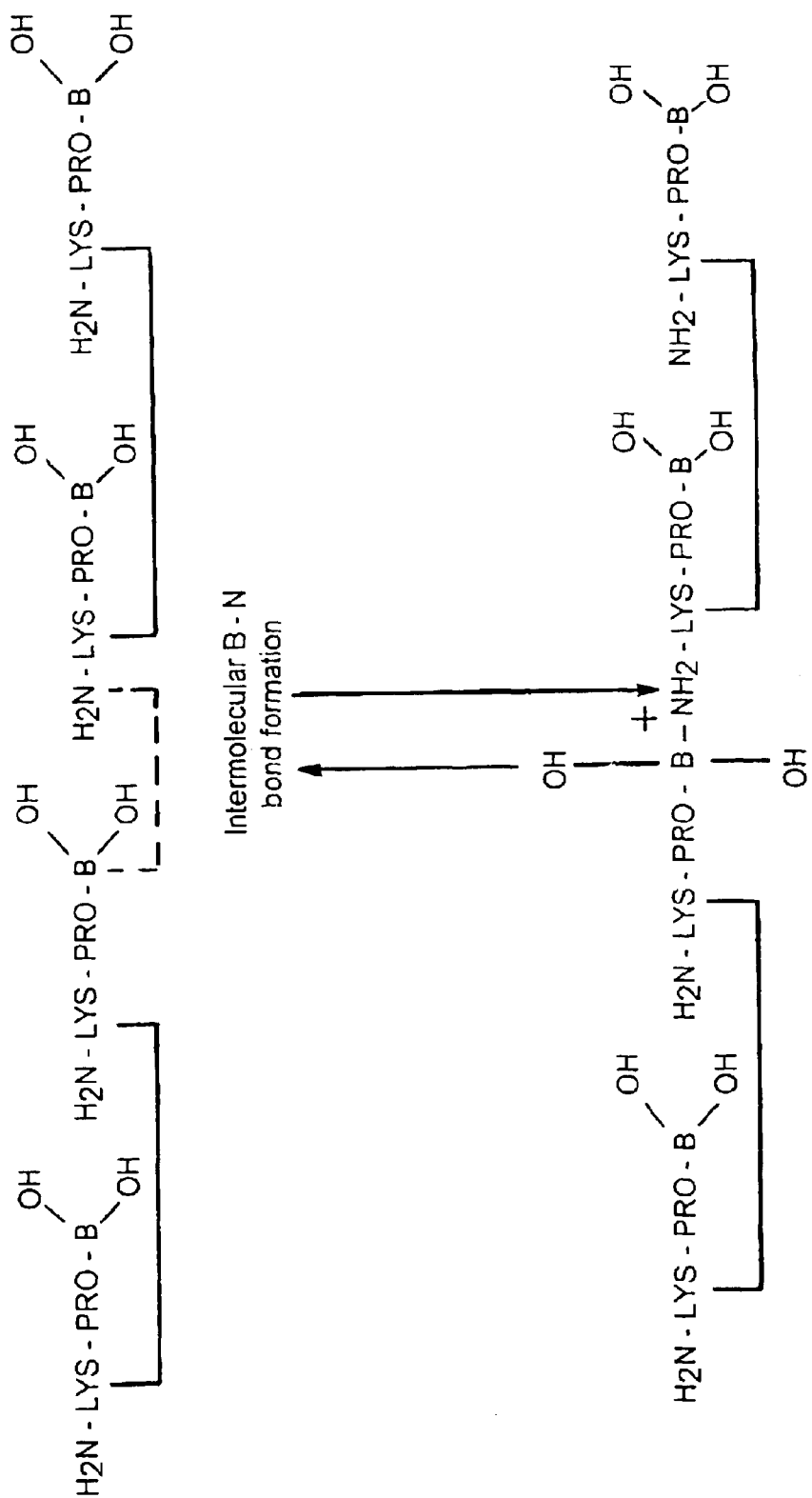
FIG. 7 is a diagram showing intermolecular reactions that may occur at higher concentrations of KbP$_2$-Adipate.

It was not surprising that low concentrations of KbP$_2$-Adipate would inhibit IL-2 production. The inventors predict that, at low KbP$_2$-Adipate concentrations, the reaction solution is mostly comprised of separate, non-interactive bivalent, dimeric molecules because the bivalent dimer is too small to induce intermolecular reactions between 2 or more bivalent, dimer molecules. However, the inventors predict that the observed stimulatory effect with higher KbP$_2$-Adipate concentrations was due to intermolecular reactions between two different bivalent, dimeric molecules. It is suggested that at higher concentrations of KbP$_2$-Adipate, intermolecular reactions between two different bivalent, dimeric molecules could form via a B—N bond. The amino group of one divalent molecule binds to a boron atom of a second divalent molecule. Further, the process can continue so that polymers of various lengths are formed. At equilibrium after polymerization, new bivalent compounds with linker spans greater than two times the size of the linker span of one dimeric compound may be formed. For example, the resultant new bivalent compound, as diagramed in FIG. 7, has lost a binding moiety from each dimer but now has a linker span of greater than twice the original linker span size. FIG. 7 is a diagram showing intermolecular reactions that may occur at higher concentrations of KbP$_2$-Adipate.

FIG. 12 shows the results of the experiments carried out with KbP$_2$-EGS, in which the two KbP monomers are linked by the EGS spacer, which is on the order of twice the length of the adipate spacer used to make KbP$_2$-Adipate homodimer. The results of the experiments with KbP$_2$-EGS exhibited a pattern analogous to the KbP$_2$-Adipate results, as FIG. 12 illustrates. For example, there is a co-stimulatory effect with the T cell activating antibody OKT3. Further, the greatest stimulatory effect was observed at low concentrations (i.e., high dilutions) of KbP$_2$-EGS, and after the peak stimulatory effect (alone or with OKT3), increasing concentrations decreased the activating effect observed.

3. Conclusions

The data showed that a low molecular weight synthetic crosslinker of the memory T-cell surface marker CD26, KbP$_2$-Adipate, had a higher affinity than antibodies and depending on specific conditions, either stimulated or inhibited T cell function. Key factors governing whether KbP$_2$-Adipate suppresses or co-stimulates are (1) preincubation time, (2) the concentration of KbP$_2$-Adipate, and (3) the dilution of the anti-CD3 MaB OKT3 used to stimulate the T cells.

EXAMPLE 3

Homomultivalent Polymeric Compounds Designed to Induce Association Between T Cell Surface Receptors A variety of different examples of homomultivalent compounds are taught in this example. The standard peptide synthesis methods described above can be used to prepare these compounds.

The general multivalent template has the following structure:

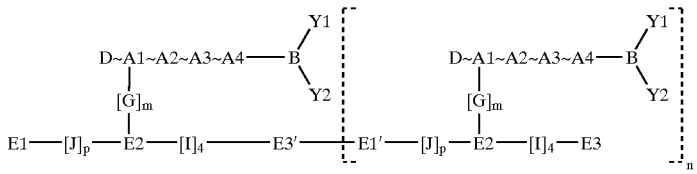

wherein D is, independently, selected from the group consisting of NH and NH$_2$, wherein N represents any isotope of nitrogen, wherein H represents any isotope of hydrogen; "~" is, independently, selected from the group consisting of a single bond and a double bond; B represents, independently, any isotope of boron; A1 is, independently, selected from the group consisting of a C, a CX moiety and an N, wherein c represents any isotope of carbon, wherein X represents any atom capable of forming a single bond with C; each A2, A3, and A4 are, independently, selected from the group consisting of a CX moiety, a CXZ moiety, a CZ moiety, an NX moiety, and an O, wherein X and Z, independently, are selected from the group consisting of any atom capable of forming a single bond and any atom capable of forming a double bond with C or N and wherein C represents any isotope of oxygen; wherein each Y1 and Y2 are, independently, selected from the group consisting of a hydroxyl moiety and any reactive moiety that converts to a hydroxyl moiety under physiologic conditions; n represents an integer between 1 and 200, inclusive;

wherein E1 and E3 are distinct reactive species in which:
(a) R and R' are the remainder of the molecules not relevant to this reaction;
(b) E1 is attached to R' by a covalent bond which are together designated as E1-R' or R'-E1;
(c) E3 is attached to R by a covalent bond which are together designated as E3-R or R-E3;
(d) R' represents the part of E1-R' not undergoing a chemical reaction;
(e) R represents the part of R-E3 not undergoing a chemical reaction;
(f) E1 undergoes a chemical reaction with E3 to form the product E1'-E3' and a byproduct F, wherein F is selected from the group consisting of 2H$^+$ and 2e$^-$, H$_2$O, and any other byproduct;
(g) where H$^+$ is the cation of any isotope of hydrogen and e$^-$ is an electron;
(h) where H represents any isotope of hydrogen and O represents any isotope of oxygen;
(i) where E1' and E3' are covalently bonded;
(j) E1 does not undergo a chemical reaction with another E1;
(k) E3 does not undergo a chemical reaction with another E3; and
(l) E1 and E3 are selected from the group consisting of a carboxylate, amino, imidazole, sulfhydryl, aldehyde, ester, and any other reactive species;

wherein [J]p, E2, [I]q and [G]m together are a linker moiety, and wherein [G]m, [J]p, and [I]q represent, independently, linker molecules (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous; and wherein m, p, and q represent, independently, an integer from 1 to 50, inclusive.

and wherein E2 is selected from the group consisting of CX, CH, N, PhYZ, PhU, and any other moiety capable of forming covalent bonds with [J]$_p$, [G]$_m$, and [I]$_q$ and wherein:
(a) C is any isotope of carbon;
(b) X is any isotope of any atom capable of forming a single bond with carbon;

(c) H is any isotope of hydrogen;
(d) N is any isotope of nitrogen;
(e) Ph is any isotope of phosphorous;
(f) Y is any isotope of any atom capable of forming a single bond with phosphorous;
(g) Z is any isotope of any atom capable of forming a single bond with phosphorous; and
(h) U is any isotope of any atom capable of forming a double bond with phosphorous.

Also, the figures shown below represent the binding moiety and R represents the remainder of the molecule in this polymeric compound:

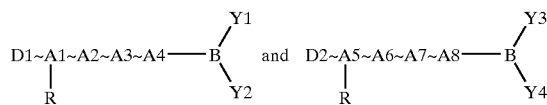

The multivalent compound of this invention can range from a dimer, e.g., n is equal to one (1) or up to about 50-mer, e.g., n is equal to forty-nine (49). When the binding moiety is repeated more than 2 times (a dimer) then the compound would necessarily be a "polymeric" compound with a finite number of repeating binding moieties.

EXAMPLE 4

Synthesis of Heterobivalent Compounds Designed to Induce Association Between CD26 Receptor and the T Cell Surface Receptor (TCR/CD3)

Constructing heterobivalent (also referred to as heterobidentate or heterodimeric), compounds or agents yields a class of agents capable of inducing an association between CD26 and distinct cell surface receptors. Such heterobifunctional molecules have interesting biological activities and may be useful as drugs.

The general structure for a heterobivalent compound of this invention as shown in FIG. 2A:

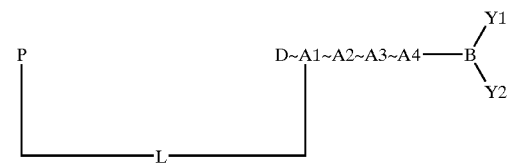

wherein D is independently selected from the group consisting of NE and NH$_2$, wherein N represents any isotope of nitrogen, wherein E represents any isotope of hydrogen; "~", independently, is selected from the group consisting of a single bond and a double bond; B represents, independently, any isotope of boron; A1 is, independently, selected from the group consisting of a C, a CX moiety and an N, wherein C represents any isotope of carbon, wherein X represents any atom capable of forming a single bond with C; each A2, A3, and A4 are, independently, selected from the group consisting of a CX moiety, a CXZ moiety, a CZ moiety, an NX moiety, and an O, wherein X and Z, independently, are selected from the group consisting of any atom capable of forming a single bond and any atom capable of forming a double bond with C or N and wherein O represents any isotope of oxygen; wherein each Y1 and Y2 are, independently, selected from the group consisting of a hydroxyl moiety and any reactive moiety that converts to a hydroxyl moiety under physiologic conditions; L represents a linker molecule (i) having a molecular weight ranging between about 100 daltons and about 2000 daltons, (ii) having a span ranging from about 20 Å to about 300 Å, and (iii) containing a chain of atoms selected from the group consisting of a combination of C, O, N, S, and Ph atoms, connected by single bonds or by double bonds in a manner that does not violate the laws of chemistry and wherein S represents any isotope of sulfur and Ph represents any isotope of phosphorous; and P represents a peptide ranging from 3 to 30 amino acids having sufficient sequence homology to bind to a naturally occurring receptor.

Two different heterobivalent compounds (heterodimers) of Lys-boroPro have been constructed and tested. These two compounds are presented as examples only and are not intended to limit the invention. In one heterobivalent compound, Lys-boroPro is linked, coupled, or tethered to the C terminal carboxylate of encephalitogenic myelin proteolipid protein (PLP 139–151; FIG. 2C; see below for discussion). In the second hetero-compound, compound, Lys-boroPro is linked, coupled, or tethered to an antigenic moth cytochrome C peptide (MCC; FIG. 2B; see below for discussion). Both compounds were designed such that association between CD26 and another T cell receptor (TCR/CD3) would be induced. The data presented below demonstrate that both heterobidentate molecules were much more stimulatory than using the peptides alone.

1. Synthesis of Lys-boroPro Linked to Myelin Proteolipid Protein (PLP) Peptide 139–151 To Induce Association Between CD26 Receptor and the T Cell Surface Receptor (TCR/CD3)

Proteolipid protein (PLP) is the major protein of central nervous system myelin. Kruchroo and co-workers have shown that mice immunized with a peptide corresponding to residues 139–151 of PLP, HSLGKWLGHPDKF, (SEQ. ID NO.2) (PLP 139–151) develop acute experimental autoimmune encephalomyelitis (Kuchroo, V. K., Sobel, R. A., Yamamura, T., Greenfield, E., Dorf, M. E., and Lees, M. B., Induction of experimental allergic encephalomyelitis by myelin proteolipid-protein-specific T cell clones and synthetic peptides, *Pathobiology* 59, 305–312 (1991); Kuchroo, V. K., Byrne, M. C., Atsumi, Y., Greenfield, E., Connolly, J. B., Whitters, M. J., O'Hara, R. J., Collins, M., and Dorf, M. E., T-cell receptor alpha chain plays a critical role in antigen-specific suppressor cell function, *Proceedings of the National Academy of Sciences of the United States of America* 88, 8700–8704 (1991); Kuchroo, V. K., Sobel, R. A., Laning, J. C., Martin, C. A., Greenfield, E., Dorf, M. E., and Lees, M. B., Experimental allergic encephalomyelitis mediated by cloned T cells specific for a synthetic peptide of myelin proteolipid protein. Fine specificity and T cell receptor V beta usage, *Journal of Immunology* 148, 3776–3782 (1992); Kuchroo, V. K., Martin, C. A., Greer, J. M., Ju, S. T., Sobel, R. A., and Dorf, M. E., Cytokines and adhesion molecules contribute to the ability of myelin proteolipid protein-specific T cell clones to mediate experimental allergic encephalomyelitis, Journal of Immunology 151, 4371–4382 (1993); Kuchroo, V. K., et al., T cell receptor (TCR) usage determines disease susceptibility in experimental autoimmune encephalomyelitis: studies with TCR V beta 8.2 transgenic mice, *Journal of Experimental Medicine* 179, 1659–1664 (1994); and Kuchroo, V. K., Greer, J. M., Kaul, D., Ishioka, G., Franco A., Sette, A., Sobel, R. A., and Lees, M. B., A single TCR antagonist peptide inhibits experimental allergic encephalomyelitis mediated by a diverse T cell repertoire, *Journal of Immunology* 153, 3326–3336 (1994)). PLP 139–151 also induces the proliferation of T cells in culture. The mechanism involves the T cell receptor (TCR) recognition and binding of this peptide within the context of the major histocompatibility complex (MHC) class II. The MHC is a cluster of genes on human chromosome 6 or mouse chromosome 17 that encodes the MHC molecules. The MHC class I molecules or proteins are the present peptides generated in the cytosol to CD8 T cells. The MHC class II molecules or proteins are the present peptides degraded in cellular vesicles to CD4 T cells. The MHC is the most polymorphic gene cluster known to date in the human genome, having large numbers of alleles at several different loci. Because this polymorphism is usually detected using antibodies or specific T cells, the MHC proteins are often called "major histocompatibility antigens." This allows easy manipulation of the antigenic peptide to convert it from an agonist to an antagonist (Jorgensen, J. L., Reay, P. A., Ehrich, E. W., and Davis, M. M., Molecular components of T-cell recognition, *Annu. Rev. Immunol.* 10, 835–873 (1992)).

Systematic amino acid replacement studies have demonstrated that Trp 144 and His 147, shown in bold in the sequence, are necessary for TCR binding while Leu 145 and Pro 148, shown underlined in the sequence above, are necessary for MHC binding.

Figure 8:
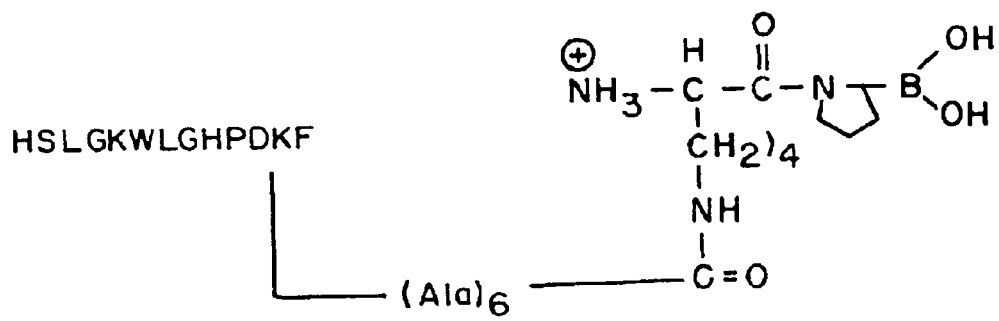
FIG. 8 is a diagram showing Lys-boroPro linked to Myelin Proteolipid Protein (PLP) Peptide 139–151.

Crystal structure data on the MHC class II receptor shows that the cleft on top of the molecule which binds the antigenic peptide is open on both sides, which allows longer peptides to be presented by simply permitting them to extent away form the MHC receptor. In contrast, MHC class I receptors only accommodate short peptides from 9 to 12 amino acids and the antigenic peptide ends are not free. The above facts therefore suggest that a bivalent, heterodimer of Lys-boroPro linked to PLP 139–151 could be constructed that would simultaneously bind to the T cell surface receptor (TCR) and CD26 (see FIG. 8) and the MHC II on the antigen presenting cell. FIG. 8 is a diagram showing Lys-boroPro linked to Myelin Proteolipid Protein (PLP) Peptide 139–151.

In the case of PLP, the heteordimer was constructed as HSLGKWLGHPDKFAAAAAA-εKbP (SEQ ID NO.3), where HSLGKWLGHPDKF (SEQ ID NO.2), was PLP 139–151, AAAAAA (SEQ ID NO. 1), was a linker comprised of 6 alanines and εKbp was Lysine-boroProline in which the ε-amino of Lysine is covalently attached to the —COOH terminus of HSLGWLGHPDKFAAAAAA (SEQ ID NO.3). The first synthetic step was to order a custom peptide from a synthetic peptide lab. Using long established protocols, the peptide was built from the C-terminus staring with alanine which was immobilized on a resin. Sequentially AAAAAFKDPHGLWKGLSH (SEQ ID NO.4), were added using protected amino acids. The peptide was then removed from the resin to give a free —COOH terminus which could be reacted to form a peptide bond. The other residues HSLGKWLGHPDKFAAAAA (SEQ ID NO.5), were unreactive owing to protecting groups. Lysine-boroProline in which the α-$NH_2$ of Lysine was protected, the $B(OH)_2$ of boro Proline was protected with pinanediol, and the ε-$NH_2$ of Lysine was free was coupled to the peptide. The coupling was a peptide bond (—(C=O)—NH—) formed by standard peptide chemistry techniques. The result was then deprotected to yield the final product.

The spacer linker consisting of six consecutive Ala residues was chosen to provide a span sufficient to permit crosslinking (~30 Å).

The proliferative effect of PLP-S-KbP on several different T cell clones that recognize PLP 139–151 were tested. T cell clones that recognize an irrelevant epitope, were used as negating controls. The protocol used is described (Kuchroo, V. K., et al., B7-1 and B7-2 Costimulatory Molecules Activate Differentially the Th1/Th2 Developmental Pathways: Application to Autoimmune Disease Therapy, *Cell* 80, 707–718 (1995)) and is incorporated herein by reference. Proliferation was measured by thymidine uptake. Table 1 below compares the effect PLP-S-KbP, antigenic PLP 139–151 peptide and non-antigenic PLP 103–116 peptide has on proliferation in different five PLP 139–151 specific T cell clones.

The results show that heterodimeric PLP-S-KbP strongly enhances the proliferative response to PLP 139–151 of all five 139–151 specific clones (see Table 1 below). Enhancement ranges from 100 to over 1000-fold, with respect to the concentration needed to produce a given response. For example, against the first T cell clone listed, 5B8.G8.E6.H12, 0.1 µM of PLP-S-KbP induces almost double the response that a 100-fold higher concentration of PLP 139–151 itself induces, for an enhancement of almost 200-fold. Similarly, nearly a 2000-fold enhancement is induced in the 4E3.B11.D9.H10.H6 cells since 0.1 µM of PLP-S-KbP produces almost double the response a 1000-fold higher concentration of PLP 139–151 itself enduces.

These results indicate that a low molecular weight synthetic molecule designed to crosslink CD26 and the TCR, e.g., PLP-S-KbP, strongly enhanced the T cell response to the T cell receptor recognized antigen.

TABLE 1

PROLIFERATIVE EFFECT OF PLP-S-KBP ON SEVERAL
T CELL CLONES SPECIFIC FOR PLP 139-151

| Antigen | Dose (µM) | | | | Clone |
|---|---|---|---|---|---|
| | 100 | 10 | 1 | 0.1 | |
| PLP-S-KbP | 34,716* | 53,628 | 22,022 | 15,1715 | 5B8.G8.E6.H12 |
| PLP 139-151 | 41,073 | 9,176 | 349 | 106 | |
| PLP103-116 | 143 | 74 | 226 | 124 | |
| PLP-S-KbP | 31,635 | 17,516 | 2,527 | 681 | SPL.C1.H2.F2 |
| PLP 139-151 | 809 | 400 | 107 | 423 | |
| PLP103-116 | 150 | 479 | 123 | 238 | |
| PLP-S-KbP | 17,608 | 15,753 | 8,580 | 3,688 | (4E3.B11.-D9.H10.H6) |
| PLP 139-151 | 1,932 | 534 | 125 | 318 | |
| PLP103-116 | 274 | 224 | 559 | 178 | |
| PLP-S-KbP | 36,686 | 26,410 | 7,738 | 175 | 2E5.G10.G5.E5 |
| PLP 139-151 | 1,506 | 70 | 288 | 101 | |
| PLP103-116 | 107 | 60 | 434 | 307 | |
| PLP-S-KbP | 43,999 | 35,521 | 8,202 | 187 | 7A5.F10.G11 |
| PLP 139-151 | 2,324 | 406 | 222 | 117 | |
| PLP103-116 | 124 | 117 | 314 | 556 | |

*$^3$H counts

II. Synthesis of Lys-boroPro Linked to Moth Cytochrome C Peptide (MCC) 94–103 To Induce Association Between CD26 Receptor and the T Cell Surface Receptor (TCR/CD3)

The Moth Cytochrome C (MCC) 94–103 peptide is another antigenic peptide employed in this invention. MCC strongly induces IL-2 production and T cell proliferation when added to cultures of the murine 2B4 T cell hybridoma. The critical residues for binding to the TCR receptor and to the class II MHC are known (Jorgensen, J. L., Reay, P. A., Ehrich, E. W., and Davis, M. M. Molecular components of T-cell recognition, *Annu. Rev. Immunol.* 10, 835–873 (1992)). Because residues critical for MHC and TCR binding are located near the C terminus, Lys-boroPro was coupled to the N terminus of this peptide using a spacer linker of about the same length as used to link Lys-boroPro to the PLP peptide. Standard coupling methodologies were employed. This molecule was designated KbP-S-MCC to signify coupling to the N terminus.

Figure 9:
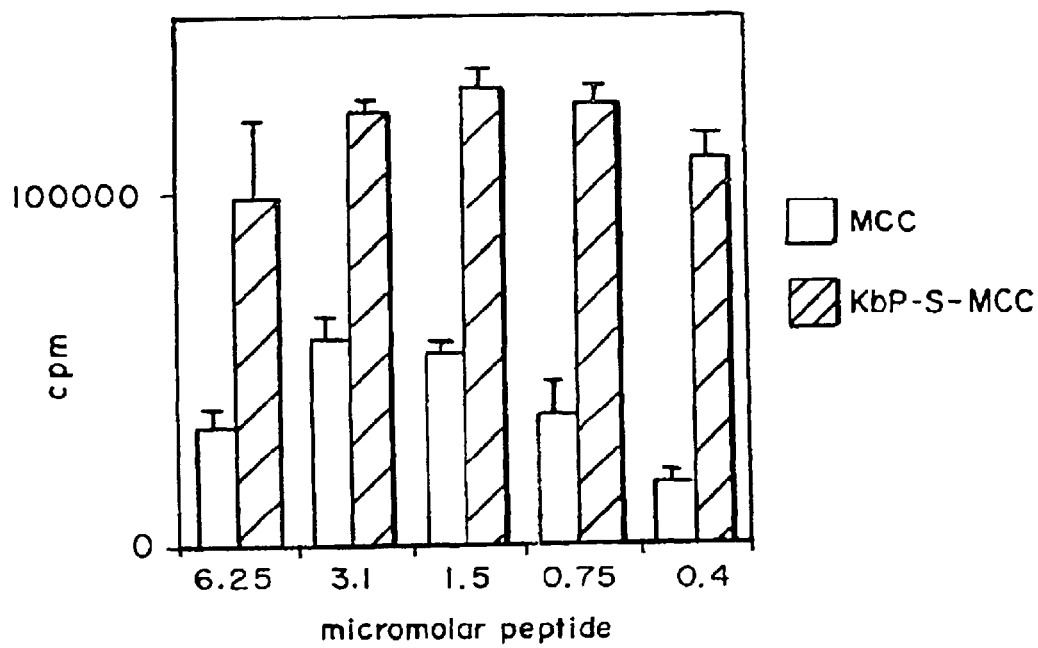
FIG. 9 is a graph comparing the effects heterobivalent coupled KbP-S-MCC and uncoupled MCC 94–103 have on IL-2 production in 2B4 cells.

FIG. 9 compares the effect of the bivalent, dimeric KbP-S-MCC molecule and MCC 94–103 itself on IL-2 production in 2B4 cells. The 2B4 T cell hybridoma proliferates in responses to moth cytochrome C peptide 94–103. The peptide 2B4 system is ideal for these studies, since the contest points between MCC 94–103 and the TCR have been determined (Jorgensen, J. L., Reay, P. A., Ehrich, E. W., and Davis, M. M. "Molecular components of T-cell recognition," *Annu. Rev. Immunol.* 10, 835–873 (1992)).

2B4 cells were cultured at $10^{+5}$/well with H-$2^k$ APC's and with varying concentrations of KbP-S-MCC and MCC itself. After 24 hrs the supernatant was harvested and the IL-2 content determined in a bioassay using HT-2 indicator cells in the same manner as previously described for the PLP peptide assays.

The results demonstrate that coupling Lys-boroPro to MCC strongly enhances the response to the antigenic MCC peptide. Even at the lowest concentration of KbP-S-MCC tested, e.g., 0.4 µM KbP-S-MCC, KbP-S-MCC induced a response at least double that of the maximum response obtained with the MCC peptide alone, which required ~10-fold higher concentration (See FIG. 9).

These results indicate that a low molecular weight synthetic molecule designed to crosslink CD26 and the TCR, e.g., KbP-S-MCC, strongly enhanced the T cell response to the T cell receptor recognized antigen.

III. Synthesis of Lys-boroPro Linked to Other Peptides To Induce Association Between CD26 Receptor and the T Cell Surface Receptor (TCR\CD3)

Other heterodimers comprising various derivatives of the PLP or the MCC peptide, which were previously shown to be antagonistic, will be prepared and studies will be performed to determine if linking these peptides to Lys-boroPro enhances their antagonistic activity or transforms them into an agonistic molecule.

Also, tetanus toxoid peptide P2 is of interest because it provides a test system involving human peripheral blood mononuclear cells (PBMC) (Wyse-Coray, T., Brander, C., Bettens, F., Mijic, D., Pickler, W. J., "Use of antibody/peptides constructs of direct antigenic peptides to T cells: evidence for T cell processing and presentation," *Cellular Immunology,* 139(1):268–73, (1992)). It has been shown that tetanus toxoid peptide P2 peptide induces a response in all HLA haplpotypes tested so far (Panina-Bordignon, P., Tan, A., Termijtelen, A., Demotz, S., Corradin, G., and Lanzavecchia, A. "Universally immunogenic T cell epitopes: Promiscuous binding to human MHC class II and promiscuous recognition by T cells," *Eur. J. Immunol.* 19, 2237–2242 (1989)). Thus, bivalent, heterodimers of Lys-boroPro coupled (linked) to the P2 peptide of tetanus toxoid will be prepared. Different spacer linkers of varying sizes will be tested to determine the optimal length to be used with this peptide. The coupling chemistry needed to produce the bivalent, heterodimer, Lys-boroPro linked to tetanus toxoid peptide P2 peptide, is the same as described above.

Additionally, other molecules capable of inducing the association between CD26 and the T cell surface receptor, e.g., TCR/CD3, will be prepared by coupling Lys-boroPro to the C terminal or N terminal functional group of different peptides known to bind to the T cell receptor in the context of class II MHC receptors. Similar protocols-as those used to prepare [PLP 139–151]-KbP and KbP-S-MCC, both of which are described above and which involve straightforward standard peptide coupling methodology, will be employed.

EXAMPLE 4

Heterobivalent Compounds Designed to Induce Association Between CD26 Receptor and the CD4 T Cell Surface Receptor Heterobivalent compounds containing Xaa-boroPro designed to induce association between the CD26 receptor and the CD4 receptor will be prepared. A molecule known to bind to CD4, e.g., peptides derived from the HIV-1 GP 120 protein, will be coupled to Xaa-boroPro (Ebenbichler, C., Westervelt, P., Carrillo, A., Henkel, T., Johnson, D., and Ratner, L., "Structure-function relationships of the HIV-1 envelope V3 loop tropism determinant: evidence for two distinct conformations," *Aids* 7, 639–46 (1993); Linsley, P. S., Ledbetter, J. A., Kinney, T. E., and Hu, S. L., "Effects of anti-gp120 monoclonal antibodies on CD4 receptor binding by the env protein of human immunodeficiency virus type 1," *Journal of Virology* 62, 3695–702 (1988)); Rini, J. M., Stanfield, R. L., Stura, E. A., Salinas, P. A., Profy, A. T., and Wilson, I. A., "Crystal structure of a human immunodeficiency virus type 1 neutralizing antibody, 50.1, in complex with its V3 loop peptide antigen," *Proceedings of the National Academy of Sciences of the United States of America* 90, 6325–9 (1993).

An Xaa-boroPro molecule, e.g., Lys-boroPro, will be coupled to one of the peptides from the HIV-1 GP 120 protein by using the coupling methodology as described above for coupling Lys-boroPro to the PLP peptide.

Different spacer linkers of varying sizes will be evaluated to determine the optimal length for inducing the association between CD26 and CD4.

EXAMPLE 5

Heterobivalent Compounds Designed to Induce Association Between CD26 and Other T Cell Surface Receptors Heterobivalent compounds containing Xaa-boroPro designed to induce association between the CD26 receptor and other T cell surface receptors, e.g., granulocyte colony stimulating factor, will be prepared.

For example, cytokine granulocyte colony stimulating factor (G-CSF or granulocyte macrophage colony stimulating factor, GM-CSF), is produced by T cells and macrophages and binds to its own receptor on the T cell surface (the granulocyte colony stimulating factor receptor). A bivalent, heterodimeric form of granulocyte colony stimulating factor could enhance the potency of granulocyte colony stimulating factor by stimulating of growth or differentiation or both in cells of myelomonocytic lineage. This compound can be prepared by using standard coupling methodology to couple granulocyte colony stimulating factor to Lys-boroPro. Also, different spacer linkers of varying sizes will be evaluated to determine the optimal length for inducing the association between CD26 receptor and the receptor for colony stimulating.

Stem cell factor (c-kit ligand) is essential in stem cell development and binds to the stem cell factor receptor on T cells. In B cell development, CD44 binding probably has no direct signaling function, but instead promotes the binding of a receptor known as c-kit. Lymphoid progenitor cells and early pro-B cells bind to hyaluronic acid on stromal cells via CD44, promoting the binding of their surface c-kit tyrosine kinase to stem cell factor (SCF) on the stromal cell surface, activating the kinase and inducing proliferation. A bivalent, heterodimeric form of stem cell factor, e.g., by coupling to Lys-boroPro, may enhance the potency of SCF.

Lys-boroPro-SCF, heterodimeric compound can be prepared by using methodologies similar to that described above. Different spacer linkers of varying sizes will be tested to determine the optimal length for inducing the association between CD26 receptor and the receptor for stem cell factor.

EXAMPLE 6

Synthesis of a Bivalent Compound Linked to an all D-amino Acid Peptide Synthesized in Reverse to Prevent Natural Proteolysis This example is designed to synthesize a bivalent compound linked to different peptides, whereby the peptides are resistant to natural proteolysis, e.g., Xaa-boroPro coupled to "protected" PLP. By "protected" is meant the peptide has been synthesized in the reverse and has a change in chirality.

Retro-Inverso Isomers

Evolution has ensured the almost exclusive occurrence of L-amino acids in naturally occurring proteins. Virtually all proteases therefore cleave peptide bonds between adjacent L-amino acids; thus, artificial proteins or peptides composed of D-amino acids are largely resistant to proteolytic breakdown. This resistance has been attractive to drug designers, but the exclusivity of biological systems for proteins made of L-amino acids means that such proteins cannot interact with the mirror image surfaces formed by enantiomeric proteins. Thus, an all D-amino acid protein usually has no biological effect or activity.

Linear modified retro-peptide structures have been studied for a long time (Goodman, M. et al., On the Concept of Linear Modified Retro-Peptide Structures, *Accounts of Chemical Research,* 12(1), 1–7 (January, 1979)) and the term "retro-isomer" was designated to include an isomer in which the direction of the sequence is reversed compared with the parent peptide. By "retro-inverso isomer" is meant an isomer of a linear peptide in which the direction of the sequence is reversed and the chirality of each amino acid residue is inverted; thus, there can be no end-group complementarity.

More recently, Jameson et al. engineered an analogue of the hairpin loop of the CD4 receptor by combining these two properties: reverse synthesis and a chance in chirality (Jameson et al., A rationally designed CD4 analogue inhibits experimental allergic encephalomyelitis, *Nature,* 368, 744-746 (1994) and Brady, L. et al, Reflections on a Peptide, *Nature,* 368, 692–693 (1994)). With the aim of overcoming proteolytic degradation and prolonging drug lifetime in vivo, Jameson et al modified all naturally occurring amino acids in the CD4 hairpin loop from L-enantiomers to D-enantiomers. The surface of this peptide was presumably a mirror image of the original peptide, however, and although resistant to degradation, it did not have the appropriate biological effect. But, when Jameson, et al synthesized this all D-amino acid peptide in reverse, with the carboxy terminus becomes the amino terminus (and vice versa), the resulting side-chain surface was an identical copy of its naturally occurring counterpart.

The net result of combining D-enantiomers and reverse synthesis is that the positions of carbonyl and amino groups in each amide bond are exchanged, while the position of the side-chain groups at each alpha carbon is preserved. Jameson et al demonstrated an increase in biological activity for their reverse D-peptide, which contrasts to the limited activity in vivo of its conventional all-L enantiomer (owing to its susceptibility to proteolysis).

Also, a partially modified retro-inverso pseudopeptide was used as a non-natural ligand for the human class I histocompatibility molecule, HLA-A2 (Guichard et al., Partially Modified Retro-Inverso Pseudopeptides as a Non-Natural Ligands for the Human Class I Histocompatibility Molecule HLA-A2, J. Med. Chem. 39, 2030–2039 (1996)). The data demonstrate that such non-natural ligands had increased stability and high MHC-binding capacity.

Preparation of Heterobivalent Compounds Containing Retro-Inverso Peptides

In this example, the Xaa-boroPro derivatives will be linked to different all D-amino acid peptides synthesized in reverse with a change in chirality to prevent natural proteolysis and yet are still engineered to induce association between a CD26 receptor and another CD26 receptor or with a different T cell surface receptor, e.g., TCR/CD3, CD4, CD8. In this example, the D form of the amino acid will first be prepared and these "all D-amino acids" will then be synthesized in reverse, designated "retro-inverso isomers or peptides," whereby the carboxy terminus becomes the amino terminus (and vice versa), and the resulting side-chain surface is therefore an identical to its naturally occurring counterpart.

Since an inherent problem with native peptides is degradation by natural proteases, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound.

The protocol given in Example 4, Section 1, for synthesizing PLP 139–151-KbP will be used, with some modifications as necessary, to synthesize the retro-inverso containing heterodivalent compounds described above. The primary modifications are (1) to synthesize the peptide in reverse and (2) to use D-amino acids for starting materials.

The biological activity of the retro-inverso heterodimer-Lys-boroPro linked to retro-inverso PLP 139–151 will be compared to the control heterodimer-Lys-boroPro linked to conventional PLP 139–151. Activation of T cells will be monitored as described previously in Example 4, Section 1.

A higher biological activity is predicted for the retro-inverso containing heterodimer when compared to the non-retro-inverso containing analog owing to protection from degradation by native proteinases.

EXAMPLE 7

Optimal Linker Molecule Determination

To determine the optimal linker molecule segment capable of inducing the association of one cell surface CD26 receptor with another cell surface CD26 receptor, a series of bivalent, dimeric compounds, with varying length spacer segments (linker molecules), will be prepared. A wide assortment of dicarboxylic spacer linker molecules are commercially available (see below for discussion). This includes linker molecules which have various internal heteroatoms and other functional groups, in addition to the terminal carboxylic groups, e.g., ethylene glycobissuccinate.

The corresponding span of the binding sites for monoclonal antibodies varies owing to individual flexibility but is typically about 30 Å to about 100 Å. Thus, most linker molecules designed for constructing the homobivalent and heterobivalent compounds of this invention will fall within the general range of about 20 Å to about 300 Å; and more specifically, from about 30 Å to about 100 Å. For example, the spacer linker consisting of six consecutive Ala residues (as used above) was chosen because it was the smallest length spacer believed to be sufficient to crosslink (~30 Å)

Using the linker ethylene glycobissuccinate (instead of adipic acid) provides a bivalent compound with a spacer of about twice the length of the adipoyl moiety. Also, the internal heteroatoms may confer improved water solubility over a straight chain hydrocarbon of similar length.

A. Background on Applicable Linker Molecules

Chemical cross-linkers are valuable tools for scientists and are discussed in numerous books and catalogues, e.g., Pierce Catalog and Handbook, Rockford, Ill. These reagents are used to assist in the determination of near-neighbor relationships in proteins, three-dimensional structures of proteins, enzyme-substrate orientation, solid-phase immobilization, hapten-carrier protein conjugation and molecular associations in cell membranes. They are also useful for preparing antibody-enzyme conjugates, immunotoxins and other labeled protein reagents.

Conjugates consisting of more than two components are difficult to analyze and provide less information on spatial arrangements of protein subunits. The number of components should be kept low or to a minimum. Like many applications, it is necessary to maintain the native structure of the protein complex, so cross-linking agents often employ functional groups that couple to amino acid side chains of peptides. Bifunctional reagents are classified on the basis of the following:

1. Functional groups and chemical specificity
2. Length of cross-bridge
3. Whether the cross-linking groups are similar (homobifunctional) or different (heterobifunctional)
4. Whether the groups react chemically or photochemically
5. Whether the reagent is cleavable
6. Whether the reagent can be radio-labeled or tagged with another label.

Reactive groups that can be targeted using a cross-linker include primary amines, sulfhydryls, carbonyls, carbohydrates and carboxylic acids (to be discussed below). In addition, any reactive group can be coupled nonselectively using a cross-linker such photoreactive phenyl azides. When considering protein—protein interactions, it is difficult to predict the proximity between reactive groups.

Cross-linkers are available with varying lengths of spacer arms or bridges. These bridges connect the two reactive ends. The most apparent attribute of the bridge is its ability to deal with steric considerations of the moieties to be linked. Because steric effects dictate the distance between potential reaction sites for cross-linking, different lengths of bridges are required for the interaction. Normally, a cross-linker with a short spacer arm (4–8 Å) is used and the degree of cross-linking is determined. If this is unsuccessful, a cross-linker with a longer spacer arm is used. Shorter spacer arms are often used in intramolecular cross-linking studies. Intermolecular cross-linking is favored with a cross-linker containing a longer space arm.

Many factors must be considered to determine optimum cross-linker-to-protein molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Conjugation reagents contain at least two reactive groups. Homobifunctional cross-linkers can contain at least two identical reactive groups, and heterobifunctional reagents contain two or more different reactive groups. Homobifunctional cross-linkers that couple through amines, sulfhydryls or react non-specifically are available from many commercial sources.

B. Homobifunctional Cross-linkers

Homobifunctional cross-linkers have at least two identical reactive groups and more often used in a one-step reaction procedure in which the compounds to be coupled are mixed, and the cross-linker is added to the solution. This cross-linking method may result in self-conjugation, intramolecular cross-linking and/or polymerization.

1. Primary Amine-Reactive Group

There are two major types of homobifunctional amine-reactive cross-linkers—homobifunctional imidoesters and homobifunctional N-hydroxysuccinimidyl (NHS) esters. Commercially available homobifunctional imidoesters range in size from about 8 Å to about 11.9 Å. Commercially available homobifunctional N-hydroxysuccinimidyl esters range in size from about 6.2 Å to about 16.1 Å.

Because primary amines are commonly found in proteins, homobifunctional NHS ester cross-linkers are the most commonly used conjugation reagents. Both yield stable derivatives.

2. Sulfhydryl-Reactive Group Maleimides, alkyl and aryl halides, α-haloacyls and pyridyl disulfides are thiol reactive groups. These reagents react faster with sulfhydryls, making them thiol-selective. Maleimides, alkyl and aryl halides, and α-haloacyls react with sulfhydryls to from thiol ether bonds. Pyridyl disulfides react with sulfhydryls to produce mixed disulfides. The pyridyl disulfide product is cleavable.

3. Nonselective Group

A nonselective homobifunctional is useful for conjugating functional groups, such as hydroxyls for which specific cross-linkers are not available.

An example of a nonselective homobifunctional cross-linker is BASED (Product #21564 Pierce Co.). This cross-linker has a long spacer arm and 2 aromatic rings which makes it very hydrophilic with a limited solubility in aqueous systems. This cross-linker also has a large diffusion capacity and should permeate membranes before conjugation initiates.

C. Heterobifunctional Cross-Linkers

Heterobifunctional cross-linkers possess two or more different reactive groups that allow for sequential conjugations with specific groups of proteins, minimizing undesirable polymerization or self-conjugation. Homobifunctional reagents sometimes result in unacceptable levels of polymerization. Heterobifunctional reagents are used when modification of amines is problematic. Amines may sometimes be found at the active sites of macromolecules, and the modification of these may lead to the loss of activity. Other moieties such as sulfhydryls, carboxyls, phenols and carbohydrates may be more appropriate targets. A two-step strategy allows for the coupling of a protein that can tolerate the modification of its amines to a protein with other accessible groups.

A variety of heterobifunctional cross-linkers, each combining different attributes for successful conjugation are commercially available. The majority of commercially available heterobifunctional cross-linkers contain an amine-reactive functional group. Cross-linkers that are amine-reactive at one end and sulfhydryl-reactive at the other end are quite common. Commercially available heterofunctional cross-linkers range in size from about 0 Å (EDC, Pierce Co.) to about 15.6 Å.

If using heterofunctional reagents, the most labile group should be reacted first to ensure effective cross-linking and avoid unwanted polymerization. Most heterobifunctional cross-linkers are sulfhydryl-reactive NHS-esters. The sulfhydryl reactive groups are usually maleimides, pyridyl disulfides and α-haloacetyls. Carbodiimides are carboxyl and amine reactive.

Heterobifunctional reagents, in which the reactivity can be controlled and that contain one group that is spontaneously non-reactive, have distinct advantages. This allows for specific attachment of the labile group first; the second reaction can then be initiated when appropriate. A selection of heterobifunctional reagents that contain at least one photoaffinity group are commercially available. This selection includes iodinatable and cleavable reagents that react nonspecifically at the azido group and with amines, sulfhydryls, carbohydrates and carbonyls. Often a bifunctional photoactivatable cross-linker has a better chance of forming a covalent cross-link than a bifunctional chemically reactive cross-linker. The high reactivity of the photochemical reagent allows for formation of a conjugate that may not be possible with a group-specific reagent. However, the yield resulting from a photoreactive cross-linker is low, and yields of less than 10% should be considered acceptable.

D. Reactivities of Different Chemical Groups

1. Imidoester Cross-linkers

Imidoester homobifunctional cross-linkers were among the first used to immobilize proteins onto solid-phase supports. They were used extensively for the study of protein structure and molecular associations in membranes. Although these cross-linkers are still used in protein subunit studies and solid-phase immobilization, they have been steadily replaced by the more stable, more efficient homobifunctional NHS-ester cross-linkers. Homobifunctional imidoesters maintain the net electronic charge on protein after cross-linking. Spacer arm lengths range from about 8.6 Å to about 11.9 Å. Imidoester cross-linkers react rapidly with amines at alkaline pH, but they have short half lives.

Imidoesters are also very useful for protein—protein cross-links. These cross-linkers can penetrate cell membranes and cross-link proteins within the membrane to study membrane composition, structure and protein—protein and protein-lipid interactions. Imidoesters are also useful for oligomer formation. For example, cross-linking proteins to form oligomers may reveal if a bivalent, dimeric or trimeric form of the protein is responsible for activity.

2. N-Hydroxysuccinimide-Esters (NHS-esters)

NHS-esters yield stable products upon reaction with primary or secondary amines. Coupling is efficient at physiological pH, NHS-ester cross-linkers are also more stable in solution than their imidate counterparts. Homobifunctional NHS-ester conjugations are commonly used to cross-link amine-containing proteins in either one-step or two-step reactions.

Primary amines are the principle targets for NHS-esters. Accessible α-amine groups present on the N-termini of proteins react with NHS-esters and form amides. However, because α-amines on a protein are not always available, the reaction with side chains of amino acids become important. While five amino acids have nitrogen in their side chains, only the ε-amines react significantly with NHS-esters. A covalent amide bond is formed when the NHS-ester cross-linking agent reacts with primary amines, releasing N-hydroxysuccinimide.

3. Coupling through Sulfhydryl Groups

Coupling through sulfhydryl groups is advantageous because it can be site-directed, yield cleavable products and allow for sequential coupling. A protein in a complex mixture can be specifically labeled if it is the only one with a free sulfhydryl group on its surface.

a. Maleimides

The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not rect with tyrosines, histidines or methionines.

b. Haloacetyls

The most common used α-haloacetyl cross-linkers contain the iodoacetyl group. α-Haloacetyls react with sulfhydryl groups at physiological pH. The reaction of the iodoacetyl group with a sulfhydryl proceeds by nucleophilic substitution of iodine, with a thiol producing a stable thioether linkage. Selectivity for sulfhydryl groups is ensured by using only a slight excess of the iodoacetyl group over the number of sulfhydryl groups at pH 8.3. In the absence of free sulfhydryls, or if a gross excess of iodoacetyl group is used over the number of sulfhydryls, the iodoacetyl group can react with other amino acids.

C. Pyridyl Disulfides

Pyridyl disulfides react with sulfhydryls groups to form a disulfide bond. Pyridine-2-thione is released as a by-product of this reaction. These reagents can be used as cross-linkers and to introduce sulfhydryl groups into proteins.

4. Coupling Through Carboxyl Groups: Carbodiimides

Carbodiimides couple carboxyls to primary amines or hydrazides, resulting in formation of amide or hydrazone bonds. Carbodiimides are unlike other conjugation reactions in that no cross-bridge is formed between the molecules being coupled. Carboxy termini of proteins can be targeted, as well as glutamic and aspartic acid side chains. In the presence of excess cross-linker, polymerization is likely to occur because proteins contain carboxyls and amines. No cross-bridge is formed, and the amide bond is the same as a peptide bond, so reversal of the cross-linking is impossible without destruction of the protein. EDC (Pierce Co.) reacts with carbocyclic acid group and activates the carboxyl group, allowing it to be coupled to the amino group ($R_4NH_2$) in the reaction mixture.

5. Nonselective Labeling: Arylazides

A photoaffinity reagent is a compound that is chemically inert but becomes reactive when exposed to ultraviolet or visible light. Arylazides are photoaffinity reagent that are photolyzed at wavelengths between 250–460 nm, forming a reactive aryl nitrene. The aryl nitrene reacts nonselectively to form a covalent bond. Reducing agents must be used with caution because they can reduce the azido group.

6. Nonselective Labeling a. Arginine Specific Cross-linkers

Glyoxals are useful compounds for targeting the guanidinyl portion of arginine residues. Glyoxals will target arginines at mildly alkaline pH. The is some cross-reactivity (the greatest at higher pH) with lysines.

b. Carbonyl Specific Cross-Linkers

Carbonyls (aldehydes and ketones) react with amines and hydrazides at pH 5–7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

7. Applications for Use of Cross-linkers a. Cell Surface Cross-linking

To ensure cell-surface specific cross-linking for identification of surface receptors or their ligands, it is best to use membrane-impermeable cross-linkers. In the past, researchers used water-insoluble cross-linkers and carefully controlled the amount of cross-linker and the cross-linking duration. This prevented penetration of the membrane by the cross-linker and subsequent reaction with membrane proteins. Many references cite the use of membrane-permeable cross-linkers for cell surface cross-linking.

b. Subunit Cross-linking and Protein Structural Studies

Cross-linkers can be used to study the structure and composition of proteins in biological samples. Some proteins are difficult to study because they exist in different conformations under varying pH or salt conditions. One way to avoid conformational changes is to cross-link the subunits together. Amine-, carboxyl- or sulfhydryl-reactive reagents are employed for identification of particular amino acids or for the determination of the number, location and size of subunits in a protein. Short-to-medium spacer arm cross-linkers are selected when intramolecular cross-linking is performed. If the spacer arm is too long, intermolecular cross-linking can occur. Carbodiimides that result in no space arm, along with short length conjugating reagents.

c. Intermolecular Cross-Linking for the Study of Protein Interactions and Associations Cross-linkers are widely used for identification of near-neighbor protein relationships, ligand-receptor identification and interactions, and enzyme substrate orientations. The cross-linkers chosen for these applications are usually longer than those used for subunit cross-linking. Homobifunctional, amine-reactive NHS-esters or imidates and heterobifunctional, amine-reactive, photoactivatable phenyl azides are the most commonly-used cross-linkers for these procedures. Occasionally, a sulfhydryl- and amine-reactive cross-linker may be employed if one of the two proteins or molecules is know to contain sulfhydryls. Cleavable or noncleavable cross-linkers are typically used. Because the distances between two molecules are not always known, the optimum length of the spacer arm of the cross-linker may be determined by the use of a panel of similar cross-linkers with different lengths. NHS-ester, phenylazides are very useful for this type of cross-linking because they usually result in some successful, if not efficient, cross-linking.

Cross-linkers can be used to determine whether a particular protein is located on the surface or the integral part of the membrane. These studies are possible because water-soluble cross-linkers are membrane-impermeable, while water-insoluble cross-linkers are membrane permeable.

d. Cell Membrane Structural Studies

Cell membrane structural studies require reagents of varying hydrophobicity to determine the location and the environment within a cell's lipid bilayer. Fluorescent tags are used to locate proteins, lipids or other molecules inside and outside the membrane. Various cross-linkers with differing spacer arm lengths can be used to cross-link proteins to associated molecules within the membrane to determine the distance between molecules. Successful cross-linking with shorter cross-linkers is a strong indication that two molecules are interacting in some manner. Failure to obtain cross-linking with a panel of shorter cross-linkers, while obtaining conjugation with the use of longer reagents, generally indicates that the molecules are located in the same part of the membrane but are not interacting. Homobifunctional NHS-esters, imidates or heterobifunctional NHS-esters, photoactivatable, phenyl azides are commonly used for these procedures.

8. Immunotoxins

Specific antibodies can be covalently linked to toxic molecules and then used to target antigens on cells. Often these antibodies are specific for tumor associated antigens. Immunotoxins are brought into the cell by surface antigens and, once internalized, they proceed to kill the cell by ribosome inactivation or other means. The type of cross-linker used to make an immunotoxin can affect its ability to locate and kill the appropriate cells. For immunotoxins to be effective, the conjugate must be stable in vivo. In addition, once the immunotoxin reaches its target, it is important that the antibody be separable from the toxin to allow the toxin to kill the cell. Thiol-cleavable, disulfide-containing conjugates have been shown to be more cytotoxic to tumor cells than noncleavable conjugates of ricin A immunotoxins. Cells are able to break the disulfide bond in the cross-linker, allowing the release of the toxin within the targeted cell.

9. Carrier Protein-Hapten/Peptide/Polypeptide Conjugates for Use as Immunogens

Companies, e.g., Pierce Co., offer products in this area of immunological research. Easy-to-use kits are available for coupling ligands using several different chemistries. There are many cross-linkers used for the production of these conjugates, and the best choice is dependent on the reactive groups present on the hapten and the ability of the hapten-carrier conjugate to function successfully as an immunogen after its injection. Carbodiimides are good choices for producing peptide carrier conjugates because both proteins and peptides usually contain several carboxyls and primary amines.

Other heterobifunctional cross-linkers can also be used to make immunogen conjugates. Often peptides are synthesized with terminal cysteines to allow for their attachment to supports or to carrier proteins through a part of the molecule that is not important for activity or recognition. Sulfhydryl-reactive, heterobifunctional cross-linkers can be coupled to carrier proteins through their other functional group and then can be linked to peptides through terminal cysteines. This method can be very efficient and yield an immunogen that is capable of eliciting a good response upon injection.

10. Solid-Phase Immobilization

Proteins, peptides and other molecules can be immobilized on solid-phase matrices for use as affinity supports or for sample analysis. The matrices may be agarose, beaded polymers, polystyrene plates or balls, porous glass or glass slides, and nitrocellulose or other membrane materials. Some supports can be activated for direct coupling to a ligand. Other supports are made with nucleophiles or other functional groups that can be linked to proteins or other ligands using cross-linkers.

11. Protein—Protein Conjugates

One of the most widely used applications for cross-linkers is the production of protein—protein conjugates. Biological assays require methods for detection, and one of the most common methods for quantitation of results is to conjugate an enzyme, fluorophore or other molecule to a protein that has affinity for one of the components in the biological system being studied. Antibody-enzyme conjugates (primary or secondary antibodies) are among the most common protein—protein conjugates used. Secondary antibodies are relatively inexpensive and are commercially available.

Listed below is a representative sampling of commercially available cross-linkers, e.g., from Pierce Catalog and Handbook, Rockford, Ill. The table also identifies which group the linker is reactive towards, e.g., sulfhydryls, carboxyls.

REACTIVITY OF COMMERCIALLY AVAILABLE CROSS-LINKERS

| Double-Agent Cross-linker | Reactive Towards | | | | | Cleavable By | | | |
|---|---|---|---|---|---|---|---|---|---|
| | —NH$_2$ | —SH | | Non-selective (Photo- | —COOH | | | | |
| Acronym | Aminos | Sulfhydryls | Carbohydrates | reactive) | Carboxyls | Thiols | Base | Periodate | Hydroxylamine |
| ABH | | | X | X | | | | | |
| ANB-NOS | X | | | X | | | | | |
| APDP | | X | | X | | X | | | |
| APG | | | | X | | | | | |
| ASIB | | X | | X | | | | | |
| ASBA | | | | X | X | | | | |
| BASED | | | | X | | X | | | |
| BS$^3$ | X | | | | | | | | |
| BMH | | X | | | | | | | |
| BSOCOES | X | | | | | | X | | |
| DFDNB | X | | | | | | | | |
| DMA | X | | | | | | | | |
| DMP | X | | | | | | | | |
| DMS | X | | | | | | | | |
| DPDPB | | X | | | | X | | | |
| DSG | X | | | | | | | | |
| DSP | X | | | | | X | | | |
| DSS | X | | | | | | | | |
| DST | X | | | | | | | X | |
| DTBP | X | | | | | X | | | |
| DTSSP | X | | | | | X | | | |
| EDC | X | | | | X | | | | |
| EGS | X | | | | | | | | X |
| GMBS | X | X | | | | | | | |
| HSAB | X | | | X | | | | | |
| LC-SPDP | X | X | | | | | | | |
| MBS | X | X | | | | X | | | |
| M$_2$C$_2$H | | X | X | | | | | | |
| MPBH | | X | X | | | | | | |

-continued

REACTIVITY OF COMMERCIALLY AVAILABLE CROSS-LINKERS

| | Reactive Towards | | | | | Cleavable By | | | |
|---|---|---|---|---|---|---|---|---|---|
| Double-Agent Cross-linker | —NH$_2$ | —SH | | Non-selective (Photo- | —COOH | | | | |
| Acronym | Aminos | Sulfhydryls | Carbohydrates | reactive) | Carboxyls | Thiols | Base | Periodate | Hydroxylamine |
| NHS-ASA | X | | | X | | | | | |
| PDPH | | X | X | | | X | | | |
| PNP-DTP | X | | | X | | | | | |
| SADP | X | | | X | | X | | | |
| SAED | X | | | X | | X | | | |
| SAND | X | | | X | | X | | | |
| SANPAH | X | | | X | | | | | |
| SASD | X | | | X | | X | | | |
| SDBP | X | | | | | | | | |
| SIAB | X | X | | | | | | | |
| SMCC | X | X | | | | | | | |
| SMBP | X | X | | | | | | | |
| SMPT | X | X | | | | | | | |
| SPDP | X | X | | | | X | | | |
| Sulfo-BSOCOES | X | | | | | | X | | |
| Sulfo-DST | X | | | | | | | X | |
| Sulfo-EGS | X | | | | | | | | X |
| Sulfo-GMBS | X | X | | | | | | | |
| Sulfo-HSAB | X | | | X | | | | | |
| Sulfo-LC-SPDP | X | X | | | | X | | | |
| Sulfo-MBS | X | X | | | | | | | |
| Sulfo-NHS-ASA | X | | | X | | | | | |
| Sulfo-NHS-LC-ASA | X | | | X | | | | | |
| Sulfo-SADP | X | | | X | | X | | | |
| Sulfo-SAMCA | X | | | X | | | | | |
| Sulfo-SANPAH | X | | | X | | | | | |
| Sulfo-SAPB | X | | | X | | | | | |
| Sulfo-SIAB | X | X | | | | | | | |
| Sulfo-SMCC | X | X | | | | | | | |
| Sulfo-SMBP | X | X | | | | | | | |
| Sulfo-LC-SMPT | X | X | | | | | | | |

EXAMPLE 8

Prevention of Cyclization By Designing a Compound Containing an Olefin Group

In this Example, Xaa-boroPro analogs containing an olefin group, e.g., a fluoroolefin will be constructed to prevent cyclization and increase biological activity. The biological activity of this olefin containing compound will be tested by the methods described previously in Example 2, section III, e.g., comparing the production of IL-2 using an olefin containing compound versus using a compound that does not contain an olefin.

Identification of Active (Open) and Inactive (Cyclic) Species of Monomeric Compounds as Related to Inhibitory Activity of Soluble CD26 (DP IV)

Figure 10:
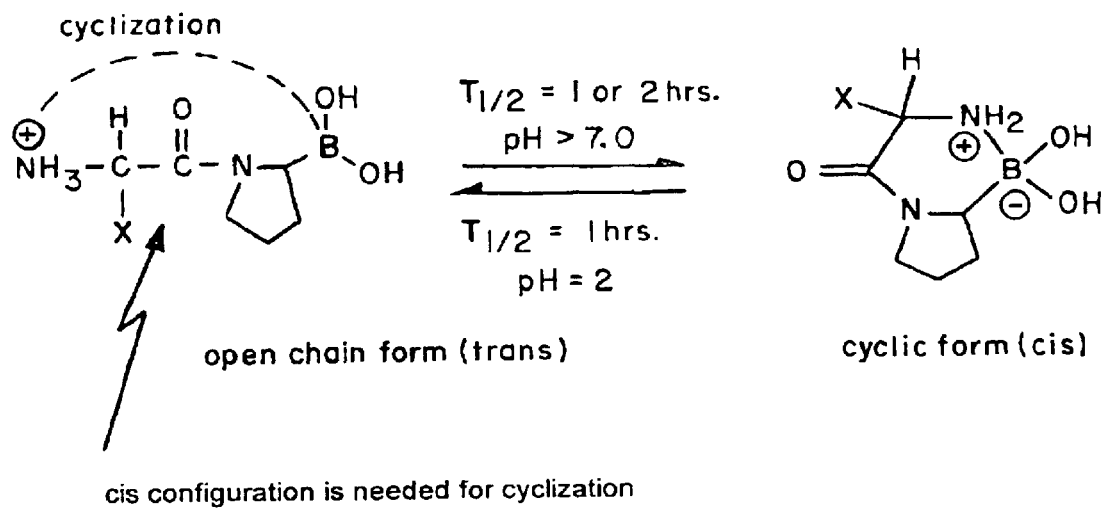
FIG. 10 is a diagram showing the structures of the open and cyclized forms of Xaa-boroProline inhibitors.

The inventors have previously shown that synthetic diastereomeric monomeric compounds, e.g., L-Ala-D,L-boroPro and L-Pro-D,L-boroPro, were potent inhibitors of the catalytic activity of soluble DP IV (CD26). They also encountered a problem because these monomeric inhibitors lost some of their inhibitory activity rapidly in aqueous solution at pH value around neutral. For example, Ala-boroPro lost DP IV inhibitory activity with a half-life of around 5 minutes and pro-boroPro lost activity with a half life of about one hour. It was determined that the inhibitors did not undergo degradation in aqueous solutions of neutral pH and higher, but undergo a cyclization reaction. In aqueous solution at all pH values, the inhibitors exist as a slowly equilibrating mixture of two conformations: an open chain structure which is inhibitory (active species), and a cyclic structure which in non-inhibitory (inactive species). See FIG. 10 which is a diagram showing the structures of the open and cyclized forms of Xaa-boroPro inhibitors (conformational equilibrium of Xaa-boroProline inhibitors). The open, active, inhibitory chain species is favored at low pH while the cyclized structure is favored at high pH. Also, the reaction is fully reversible: the open chain becomes predominate at low pH. The open chain to cyclic species reaction involves a trans to cis isomerization of the proline and the formation of a new N—B bond. The cyclized structure is the boron analog of a diketopiperazine, a product often seen in peptide chemistry. Cyclization liberates one equivalent of H+ thereby explaining the requirement for base in cyclization reaction and acid in the opening reaction. The cyclic structure is quite stable in aqueous solutions of high pH.

Prolonged incubation at high pH never leads to the is complete disappearance of DP IV inhibitory activity for any on the Xaa-boroPro compounds examined. This observation was the first evidence that the active inhibitor was in a conformation equilibrium with a non-inhibitory species rather than undergoing an irreversible inactivation. The half life for the reformation of the open chain species from the cyclic structure is surprisingly slow. Thus, the loss of inhibitory activity in aqueous solution was due to a pH dependent conformational equilibrium rather than a degradation reaction.

The fact that the inhibitory activity does not go to zero for any of the Xaa-boroPro inhibitors, even after prolonged incubation, together with the fact that the reverse reactions, i.e., cyclic to open chain is slow, suggested that it should be possible to measure the equilibrium constant for the conformation equilibrium by measuring the apparent Ki at equilibrium and comparing it with the true Ki.

It has been demonstrated that the ratio of [cyclic]:[open] forms, at neutral pH, is 156:1 for Pro-boroPro and 1130:1 for Val-boroPro (W. G. Gutheil and W. W. Bachovchin, separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, Biochemistry 32, 8723–8731 (1993)). This means that less than 1% Pro-boroPro and less than 0.1% of Val-boroPro exists as the open chain, inhibitory species, at equilibrium at pH 7.0. Nevertheless, under these conditions the inhibitors behave as though they had Ki's of 2.5 nM and 1.8 nM respectively. This apparent Ki of the "fully inactivated" species is still substantially better than, (~1000-fold) that of other inhibitors of DP IV thus far reported.

Background Information on Olefin containing compounds

Previously, fluoroolefin peptide isosteres have been used as tools for controlling peptide conformations (Boros, L. G., et al Fluoroolefin Peptide Isosteres—Tools for Controlling Peptide Conformations, Tetrahedron Letters, 35(33), 6033–6036 (1994)). Fluoroolefin containing dipeptide isosteres have also been shown to be effective inhibitors of dipeptidyl peptidase IV (CD26) (Welch, J. T, et al Fluoroolefin Containing Dipeptide Isosteres as Inhibitors of Dipeptidyl Peptidase IV (CD26), Tetrahedron, 52(1), 291–304 (1995)).

Figure 11A:
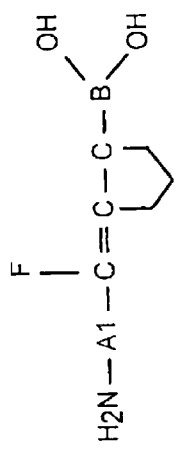
FIGS. 11A–11D are diagrams of different examples of bivalent compounds containing an olefin group.
Figure 11B:
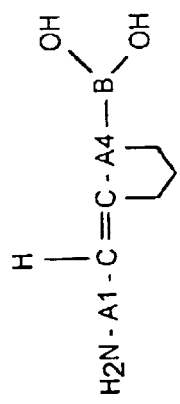
Figure 11C:
Figure 11D:
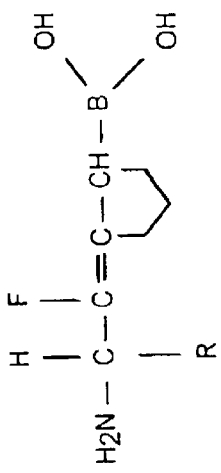
Figure 11D:
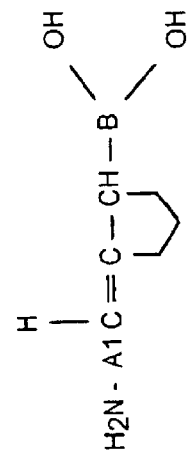
Figure 11D:
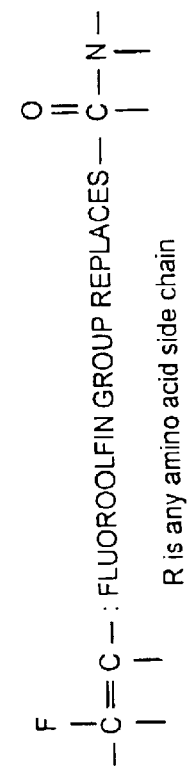

Prevent Cyclization to Increase Biological Activity of Bivalent or Multivalent Compound In view of the above data and information, the inventors predict that biological bioavailability (biological function) for the compounds taught in this invention could be significantly increased (approximately 100–1000 times) by preventing peptide conformational changes, e.g., intermolecular cyclization, by constructing a bivalent or multivalent compound containing an olefin group (a carbon atom double bonded to another carbon atom; see FIG. 11D), e.g., fluoroolefin. FIGS. 11A–11D are diagrams of different examples of bivalent compounds containing an olefin group and is not meant to limit the scope of the invention. FIG. 11D is a fluoroolefin isostere of Xaa-boroProline. A fluoroolefin mimics a peptide bond but prevents cis trans isomerization and therefore will prevent cyclization. Thus, if cyclization can be blocked, the inventors predict that the bioavailability of the compounds taught herein could be increased by approximately 100–1000 fold.

The methods used to synthesize fluoroolefins will be adapted from Livia G. Boros, Bart De Corte, Raymond H. Gimi, John T. Welch, Yang Wu, and Robert E. Hanhachumacher, "Fluoroolefin peptide isosteres—tools for controlling peptide confirmations," Tetrahedron Letters, Vol. 35, No. 33, pp. 6033 and 6036, 1994; and John T. Welch and Jian Lin, "Fluoroolefin containing dipeptide isosteres as inhibitors of dipeptidyl peptides IV (CD26)", Tetrahedron, Vol. 52, No. 1, pp. 291–304, 1996.

The fluoroolefin analogs of Xaa-boroPros will be compared to Xaa-boroPros by measuring the potency of inhibition of CD26 proteinase activity. The immunomodulatory effects of these fluoroolefin containing analogs will be evaluated by in vivo experiments using animal models and in vitro experiment using cell culture. The cell culture experiments will monitor cytokine production by cells of lymphoid origin, proliferation of cells of lymphoid origin, or both.

EXAMPLE 9

Synthesis of Fluorescently Labelled Monomeric Derivatives of Lys-boroPro

Fluorescently labelled derivatives of monomeric Lys-boroPro will be prepared and will be used to determine if monomeric Lys-boroPro induces internalization of CD26 is able by itself to enter cells. Fluorescence microscopy will be used to monitor intercellular trafficking of CD26.

One labelling approach would be to directly couple the side chain amino group of monomeric Z-Lys-boroPro-diester to a functional group on a fluorescent molecule such as the isothiocyanate of fluorescein isothiocynate (FITC). Lys-boroPro can be linked to FITC either directly or through a spacer linker molecule.

Another labelling approach is to link the side chain amino group of Lys-boroPro to biotin, again either directly or through a spacer and then use the avidin, strepavidin-biotin systems for detection.

Avidin is a glycoprotein found in the egg white and tissues of birds, reptiles and amphibia. This protein contains four identical subunits having a combined molecular mass of 67,000–68,000 daltons. Each subunit binds one molecule of biotin, and studies have shown that tryptophan and lysine are involved in the binding site for biotin. The sequencing of the subunit indicates it consists of 128 amino acids. Avidin has an isoelectric point of 10–10.5 and is very soluble in water and salt solutions. Avidin is stable over a wide range of pHs and temperatures. Extensive chemical modification has little effect on the activity of avidin, making it useful for detection and protein purification.

Streptavidin is another biotin-binding protein, and it is isolated from *Streptomyces avidinii*. The molecular weight of streptavidin is about 60,000. Unlike avidin, streptavidin has no carbohydrate and has an acidic isoelectric point of 5. Streptavidin is much less soluble in water than avidin and can be crystallized from water or 505 isopropanol.

Advantages of this approach over the above approach include: (1) the biotin-avidin system is well developed, well described and has been successfully utilized for the is type of work proposed here in many other systems; (2) improved flexibility because a large number of reagents are commercially available for use in this system: (3) improved sensitivity because this system provides for amplification of the signal from the biotinylated moiety (e.g., the biotinylated Lys-boroPro can be rendered fluorescent by reaction with either avidin (or streptavidin) conjugated either to a fluorochrome such as FITC or conjugated to an enzyme such as horseradish peroxidase). Avidin-FITC conjugate has many FITC groups per avidin molecule compared to only one in the first approach described above. The avidin-enzyme conjugate approach provides a large amplification owing to the many molecules of substrate converted to detectable product per avidin molecule.

N-hydroxysuccinimide biotin (NHS-biotin, available from Pierce Company) reacts readily with free primary amines to form a biotin conjugate linked with a peptide bond. First, NHS-biotin, and NHS-LC-biotin (which has a 22.4 Å spacer arm to separate biotin from the amino group of the molecule to which it is to conjugate) will be linked to the side chain amino group of Lysine of Lys-boroPro, and these molecules will be characterized as to their ability to inhibit DP IV and their ability to serve as a detection tool for Lys-boroPro-protein complexes using the avidin detection systems.

Each of the compounds prepared as described above will be purified to homogeneity using HPLC and its identity will

EXAMPLE 10

Synthesis of Fluorescently Labelled Bivalent and Multivalent Derivatives of LYS-boroPro Fluorescently labelled dimeric and multimeric derivatives of Lys-boroPro will be prepared and used to determine if bivalent and trivalent derivatives of Lys-boroPro can induce aggregation and internalization of cell surface CD26.

Producing such molecules can be accomplished in several ways. One way is to use a trifunctional molecule of the type illustrated below. With appropriate chemical methodology, the carboxylate groups can be coupled to Lys-boroPro molecules while the amino group can be coupled to an FITC molecule, or other fluorophore, or perhaps best of all, to biotin via a suitable length spacer. Trifunctional molecules of the type shown below are available or can be synthesized relatively easily.

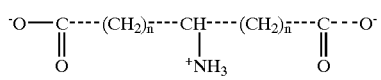

Trimeric forms of Lys-boroPro would also be possible through straightforward extension of the approach described above for the bivalent forms. Another approach would be to take advantage of the multimeric nature of the biotin-avidin system. Avidin has four subunits each of which has a biotin binding site for biotin. If such fluorescent trimeric inhibitors are needed, biotin will be coupled to Lys-boroPro through a suitable length spacer (the NHS-LC-biotin should have an adequate length spacer arm 22.4 Å). The effect of various amounts of avidin, both on T cell activation and on cell surface CD26 aggregation will be determined using FITC-conjugated avidin. This approach will probably yield a mixture of divalent, trivalent, and tetravalent inhibitors.

The compounds prepared as described above will be purified by HPLC and their structure will be confirmed by NMR spectroscopy, amino acid composition, or mass spectroscopy as necessary.

EXAMPLE 11

Synthesis of Lys-BoroPro Linked to Insoluble Supports

Lys-boroPro linked to insoluble supports may be useful for three reasons. The first is for determining the effect of such solid phase immobilization of Lys-boroPro on T cell proliferation for comparison with analogous experiments with solid phase immobilized anti-CD26 mAbs. Solid phase immobilized Lys-boroPro derivatives should induce aggregation of cell surface CD26, but differ from soluble, multimeric inhibitors in that they should prevent internalization, or at least internalization of inhibitor bound CD26. The second use will be for determining if Lys-boroPro binds to proteins other than CD26 to an appreciable extent. The third use is to produce an affinity column for producing purified CD26 from various sources.

Lys-boroPro can be immobilized on solid supports in many ways; each with certain advantages. Initially, solid state immobilized avidin together with biotinylated Lys-boroPro will be explored because this approach seems to offer the most flexibility. Solid state immobilized avidin, e.g., linked to agarose, is commercially available (Pierce Chemical Co.) with avidin and can be obtained in both multimeric and in monomeric forms. The monomeric form is designed to allow for the removal and recovery of biotinylated proteins from the resin and therefore may be preferred for the second and third purpose described above. There are, however, other ways to provide for the removal and recovery of biotinylated Lys-boroPro-protein conjugates. For example, (i) high concentration of biotin may compete with and displace the biotinylated Lys-boroPro from the solid state immobilized avidin, (ii) free Lys-boroPro may displace the biotinylated inhibitor from the proteins, (iii) a biotin derivative with a cleavable group in the spacer arm can be used in preparing the biotinylated Lys-boroPro, (iv) lowering the pH to −4.0 will dramatically lower the affinity of Lys-boroPro for the active site of DP IV and thus should allow elution of the protein from the resin leaving behind biotinylated Lys-boroPro attached to avidin (G. R. Flentke, E. Munoz, B. T. Huber, A. G. Plaut, C. A. Kettner, and W. W. Bachovchin. Inhibition of dipeptidyl aminopeptidase IV (DP-IV) by Xaa-boroPro dipeptides and use of these inhibitors to examine the role of DP-IV in T-cell function, Proceedings of the National Academy of Sciences of the United States of America 88, 1556–1559 (1991); Bachovchin, W. W., Plaut, A. G., Flentke, G. R., Lynch, M., and Kettner, C. A. Inhibition of IgA1 proteinases from *Neisseria gonorrhoea* and *Hemophilus influenzae* by peptide prolyl boronic acids, *Journal of Biological Chemistry* 265, 3738–43 (1990)). Piols, such as pinanediol or pinacol, can added to the elution buffer to bind to and thus tie up the hydroxyl groups on the boronyl group.

Each of the compounds prepared as described above will be purified to homogeneity using HPLC and its identity will be confirmed by NMR spectroscopy, amino acid composition, or mass spectroscopy as deemed necessary.

EXAMPLE 12

CD26 (DP IV) Affinity Studies

Since the purification of CD26 has remained a major problem, employing an affinity column as described below should be of substantial benefit. The fact that the linked homobivalent, dimeric molecule, $KbP_2$-Adipate, was shown to be a potent inhibitor at lower concentrations, e.g., $10^{-10}$ M, (See Example 1, I, B(1) above)) may assist in purification of CD26. Derivatizing the ε-amino group of the Lys-borPro, without sacrificing affinity, should help in developing an affinity column specific for the purification of CD26 from various sources, e.g., cell lines transfected with CD26 (DP IV) genes.

EXAMPLE 13

Measuring Standard CD26 (DP IV) Activity

Assays to measure CD26 (DP IV) activity will be performed on both the homobivalent compounds, e.g., Lys-boroPro coupled to another, and the heterobivalent compounds, e.g., Lys-boroPro coupled to a peptide specific for a T cell surface receptor, e.g., moth cytochrome C peptide. Methods for quantitatively measuring the interaction of small peptidomimetic inhibitors with CD26 or DP IV, as well as for the interaction of CD26 with larger ligands, e.g., the HIV Tat protein, have been developed (W. G. Gutheil and W. W. Bachovchin. Separation of L-Pro-DL-boroPro into Its Component Diastereomers and Kinetic analysis of Their Inhibition of Dipeptidyl Peptidase IV. A New Method for the Analysis of Slow, Tight-Binding Inhibition, *Biochemistry* 32, 8723–8731 (1993); Gutheil, W.

G., and W., B. W. Kinlsq, A Matlab Program for Fitting Kinetics Data with Numerically Integrated Rate Equations and Its Application to the Analysis of Slow, Tight Binding Data, *Analytical Biochemistry* 223, 13–20 (1994); Gutheil, W. G., Subramanyam, M., Flentke, G. R., Sanford, D. G., Munoz, E., Huber, B. T., and Bachovchin, W. W. HIV-1 Tat Binds to DP IV (CD26): A possible Mechanism for Tat's Immunosuppressive Activity, *Proc. Natl. Acad. Sci. U.S.A.* 91, 6594–6598 (1994)). These methods use the chromatogenic substrate Ala-Pro-p-nitroanilide (APpNA) and fluorescent substrate Ala-Pro-7-amino-4-trifluoromethyl coumarin (AP-AFC). APpNA and AP-AFC are commercially available (e.g., Enzyme Systems Products, Dublin, Calif.).

EXAMPLE 14

Immunological Studies on Homobivalent and Heterobivalent Compounds

This example describes functional assays that will be performed on the homobivalent and heterobivalent compounds or molecules taught herein.

1. T Cell Functional Assays

The ability of bivalent Lys-boroPro molecules designed to induce association of cell surface CD26 will be measured in an antigen specific T cell response as previously described (G. R. Flentke, E. Munoz, B. T. Huber, A. G. Plaut, C. A. Kettner, and W. W. Bachovchin, "Inhibition of dipeptidyl aminopeptidase IV (DP-IV) by Xaa-boroPro dipeptides and use of these inhibitors to examine the role of DP-IV in T-cell function," *Proceedings of the National Academy of Sciences of the United States of America* 88, 1556–1559 (1991); M. Subramanyam, W. G. Guthiel, W. W. Bachovchin, and B. T. Huber, "Mechanism of HIV-1 Tat induced inhibition of antigen-specific T cell responsiveness," *J. Immunol.* 150, 2544–2553 (1993)).

Briefly, in the human system, peripheral blood mononuclear cells (PBMC) are cultured with suboptimal doses of anti-CD3 mAbs, in the presence or absence of the CD26 associating agents. Alternatively, a recall antigen response is measured to a suboptimal concentration of tetanus toxoid or *candida* antigen, plus or minus the CD26 associating agents (M. Subramanyam, W. G. Guthiel, W. W. Bachovchin, and B. T. Huber, "Mechanism of HIV-1 Tat induced inhibition of antigen-specific T cell responsiveness," *J. Immunol.* 150, 2544–2553 (1993)).

In the murine system, the cytochrome C system is used for measuring the response in the 2B4 T cell hybridoma (G. R. Flentke, E. Munoz, B. T. Huber, A. G. Plaut, C. A. Kettner, and W. W. Bachovchin, "Inhibition of dipeptidyl aminopeptidase IV (DP-IV) by Xaa-boroPro dipeptides and use of these inhibitors to examine the role of DP-IV in T-cell function," Proc. of the Natl. Acad. of Sci. of the U.S. A. 88, 1556–1559 (1991)). Cellular activation is measured by the production of IL-2 by the T cell hybridoma, and the level of IL-2 produced is quantified in a biological assay, using HT-2 indicator cells.

2. Internalization of CD26/Drug Delivery

Because antibody mediated crosslinking of CD26 induces internalization, it is likely that homobivalent compounds of Lys-boroPro should also have this biological activity. Receptor internalization will be determined by employing FITC labelled bivalent Lys-boroPro and performing flow cytometric analysis (N. H. Dang, Y. Torimoto, K. Sugita, J. F. Daley, P. Schow, C. Prado, S. F. Schlossman, and C. Morimoto. Cell surface modulation of CD26 by anti-1F7 monoclonal antibody: Analysis of surface expression and human T cell activation, *Journal of Immunology* 145, 3963-3971 (1990)). To compare cell membrane versus cytoplasmic staining, the cells will be analyzed (i) with intact membranes, allowing only cell surface staining, and (ii) after permeabilization of the membrane with saponin, which allows the antibody to cross the membrane, although the membrane stays structurally intact (de Caestecker, M. P., Telfer, B. A., Hutchinson, I. V., and Ballardie, F. W., "The detection of intercytoplasmic interleukin 1α, interleukin-1β and tumour necrosis factor α expression in human monocytes using two colour immunofluorescence flow cytometry," *J. Immunol. Methods* 154, 11–20 (1992). Once it is demonstrated that the CD26 molecule becomes internalized after incubation with a bivalent or multivalent derivative of Lys-boroPro, a larger molecule will be coupled to the bivalent molecule, preferentially an enzyme that can be easily detected, i.e., luciferase, alkaline phosphate or β-galactosidase. Expression of either of these three proteins can be measured by using cellular extract. Kits are commercially available for this determination (e.g., Novacastra Laboratories Ltd., Newcastle upon Tyne, UK). Furthermore, mAbs are commercially available (e.g., Southern Biotech, Birmingham Ala.) for the three enzymes, enabling detection of protein expression in single cells by flow cytometry. Again, saponin will be used to permeabilize the cells, enabling entry of the mAbs. This method is very sensitive and it allows simultaneous analysis of other cell surface or cytoplasmic proteins.

USES AND ADVANTAGES

As described herein, the invention provides a number of uses and advantages. These low molecular weight, synthetic bivalent molecules are designed to induce the association between association-activated receptors and therefore offer considerable potential for regulating biological systems and thus for becoming new drugs. Thus, this new class of biologically active agents and compounds, or compositions thereof, are useful to induce the association between association-activated receptors on human T cells. These compounds or compositions thereof are useful for the treatment of a wide variety of diseases in animals; for example, autoimmune disease.

Generally, these bivalent homo- or heterobivalent compounds or compositions thereof are useful as immune response modulating therapeutics used for treatment of disease conditions characterized by immunosuppression, e.g., AIDS or AIDS-related complex, other virally or environmentally induced conditions and certain congenital immune deficiencies, or used to increase immune function which has been impaired by the use of immunosuppressive drugs or for treatment of systemic lupus erythematosis, rheumatoid arthritis, and multiple sclerosis.

For example, the compounds of this invention may be used to deliver a member of the superantigen family to stimulate T cells. Superantigens comprise a class of disease-associated, immunostimulatory molecules that bind class II MHC molecules and stimulate large numbers of T cells (Jardetzky, T. S., et al. "Three Dimensional Structure of a Human Class II Histocompatibility Molecule Complexed with Superantigen", *Nature,* 368, 711–718 (April, 1994)). Members of the superantigen family include toxins from *S. aureus* and other bacteria, as well as viral superantigens from mouse mammary tumor virus. The toxicity of the bacterial superantigens is thought to be mediated by their potent T-cell stimulating activities, leading to lymphokine release, respiratory distress and shock. Superantigens have also been implicated in rabies, rheumatoid arthritis, and mouse and human AIDS.

These bivalent homo- or heterobivalent compounds or compositions thereof may be used to stimulate the growth of hematopoietic cells in culture. Such cells can be transplanted into mammals, e.g., humans, to strengthen or boost the hematopoietic, immune system, or both. These compounds may also be used to treat patients suffering from disease or from deficiency of hematopoietic cells such as AIDS patients, patients undergoing chemotherapy or patients undergoing radiotherapy for hematological or other cancers, and patients undergoing bone marrow transplants.

When administered to mammals, e.g., humans, the compounds of the invention may enhance the ability of the immune system to regenerate cells that are immunosuppressed, e.g., $CD4^+$ T cells. Thus, the bivalent compounds of this invention e.g., as in claims 1, 17, and 34, may be administered to mammals, e.g., humans, in an effective amount alone or in combination with a pharmaceutically acceptable carrier, excipient, or diluent, in unit dosage form. Conventional pharmaceutical practice may be employed to provide suitable formulations or compositions to administer these compounds to patients suffering from immunosuppression or an immune deficiency or presymptomatic of AIDS. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxyproplyene copolymers may be used to control the release of the compounds. Other potentially useful parenteral delivery systems for these bivalent compounds include ethylenevinyl acetate copolymer particles, osmotic pumps, implantable infusion systems or liposomes. Formulations of inhalation may contain excipients, for example, lactose, or may be aqueous solutions containing, for example, polyoxethylene-9-lauryl ether, glycocholate and deoxycholate, or may be oily solutions for administration in the form of nasal drops, or as a gel.

These bivalent homo- or heterobivalent compounds or compositions thereof may be used to control the T cell activation process and thus be used to prevent unwanted immune responses.

The homobivalent compounds designed to induce the association between one CD26 T cell receptor and another CD26 T cell receptor may be useful in stimulating the proliferation of CD4+cells. These compounds could therefore help restore CD4+cells numbers in immunosuppressed patients, e.g., AIDS patients, and thereby reverse the decline in immune function.

The homobivalent compounds or compositions thereof (CD26 T cell receptor associated with another CD26 T cell receptor) of claim 1 may be used to enhance recall-antigen specific immune responses. Lymphocytes from most HIV-infected individuals exhibit a qualitative defect in their ability to respond to recall antigens (A. S. Fauci. The human immunodeficiency virus: infectivity and mechanisms of pathogenesis. Science 239, 617–722 (1988)). This defect is exhibited early after infection and long before CD4+ T cell numbers decline. These compounds may therefore prove useful in treating AIDS. Thus, the stimulatory activities may improve lymphocyte function in HIV infected individuals by ameliorating the defective recall antigen responses which show up early after infection, and by improving $CD4^+$ T cell numbers.

Since the compounds or compositions thereof of claim 1 have high affinity and specificity for CD26, they may be useful for the selective delivery of other therapeutic agents to, and into CD4+ T cells. This activity could be used to deliver pharmacological agents inside CD4+cells that normally cannot enter CD4+cells on their own. For example, many highly potent inhibitors of the HIV protease have been developed, which despite their high affinities for the HIV proteinase, are limited in blocking HIV in vivo owing to their inability to get inside CD4+cells. These HIV proteinases inhibitors could be linked to the spacer arm of a bivalent CD26 ligand and delivered into CD26+lymphocytes, which are the cells the virus primarily invades. Even if a drug is capable of entering CD4+cells, the compounds or compositions thereof may be used to concentrate it in CD26 cells, thereby maximizing the desired pharmacological activity while minimizing unwanted toxic side effects on other cells. This delivery vehicle might therefore provide a mechanism to prevent or even overcome AZT resistance by providing for higher concentrations of AZT in CD4+cells and lower concentrations elsewhere. Thus, the CD26 internalization activity may prove useful by providing a vehicle for delivering and concentrating other therapeutic agents into CD4+ T cells.

The heterobivalent compounds designed to induce the association between a CD26 T cell receptor and a different T cell receptor, e.g., the T cell receptor TCR/CD3, may be useful in stimulating a cell-mediated immune response against specific antigens. Heterobivalent compounds or compositions thereof comprising a CD26 inhibitor and an antigenic peptide stimulate a cellular immune response against an antigenic peptide as compared to an antibody-mediated immune response. This stimulation of cell-mediated response against specific antigens would be useful in patients with AIDS because these patients have high concentrations of anti-HIV antibodies. Thus, the CD26-TCR association-inducing activity may be useful for stimulating a cell mediated immune response to specific antigens. This biological activity may prove especially useful in vaccine development, particularly for AIDS because a cellular or $T_H1$ immune response is the appropriate response for HIV-1 and is apparently lacking in AIDS patients.

Such heterobivalent compounds may therefore be useful in the development of peptide-based vaccines or as potential therapeutic agents in the treatment of allergies and autoimmune diseases.

Because the response stimulated is cell mediated and specific for the antigen chosen, such bifunctional agents may prove useful in the development of vaccines as a cell mediated immune response, especially for AIDS.

The heterobivalent compounds designed to induce the association between a CD26 T cell receptor and a different T cell receptor, e.g., CD4, may be useful in activating T cell function. This heterobivalent compound or compositions thereof may be used to selectively deliver agents to CD4+ CD26+ cells, or they may be useful in blocking HIV entry into CD4+ cells.

The heterobivalent compounds or compositions thereof e.g., as shown in claim 17, may be used to deliver a toxin, e.g., ricin A immunotoxin or AZT, within a CD26+ T cell. A toxin of choice may be coupled to a dimeric compound having high affinity for the CD26 T cell surface receptor. Also, a toxin may be coupled to a peptide having specificity for a specific T cell receptor. Either way, once the dimeric compound associates or binds to the CD26 T cell surface receptor, the toxin will be internalized within the T cell, thereby delivering this toxin to a T cell.

The compounds or compositions thereof may be administered alone or in combination with one another, or in combination with other therapeutic agents. For example, treatment with one of the bivalent compounds may be combined with more traditional immune deficient therapies.

Other embodiments are within the following claims.

---

What is claimed is:

1. A compound, having the structure $$D1\sim A1\sim A2\sim A3\sim A4-B\begin{matrix}Y_1\\ Y_2\end{matrix} \quad D2\sim A5\sim A6\sim A7\sim A8-B\begin{matrix}Y_3\\ Y_4\end{matrix}$$
$$\underline{\qquad\qquad\qquad L \qquad\qquad\qquad}$$

wherein D1 and D2, independently, are selected from the group consisting of NH and $NH_2$,
wherein N represents any isotope of nitrogen,
wherein H represents any isotope of hydrogen;
"~" independently, is selected from the group consisting of a single bond and a double bond;
B represents, independently, any isotope of boron;
A1 and A5 are, independently, selected form a group consisting of a C, a CX moiety and an N,
wherein C represents any isotope of carbon,
wherein X represents any atom that forms a single bond with C;
each A2, A3, A4, A6, A7, and A8 are, independently, selected from a group consisting of a CX moiety, a CXZ moiety, a CZ moiety, an NX moiety, and an O,
wherein X and Z, are, independently, selected from the groups consisting of any atom that forms a single bond and any atom that forms a double bond with C or N and wherein O represents any isotope of oxygen;
wherein each Y1, Y2, Y3, and Y4 are, independently, selected from the group consisting of hydroxyl moiety and any reactive moiety that converts to a hydroxyl group moiety under physiologic conditions; and
L represents a linker moiety containing a chain of atoms selected from the group consisting of a combination of C, O, N, S, and P atoms, connected by single bonds or by double bonds in a manner that does not violate the laws of chemistry and wherein S represents any isotope of sulfur and P represents any isotope of phosphorous, wherein L has a molecular weight ranging between 100 daltons and 2000 daltons, or
L has a span ranging from 20 Å to 300 Å.

2. The compound of claim 1 wherein the following structures $$D1\sim A1\sim A2\sim A3\sim A4-B\begin{matrix}Y_1\\ Y_2\end{matrix} \quad \text{and} \quad D2\sim A5\sim A6\sim A7\sim A8-B\begin{matrix}Y_3\\ Y_4\end{matrix}$$
$$\begin{matrix}|\\ R\end{matrix} \qquad\qquad\qquad \begin{matrix}|\\ R\end{matrix}$$

represent, independently, a binding moiety, wherein R represents the remainder of the molecule.

3. The compound of claim, 2 wherein there are four atoms positioned between the group consisting of D1 and D2 and B of the binding moiety.

4. The compound of claim 2 wherein the binding moiety includes a carbon atom in an L-configuration.

5. The compound of claim 2 wherein the binding moiety is an L-amino acid derivative, wherein the carboxylic acid group of the L-amino acid has been replaced by a boron-containing group.

6. The compound of claim 2 wherein the binding moiety is selected from the group consisting of L-Lys-L-boroPro, derivatives of L-Lys-L-boroPro, L-Pro-L-boroPro, derivatives of L-Pro-L-boroPro, L-Ala-L-boroPro, derivatives of L-Ala-L-boroPro, L-Val-L-boroPro, and derivatives of L-Val-L-boroPro.

7. The compound of claim 1 wherein the linker moiety contains a functional group selected from the group consisting of a carboxylate group, an amino group, a sulfhydryl group, an imidazole group, an alkene group, an acyl halogen group, and $CH_2X$, wherein X represents a halogen.

8. The compound of claim 1 wherein $Y^1$, $Y^2$, $Y^3$ and $Y^4$ are hydroxyl groups.

9. The compound of claim 1 wherein the A4 is CXZ, and the A4 bonded to B is in the L-configuration; and wherein A8 is CXZ, and the A8 bonded to B is in the L-configuration.

10. The compound of claim 1 wherein the linker moiety span ranges from 30 Å to 100 Å.

11. The compound of claim 1 wherein the linker moiety is further defined as having the following structure:

$$\begin{matrix}|&&|\\ [G]_m&&[G]_m\\ |\underline{\qquad[J]_p\qquad}|\end{matrix}$$

wherein [G] is selected from the group consisting of a carbon, nitrogen, oxygen, hydrogen, and a sulfur atom; [J] is selected from the group consisting of a CH molecule, a chain of carbon atoms, a chain of nitrogen atoms, a chain of oxygen atoms, and combinations thereof, and m, p, and q represent an integer from 1 to 50, inclusive.

12. The compound of claim 11 wherein [G] is an R group selected from the group consisting of L-amino acid residues selected from the group consisting of lysine, cystine, glutamic acid, aspartic acid, histidine, arginine glutamine, and asparagine and D-amino acid residues selected from the group consisting of lysine, cysteine, glutamic acid, aspartic acid, histidine, arginine, glutamine, and asparagine.

13. The compound of claim 1 wherein the linker moiety contains at least two sulfhydryl groups when the binding moieties contain cysteine residues.

14. The compound of claim 1 wherein the linker moiety is selected from the group consisting of hexanedioic acid (adipic acid), ethylene glycobissuccinate (EGS), 1,4-diaminobutane, 1,4-dithiobutane, dithiothreitol, lysine, cysteine, glutamic acid, aspartic acid, histidine, arginine, glutamine, and asparagine.

15. The compound of claim 1 wherein the linker moiety contains at least two amino groups when the binding moieties contain aspartic acid residues.

16. The compound of claim 1 wherein the linker moiety contains at least two amino groups when the binding moieties contain glutamic acid residues.

17. A compound, having the structured $$D1\sim A1\sim A2\sim A3\sim A4-B\begin{matrix}Y^1\\ Y^2\end{matrix}$$
$$\begin{matrix}|\\ [G]_m\\ |\end{matrix}$$
$$E_1-[J]_m-E_2-\!\!\!-[J]_q-E_8'-\!\!\!-$$
$$\left[\begin{matrix}&&D1\sim A1\sim A2\sim A3\sim A4-B\begin{matrix}Y^1\\ Y^2\end{matrix}\\ &&|\\ &&[G]_m\\ &&|\\ -E_r'-[J]_p-E_3-\!\!\!\!\!-[I]_q-E_8'-\end{matrix}\right]_D$$

-continued

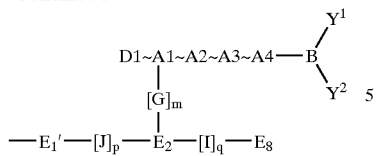

wherein D is, independently, selected from the group consisting of NH and NH$_2$,
wherein N represents any isotope of nitrogen,
wherein H represents any isotope of hydrogen;

"~" independently, is selected form the group consisting of a single bond and a double bond;

B represents, independently, any isotope of boron;

A1 is, independently, selected from the group consisting of a C, a CX moiety, and an N,
wherein C represents any isotope of carbon,
wherein X represents any atom that forms a single bond with C;

each A2, A3, and A4 are, independently, selected from the group consisting of a CX moiety, a CXZ moiety, a CZ moiety, an NX moiety, and an O, wherein X and Z, independently, are selected from the group consisting of any atom that forms a singe bond and any atom that forms a double bond with C or N and wherein O represents any isotope of oxygen;

wherein Y1 and Y2 are, independently, selected from the group consisting of a hydroxyl moiety and any reactive moiety that converts to a hydroxyl group moiety under physiological conditions;

n represents an integer between 0 and 199, inclusive;

wherein E1 and E3 are independently selected from the group consisting of a carboxylate, amino, imidazole, sulfhydryl aldehyde, ester, amide, acid chloride, carbonate, and carbamate group such that the E1 and E3 react and form an -E1-E3'- adduct with a covalent bond between E1' and E3';

wherein $[J]_p$, E2, $[I]_q$, and $[G]_m$ together comprise a linker moiety, and wherein $[G]_m$, $[J]_p$, and $[I]_q$ represent, independently, a linker group containing a chain of atoms selected from the group consisting of a combination of C, O, N, S, and P atoms, connected by single bonds, double bonds, or triple bonds in a manner that does not violate the laws of chemistry and wherein S represents any isotope of sulfur and P represents any isotope of phosphorus; and wherein m, p, and q represent, independently, an integer from 1 to 50, inclusive; and wherein the linker group has a molecular weight ranging 100 daltons and 2000 daltons or has a span ranging from 20 Å to 300 Å;

E2 is selected from the group consisting of CX, CH, N, PYZ, PU, and B such that E2 forms a covalent bond with $[J]_p$, $[G]_m$, and $[I]_q$ and
wherein C is any isotope of carbon;

X is, independently, selected from the group consisting of any atom that forms a single bond with carbon;

Y is, independently, selected from the group consisting of any atom that forms a single bond with phosphorous;

Z is, independently, selected from the group consisting of any atom that forms a single bond with phosphorous;

H is any isotope of hydrogen;

N is any isotope of nitrogen;

P is any isotope of phosphorus;

B is an isotope of boron;

U is, independently, selected from the group consisting of any atom that forms a double bond with phosphorous.

18. The compound of claim 17,
wherein [G] is the side chain of a D- or L-isomer of lysine, cysteine, glutamic acid, aspartic acid, histidine, arginine, glutamine, and asparagine;

$E_2$ is a D- or L-isomer of lysine, cysteine, glutamic acid, aspartic acid, histidine, arginine, glutamine, and asparagine; and $E_1$ and $E_3$ are selected from the group consisting of an amino moiety and a carboxylic acid moiety.

19. The compound of claim 17,
wherein $[G]_m$ is the side chain of a D- or L-isomer of lysine, cysteine, glutamic acid, aspartic acid, histidine, arginine, glutamine, and asparagine;

$E_2$ is selected from the group consisting of 2-carboxybutyl, 2-carboxypropyl, 2-aminobutyl, 2-aminopropyl, and a hydrocarbon chain with an amino or carboxy side chain;

$[J]_p$ and $[I]_q$ represent, independently, hydrocarbon chains; and $E_1$ and $E_3$ are selected from the group consisting of an amino moiety and a carboxylic acid moiety.

20. The compound of claim 17 wherein $Y^1$ and $Y^2$ are hydroxyl groups.

21. The compound of claim 17 wherein the A4 is CXZ, and the A4 bonded to B is in the L-configuration.

* * * * *